(12) United States Patent
Dallos et al.

(10) Patent No.: US 6,602,992 B1
(45) Date of Patent: Aug. 5, 2003

(54) MAMMALIAN PRESTIN POLYNUCLEOTIDES

(75) Inventors: Peter Dallos, Wilmette, IL (US); Jing Zheng, Morton Grove, IL (US); Laird D. Madison, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 09/785,381

(22) Filed: Feb. 16, 2001

Related U.S. Application Data

(60) Provisional application No. 60/183,461, filed on Feb. 18, 2000.

(51) Int. Cl.[7] ............................................. C07H 21/04
(52) U.S. Cl. ..................... 536/23.5; 536/23.1; 536/24.3
(58) Field of Search ............................... 536/23.1, 23.5, 536/24.3, 24.31, 24.33; 530/350

(56) References Cited

PUBLICATIONS

Altschul, et al. 1997, Nucleic Acids Res. 25:3389–3402.
Altschul, et al., 1990, J. Mol. Biol. 215:403–410.
Ashmore, et al., 1987, J. Physiol. (London), 388:323–347.
Bishop, Ed., 1998, Guide to Human Genome Computing, Academic Press, New York.
Dallos, P., Overview: Cochlear Neurobiology, pp. 1–43, Springer, NY, 1996.
He and Dallos, 2000, JARO, 1:64–81.
He, et al, 2000, Hearing Res., 145:156–160.
He, et al., 1997, J. Neurosci., 15:3634–3643.
Hoffman, et al., 1993, Biol. Chem., 347:166.
Holley, et al., 1988, Proc. R. Soc. Lond. Ser. B. Biol. Sci., 232:413–429.
Hopp, et al., 1981, Proc. Natl. Acad. Sci. USA 78:3824.
Karlin and Altschul, 1990, Proc. Natl. Acad. Sci. USA 87:2264–2268.
Karlin and Altschul, 1993, Proc. Natl. Acad. Sci. USA 90:5873–5877.
Kyte, et al., 1982, J. Mol. Biol. 157:105–132.
Mammano, et al., 1999, J. Neurosci., 19(16):6918–6929.
Santos–Sacchi, et al., 1991, J. Neurosci., 11:3096–3110.
Sonnhammer, et al., 1998, Proc. 6th Intern. Conf. On Intelligent Systems for Mol. Biol., 175–182.
Swindell, Ed., 1997, Sequence Data Analysis Guidebook, Humana Press, New Jersey.

*Primary Examiner*—Gary Kunz
*Assistant Examiner*—Ruixiang Li
(74) *Attorney, Agent, or Firm*—Morgan, Lewis & Bockius, LLP

(57) ABSTRACT

The invention relates to mammalian prestin protein, which has been discovered to be the mammalian cochlear outer hair cell motor, and to polynucleotides encoding prestin. Full length gerbil prestin and its cDNA are described, full length murine prestin and its cDNA are described, and a partial sequence of human prestin and its chromosomal location are described.

6 Claims, 44 Drawing Sheets

```
  1    ....MDHAEENEIPVATQKYHVERPIFSHPVLQERIHVMDKVSESIGDKLKQAFICTPKKCIRNIIYMFLPITKWLPAYKFKEYVLGDLVSGISIGVLQLP
  1    MAARDRRSEPPQLAEYSCSYAVSRPVYSEIARQQQRERRLPERRTLRDSIARSCSCSRKRAFGALKAILPILDWLPKYRVKEMLLSDIISGVSIGVGTL

91    QGLAFAMLAAVPPVFGLYSSFYPVIMYCFEGISRHLSIGPFAVISLMGGVAVRLVPDD..IVIPGG.....VNAIN.GIFEARDAIRVKVAWSVTLLSGIIQ
101    QGVAYALLAAVPVQYGLYSAFFPILIYFVFGISRHISVGPFFWSIMGSVVLSVAPDDHFLMPSGNGSTINTTLDIGIRDAARVLIASTLTLLVGIIQ

191    FCLGVCRFGFVAIYLTEPLVRGFTTAAAVHVFTSMLKYLFGVKTKRYSGIFSVVYSTVAVLQNVKNINVCSLGVGLMFGLLLGGEFNERFKEKLPAPI
201    LVFGGLQIGFTVRYLADPLMGGFTTAAAFQVLVSQLKIVLNVSTKNMNGVLSIYTLIEFQNIGDINLADFTAGLLTIIVCMAVAKELNDRFKHKIPVPI

291    PLEFFAVVMGIGISAGFNLHESYSVDVVGTLPLGLLPPANPDTSLFHLVYVDAIATAIVGFSVTLSMAKTLANKHGYQVDGNQELTALGICNSIGSLFQT
301    PIEVIVTIATAISYGANLEANYNAGIVKSIPSGFTPPVLPSWGLFSDMLAASFSTAVVAYAIAVSGKVVATKHDYIIDGNQEFTAFGISNVFSGFFSC

391    FSISCSLSRSLVQEFGIGEKTQLAGCLASIMILIVIATGFLFESLPQAVLSAIVINLGMFWQFSDLPFHWRTSKCELTIWLITFVSSLFLGLDYGLIT
401    FVATTAISRIAVQESTGEKIQVAGLISAVIVMAIVAIGKLLEPLQKSVLAAVVIANLKGVFMQVCDVPRLWKQNKTLDAVIWFTICMSIIIGLDIGLLA

491    AVITALLTIVLYRIQSPSYKVIQGLPDIIDVYIDIDAYEEVKEIPGIKIFQINAPIYYANSDLYSNAIKRKGVNPALIMGARRKAMRKVAKEVGNANIANA
501    GLLFGLITVLRVQFPSMNGIGSVPSIDIYKSITHYKNLEEPEGVKILRFSSPIFYGNVDGFKKCVKSTVGFDATRVNKRLKALRRIQKLLKKGQLRAT

591    AVVVKMDGEVDGENATKPE...EEIDEVKYP..PIVIKTITFPEEL..QRFMPQTENVHTIILDFIQVNFTIDSVGVKTLMVVKEYCDVGTYVYLAGCSPQV
601    KNGILSDVGSSINAFEDEDVEEPEELDIPTKETEIQVDMNSELPVKVNVPKVP.IHSLVLDCGAVSFLDVVGVRSLRMLVKEFQRIDVNVYFALLQDDV

684    VNDLITRNRFFENPALKELLFHSIHDAVLGSHVREFAMAEQEASAPPPQDIMEPNATPITPEA*             745
700    LEKMEQGGFFDNIRKDRFFLTVHDAIL.........YLQNQAKSREGQDSLLETITILLIQDCKDPLEMEAEINEEELDVQDEAMRRLAS*         781
```

```
                        109                      130
                         |                        |
GERBIL PRESTIN          PVFGLYSSFYPVIMYCFFGTSR
HUMAN PRESTIN           PIFGLYSSFYPVIMYCFLGTSR
HUMAN PENDRIN           VGYGLYSAFFPILTYFIFGTSR
HUMAN DRA               PVYGLYASFFPAIIYLFFGTSR
HUMAN DTD               PVYGLYTSFFASIIYFLLGTSR
MOUSE DTD               PIYGLYTSFFASIIYFLFGTSR
                        * ****    *     *  ****

S. CEREVISIAE           PEYGLYSSFIGAFIYSLFATSK
N. CRASSA (FUNGUS)      PEYGLYTSFVGFVLYWAFATSK
G. MAX (SOYBEAN)        PEYGLYTGIVPPLIYAMLASSR
S. HAMATA (PLANT)       PQYGLYTSVIPPVIYALMGSSR
C. ELEGANS              PVYGLYTAIFPSFLYIFFGTSK
E. COLI                 PQYGLYTAAVAGIVIALTGGSR
                        * ****           *    *
```

```
GCGGCCGCGT CGACGGCAGC GGCGGCTCCG CCCTGCGCAG CCCCGGCAGC
GCTGGCTGGT GGCGGGGGAG GGCGAACAGT CCCTTTTCCA GCCCTCAGCA
GTTGACTGCC CTGTACCTGG AGTTCCCAGC CGGCTTTCCA TCCCCTGTAC
CTTGTGCTAT ACGTTGGATC TGGTGCCTGT CCAGAAATGC TCGTCTCCTG
CTGTTGGTGA ATAACTGCAG ACCATGGATC ATGCCGAAGA AAATGAAATC
CCTGTGGCAA CCCAGAAGTA CCACGTGGAA AGGCCTATCT TCAGTCATCC
CGTCCTCCAG GAGAGGCTGC ATGTCAAGGA CAAAGTCTCA GAGTCCATTG
GGGATAAGCT GAAGCAGGCG TTCACATGCA CTCCCAAAAA GATAAGAAAC
ATCATTTACA TGTTCCTGCC CATCACTAAG TGGTTGCCAG CTTACAAGTT
CAAGGAGTAT GTGTTGGGTG ACTTGGTTTC AGGCATAAGC ACCGGCGTGC
TTCAGCTTCC CCAAGGCTTA GCCTTCGCAA TGCTCGCGGC TGTTCCTCCG
GTGTTCGGCC TGTACTCTTC ATTTATCCT GTTATCATGT ACTGTTTCTT
TGGACCTCC AGACACATAT CTATAGGTCC TTTCGCCGTC ATTAGTTTGA
TGATCGGTGG TGTGGCTGTC CGGCTGGTCC CCGATGACAT CGTCATCCCG
GGAGGAGTGA ACGCAACCAA CGGCACGGAG GCCCGAGACG CGCTGAGAGT
GAAAGTCGCC ATGTCTGTCA CCCTGCTCTC AGGAATCATT CAGTTTTGCC
TAGGTGTGTG CAGGTTTGGA TTTGTGGCCA TATACCTCAC GGAGCCGCTG
GTGCGAGGGT TCACCACCGC CGCCGCCGTG CACGTCTTCA CATCCATGTT
GAAATACCTG TTTGGGGTTA AGACAAAGCG GTACAGTGGG ATCTTTTCGG
TGGTATATAG TACAGTTGCT GTGTTGCAGA ATGTTAAAAA CCTCAACGTG
TGTTCCCTAG GCGTCGGCCT GATGGTTTTT GGTTTGCTGT TGGGTGGCAA
GGAGTTTAAT GAGAGATTTA AAGAGAAATT GCCAGCACCC ATTCCTCTAG
AGTTCTTTGC TGTGGTGATG GGAACTGGCA TTTCCGCGGG GTTTAACTTG
CACGAGTCCT ACAGTGTGGA TGTCGTTGGA ACTCTTCCTC TGGGGCTACT
CCCTCCTGCC AACCCGGACA CCAGCCTCTT CCACCTCGTG TATGTGGATG
CCATTGCCAT AGCCATCGTT GGATTTTCAG TGACAATTTC CATGGCCAAA
ACCTTGGCGA ATAAGCATGG CTACCAGGTT GATGGCAATC AGGAGCTCAT
CGCTTTGGGG ATATGCAACT CCATCGGATC TCTCTTCCAG ACCTTCTCCA
TTTCCTGCTC CTTGTCTCGC AGCCTTGTTC AGGAGGGAAC TGGAGGGAAA
ACACAGCTCG CAGGTTGCTT GGCCTGCTG ATGATTCTGC TGGTCATTTT
AGCCACTGGA TTCCTCTTTG AGTCATTGCC CCAGGCTGTG CTCTCGGCCA
TTGTGATCGT GAACCTGAAA GGGATGTTTA TGCAGTTCT AGATCTGCCC
TTCTTCTGGA GAACCAGCAA AATAGAGCTG ACCATCTGGC TTACCACCTT
TGTGTCCTCC CTGTTCCTGG GCTTGGACTA CGGACTGATT ACTGCTGTGA
TCATTGCTCT GCTGACTGTG ATTTACAGAA CCCAGAGTCC GAGCTACAAG
GTCCTGGGGC AGCTCCCTGA CACCGATGTA TACATTGACA TAGACGCATA
TGAGGAGGTG AAAGAAATTC CTGGAATAAA AATATTCCAG ATAAACGCCC
CAATTTACTA TGCAAACAGT GACTTGTATA GCAACGCCCT AAAAAGAAAG
ACTGGTGTGA ACCCAGCGCT CATAATGGGA GCAAGAAGGA AGGCCATGAG
GAAGTACGCA AAGGAAGTCG GAAACGCCAA CATTGCCAAC GCAGCTGTTG
TCAAAGTGGA TGGAGAAGTA GATGGAGAAA ATGCTACGAA GCCCGAAGAA
GAGGATGATG AAGTAAAATA TCCCCCAATA GTCATCAAAA CAACATTTCC
```

FIG. 7B

```
TGAAGAGCTG CAGAGATTTA TGCCCCAGAC AGAAAATGTC CACACTATCA
TTCTAGACTT CACACAAGTC AATTTTATCG ACTCTGTTGG AGTAAAAACC
CTGGCTGTGA TGGTGAAGGA ATACGGAGAT GTTGGTATTT ATGTGTACTT
AGCAGGATGC AGCCCACAAG TCGTGAATGA CCTCACCCGC AACCGTTTCT
TTGAAAATCC TGCCTTAAAA GAGCTTCTGT TCCACAGTAT CCATGATGCA
GTCTTGGGCA GCCATGTTCG AGAGGCAATG GCTGAGCAAG AAGCCTCAGC
CCCACCTCCC CAGGACGACA TGGAGCCCAA TGCCACACCC ACCACACCCG
AGGCATAAAG GGCCTGCCTG GCCTGTGCA CCTCTTGAAT CTGAACTTA
CATGCTTTAA ATACCAGGCC TTAGGTTTTC TTCTACCCAA CCCCCAACCC
CCAAGGAAAA TGTTAGTAGT TATGGCTTGA TTTGGAGGGT GAATGATGTG
TAGTGCGATG TATCTCAGAC TTGTGTTATT TTATCTGAAT AATTCAAAGA
TTAAGTGGCC TTTCGCACTT ATGTAGTGAT GTTTGTATTA TATCTTAAAG
TCAAAAAAAA AAAAAAAAA AAAAGTCGA CGCGGCCGCG GTCGACGCGG
GCGCGAATTC GCGGCCGCGT CGACTTTTTT TTTTTTTTTT TTTTTTTTTC
TTGTCAACAT TTTAATGCAA ACAATATAGT GTTTTGACT CTAGGCATCT
GTAACGAAAC AGTGCTAGAA TGGGATAAGC ATCTGCAGCT TCTGTGGAGT
GAATGCAATT AGAACTACTC TGCCCCTGAC TGCAGAAGCC AGGCATTGTG
GCCCACACCT GCCAACCTCC ACTGAGGAGG CTACGGCAGG ACGATCACAG
TGAGTTCCAG GCCAGCCTGG GCTACAGAGG GAGGCTCAAA CCCCAAAACT
AAACAAATTA AAACAAAAC AAAACCAAG GGGAAATTCT TGTCAAGCTC
CTTTGAAAGC TGATGTTTCA AAGCACAGGA TTTGTCTTCT CTAGTAGAGA
TATATTTCCT AAGGGAGTGG AAGGAGTAAG GTTCAGGCTT ACCTGTCTGT
GAAACACCAC AAGCAGTCTC ATCCAGACCA CTGCTTCCCC TGACTCCCTT
TGCACATGGA GGACAAACAC TTGGAGAGGA ACTTAGGTGA CCTGCTTGCT
GCAAAAATCA ACTATCAAGA AAGATTTGGA GAAACGCTAG TCTGAGAAAC
GAGATTACAA GAGCCTGTGG ATTTCTTCCC TGCAACACTG GGGCCAACCT
TTCATGTCTG ATCAGAAATA ACGGGCATAG TGTTTATTGT AAGCCTGAAC
CATGAAGACA GAGCACTGAG ATAGGAAGCC CATTTGACAG TGGCAATTTC
AAATTAACAG CTTAGTTATG ATGGAACACA AACTGCAAAG GCCTTCATTT
CCTGTGTTTG GATGAAGTCA CGATCCAACA GTGGGTTAAG AGTGTGGAAG
GTAGAAGGCA GCAGCTGAAC TGTTGTGAGT GGTCCAAGGA GGCAGAGATG
CTTCAAGCAC TCCTCGCCAC CCTCAGCTTC TCTTCAAGGA GCCAAGAGGA
TGAGGAGCTG GTGCACCCAG AGGGTCTAAC CGGGGCTTGC AGAGTCCTAA
AGACATCTCT CTGCAGGCAG AAATTGCACA GCTTAATTCT TCTAGACTGA
ACAGCTTCAG ATTTATGCCA GTGGAAAGCA AACATTGTTT CTAAGTCATT
TAATTGTGTT ACTGTCTCTC AACTTTATCA GATGTTGCTT GGGTAGAGAG
GCCTGTGTGC AGTTCTGAGG GCGGCTTTAT GGTGCTCCCT GGCTCCTTCT
AAATGCCCAC AGCCCAGAGT CCCTAATGGA GCACTTTCCA GATGTAAAAA
CTACTAATTC AAAAGGTTCA AATGGCATTT GTCTCAATCC AGGACGCACA
CTGAAGGCTG CATCTTCACC AAATCGACAA CCTTGATCGC AGGTGCTAGG
TCGACGCGGC CGC
```

```
TTCCTGGGCTTGACTACGGAGACTGATTACTGCTGTGATCATTGCTCTGCTGACTGTGATTACAGAACCAGAGTCCAGAGTCCAGCTACAAGGTC
 F  L  G  L  D  Y  G  L  I  T  A  V  I  I  A  L  L  T  V  I  Y  R  T  Q  S  P  S  Y  K  V

CTGGGGCAGCTCCCTGACACCGATGTATACATTGACATAGACGCATATGAGGAGGTGAAAGAAATTCCTGGAATAAAATATTCCAGATA
 L  G  Q  L  P  D  T  D  V  Y  I  D  I  D  A  Y  E  E  V  K  E  I  P  G  I  K  I  F  Q  I

AACGCCCCAATTTACTATGCAAACAGTGACTTGTATAGCAACATGGTGTGAACCCAGCTCATAATGGGAGCA
 N  A  P  I  Y  Y  A  N  S  D  L  Y  S  N  A  L  K  R  K  T  G  V  N  P  A  L  I  M  G  A

AGAAGGAAGCCATGAGAAGATACGCAAAGAAGTCGGAAACGCCAACATTGCCAACGCAGCTGTGTCAAGTGGATGGAGAAGTAGAT
 R  R  K  A  M  R  K  Y  A  K  E  V  G  N  A  N  I  A  N  A  A  V  V  K  V  D  G  E  V  D

GGAGAAAATGCTACGAAGCCCGAAGAGGATGATGAAGTCAAATATCCCCCAATAGTCATCAAAACAACATTCCTGAGAGCTGCAG
 G  E  E  E  D  D  E  V  K  Y  P  P  I  V  I  K  T  T  F  P  E  E  L  Q

AGATTATGCCCCAGACAGAAATGTCCACACTATCATTCTAGACTTCACACAAGTCAATTTATCGACTCTGTTGGAGTAAAACCCTG
 R  F  M  P  Q  T  E  N  V  H  T  I  I  L  D  F  T  Q  V  N  F  I  D  S  V  G  V  K  T  L

GCTGTGATGGTGAAGGAATACGGAGATGTTGGTATTTATGTGTACTTAGCAGGATGCAGCCCACAAGTTGGTGAATGACCTCACCGCAAC
 A  V  M  V  K  E  Y  G  D  V  G  I  Y  V  Y  L  A  G  C  S  P  Q  V  V  N  D  L  T  R  N

CGTTTCTTTGAAAATCCTGCCTTAAAAGAGCTTCTGTTCCACAGTATCCATGATGCAGTCTTGGGCAGCCATGTTGAGAGGCAATGCT
 R  F  F  E  N  P  A  L  K  E  L  L  F  H  S  I  H  D  A  V  L  G  S  H  V  R  E  A  M  A

GAGCAAGAAGCCTCAGCCCCACCTCCCCAGGACGACATGGAGCCCAATGAACCGAGGCATAA
 E  Q  E  A  S  A  P  P  P  Q  D  D  M  E  P  N  A  T  P  T  T  P  E  A  *
```

CTGTCATTGTAGTACATCAAAAAGGTATTAGAATAACTAGTGTCTTTAAAATGACTAGTAATACAATACATTTCTGTAATGACTTTGTGTGT
GTGTGTGTGTGTGTGTGGGATATGTCTTGTCTGTTCTGTTGCCCTAGCTGAGTGCAGTGGATCATAGCTCACTGTAACCTCCAACCACTGGCT
CGAGTGATTCTTGTGCCTCAGCTTCGTGTCCTGAGCAGCTAGGACTACAAGTACATGCCACCACAGCCCCAGCTAATTTTTTTTTTTTTGTAGAGA
TAGGGGTCTTGCTATGTTGCCCAGGATGGTCTTGAACTCTGGACCTCGAGATCCTTCCTCCTTGGCCTCCCAAAGTGCTGGGATTACAGGTGTTG
CAATAGAGATACATCAATTGATATTGCTTTGCCTTTCTCTGAGTGTCTATTAATTATTATGTCTTCATCCTATATGAATCAAGTATTCAGT
TTAAAATATTTGAGAGTCCCTCCTTAATTTTTTGAGGATTTAGGAAGTTCCAACAGGACTAATGTAGTATAGGCATATGAAGTCAGAGACACAAGAAAA
TAGAAGATACACTGGAAAAAAATAGATGGAGAAAAAATGGCTCAATGCACATAATAGCCATGGAGTAAGATAAAGAGGAAGGGAGAGACAGCTGA
AGGGAAGGAGAGAGAGAACTGTGCAACATAAAAGGAGAGTAGGGCAGAGTGCCCTATTTGAGCTTTCTATT
TACAAGGGTAGGGAGACTGAAATCCAGATTACATATATAAGTGGTGTAAAAGTAATTGCGTTTTGCCATTAAAAGAATTG
GCATTAAAAGTAATTCCTTTTTTTTTTTTTGAGACAGAATCTGTTCTGTCGCCCACAGTGCAGTGGCTTTTATTTTATTTTTTTATAGAGACAAGG
GCGATTATTATTCTCAGCCCTCCCAAGTAGCTCGGATTACAGGTGTGCACTACACAGGTTACACGACTGGCTCTTCCTCAGGTTCA
TTTTGCCGTGTTGGCCAGGCTAGTCTGGAGCTCCTGGCCTCAAGTGATCCTCCCAGCCTCCAAAGTGTGGATTATAGGCATG
GTTCCACTGACCCGGCCTGCAATTACTTTGCACCAGCCTAATAGTTACATTTCTGCTATGTCCAACATTTCAGGATTTTATCTATCTCAAG
TAATCATACTTGAATAAAGGTCTTTGCAAAGATAAAGTCTTTGAGGCCCCAAATGCAAATGACCCACTTTCCTACTTTCCTTTCCTTAAATATCATGAATATGTATAGTT
GTCTGACTAACCATTCTCCCGTGGAGCATTGTGTCTCGGGAGGAGAGAGTAAAAACTCCAGTTTCTTCTTCATGGAAGTGCCAATAGAGGTGAAGGATGAATTGAAAGATGAAGGATGCAATATGGCATAATATGCATATGCATATTATTCTCTTGA
CTGTATAAGAGTTCTGGGGAGGAGAGAGAGAGTAAAAACTCCAGTTCTTCTTCATGGAAGTGCCAATAGAGGTGAAGGATGAATTGAAAGATGAAGGATGCAATATGGCATAATATGCATATTATTCTCTTGA
CTGTCCTTACAGCATTAGGTAAAAAACTCCAGTTATTCTCTTGAACTGACAGATAAATCCAATGTGAGAAATCAAACTTTGACAGATTCCTTAAATGCTCTACTAGCTTCTGCTTACAC
GGAAAATTGGAAGCAATATGCATATATTTATTTAACTGGATAATGCATAAATCCAAGTGAGAAATCAAACTTTGACAGATTATAAATGGTAGTATAATGATT
TTTAGGATGATTGATTTTTAAAATGTAATTGCTAGTCTAGTCTTAGTAACTAGCACGCGAAAAGTTCTGATACACTTTGTCATACACTTTGTGACAC
ACCGTACTTTTAAAAATGTAAATGCTAGTCTAGTCTTAGTAACTAGCACGCGAAAAGTTCTGATACACTTTGTCAGCCAGTGCATTAAGTATATTCTGTGACAC
ATTAATTACTAAAGAACTAAATTATTTCGGTATTGAAGATTATAAACCACTGGCAAATAAACCTAACAGCTAACAGCTAACATTGTTAAGCCATTGATTATGAATGGTCTTAACATGATTATTATTGAATGCT
CAGTGGACATTTCAAAAGCAGCCAACTTGAAGATTTGAAGATTTATAAACCACTGGCAAATAAACCTAACAGCTAACATTGTTGAGCAGGAGTATGGCTAGGCACT
CTTATATAAATGCTTTCATGTGCTAATCTATCTGAAGACAGCAGAAAAATGGCTCACAGGAAAAATGGCTCACAGGAGAAAAATGTTCTCTCATCA
TCAAAAGTGTCCACCAATTGCTGGGATTGATTTCTGCTCACCCAGTGCCACTGAGCACGCTCCACCCAGAGACCACAT

FIG. 9C

TCCATTGCTGATCACAAAAGGCTGCCACCAGCGAAGTCGAGTTGTGTTGGTGAGGCATCTTCAGGAAGAAGTATGTAGTCGTGTCTCAACAGAAATGT
ATTTCTGGTAATCCATCTCGATGAGCAAGTCCAGTAATTCCTATAATAACAATATACCAACATAGCAATATATCTAGAATCTCCTGCCTCTCAT
AAACCACCAGTATACTTCAGATACTGTGAACTTCCCAAGAAATTTCAGCCAGGAAATGACAACTGATTTCCTGACTTTGATATTAGTATTCACT
ACTTATACTGTTTCTGTATGAGGCTAATGATATGAGGGAAGGATATTTGAAAGAGTTGGCCAAAATAAAACACTGAAGTAAAATAAGTTATGTT
TTGCTTTAAATTTAGTTCTCAAATTTCTATTCTTACAAATAATGAGATACACCCATGTTTTACATGTTTCTCAGGCAATAGCTTTCAGTATTAAAAT
AGTTATTGTAATTTTATGCAATGGACTGGTATAAAGTTTATCTCTCTGTGATAAGATTGCAGGTGGGATGTTAATTACTTAAG
AAAACATCCTTCAAATACCTTAAATACTTTAGGTCATCTGTTAATCAGCTAGTTATTAAGAATGATATCTATCTGCTAAAGCAGATTTTTCTAAAG
ACACCATGGTATTACTGGTCTGGTTTTAGCTACTTCAGAATAACAAAACAGAATTCTATTACACATAACTCATTAAAATATTCATGAAATCACAAAATCACAAAATCAGACTTTTT
TTTCACAATTTGAAATCATACAAATGTATTTCTTAATTGTATCACTCAAGCTTCAGTAAGCGTAGAGTTGTTTTCTTTATTCATAAAGTTTGACTTT
TTTACTTGAAATCATACAAATGTATTTCTTAATTGTATCACTCAAGCTTCAGTAAGCGTAGAGTTGTTTCTTATTCATAAAGTTTGACTTT
ATTTTAATGTGATTTCTCTCTCCTTTTGCATAACAGAAGTTGCAGAGACTTTCTGCATAACAGAAGTTGGAATCTGCTCAAGGGGTGTTTTC
AGTTTCCACAATTCAAACTGTGAAGTCAGCAAAGCTTTGCAGACTTTCTCAGAGACTTTGGAATCTGCTCCAAGGGGTGTTTTC
ACCCCTGACACATGCCTCCATCGGTAGAGTAGTCCAACGTGAATGCAAGCACATTTTATCCATCAGAATAATTCATTAGAACAACAATAATCACTACTGATAATTC
ATGGGCCCCCAGTATTGCAAGAACCTGACCAATTGCTATGGTGCAATAACAAAAATTCACTACTTGCACTCAAGTACCTGAAGATCCAAAT
TTCCATACAAGTGTCCTTGCTTGGACCAATTGCTATGGTGCAATAACAAAAATTCACTACTTGCACTCAAGTACCTGAAGATCCAAAT
CTTGTGTAACGCTTGCTCCAGTGAATGCCCAAAATAGAGTGCAGTGTCCTGGCAAGAATTCACACTCAGTGCAAGTACTTCCACCTTCTAAG
GACATCCATAAGTCAGTTGATTCTTCTACGTCAGATGAAAGCGTCCTTCAGAAGTCTCGAGAAATAAGCCAGATGTGGTAAAAAACAATTC
AGATAACTATGGAATATTTAAGACAAATACAGAGTGATGTCTTGGACTTAAAAAATCATTAAACTGCCCAAATAATTGGAAATTGAAATTAAAAAGG
CTATTCCACAATCTTTTTTTCCTGCCGTATATTGAAAATCATTAAACTGCTCAAATAATGTCTAACAGTGGCACATGCAGCCCTCGCTCCGGGGT
TATATCAATTTTTTTTGAGACGAAGTCTGCTCGTGTATATTGAAAATCATTAAACTGCTCAAATAATGTCTAACAGTGGCACATGCAGCCCTCGCTCCGGGGT
TCAAGCAATTCTCATGCCTCTGCCTCTCGAGTAGCTGGATTACAGGTGTGCCACCACCTGCTATTTTTGTATTTTCATAGAGATGGGTT
TCACCATGTTGGCTAGGCTGGTCTGCAACTCCTGACCTCAAGTGATCGCCCCACCTCGGCCTCCCAAAGTGCTGAATTACAGGTCTGAGCCACCATG
CCTGGCCATATTAGTAACACTTCTATTGTAAAAGTTAGTTATTAAGCATATACCCCAAACATGTATATTGTTTATATAGTATATAAAA
AGTATTATTGTAAATGTATTTATTATGAAACATGCAAAAGGAATTTGAAAGCCAATAAGATAAATATAACATGCAATCCAGCACTTTCCCCTGAC

GTCAGCATACACACAGCCCTCAGGCGGTCGGGAGGCAGCATTTCTGAATTCCCTGAAGACAATCAATATTCTCAGAGTAACTATGCTAATTAGAAAA
CAATTTGAAAGGGTTATATTAAAGGACATTTCTTTGAGATTTAATTCATCTTGTTCTCTGTCTTCTCGGGGAGAAAAACAAGCCTCATAAT
TATCCTTATATATTAAAATATGCCATACTATTTTGGTTAAAGAATCCAAAGTACATGAAGGAGAACTTCTGGGTGATAAAAGTTCTGTATCTGTTT
TATGTGGTGGTTACATGGGTTACACAACTAAAAACTCATTGATCTGAACAATTAAGACATCATTCACCCAGATCATCCATTTACCTCATTATTAC
AAAAAGAGAAATGGGAGGAGAGAAAATGAGTCTGTATGAGTGTCCCAGCATCATGGTGGGTCCCCAGCATCATTCACCCAGATAATCATGAAATAATCATTTCC
TAACTCAACTATTGAGTGCTAATTGTACCAGTGGATGCAAGGTGCCCATCTCATGTTCAATAGCAAAACAGCCTGAGAGCTGAGTATGCCCAGTGCC
GGACGTAAGTACGGAAGCATCCGCCCCAGTTCTCTCGGCCTGCCATCTCAATGTTCAATAGCAAAACAGCCTGAGAGCTGAGTATGCCCAGTGCC
GTGGACAGCAGATAATTCTCTTAAGAGGATAAGGAGGAAACGCTGTCCCTGAAGACACCGTTCAACTTACAAATCAACCAGCCTAGAGTTCACTTATCT
TTGGATTCGTTCATTATAGATATAACAAATTCGAGCTGGTTTGAATTGGTTTCGTTCCTTGCAGCTGAAAGCATCCTGATTTAATTCCTTAGTA
TGTTAATTGAATAAGCTCTTTAGATACATTCCAGAAACCCTGAGTGGTAATAATCTGATTCAGATCTATCTAGGTGCACCTGTTATTTCTTTGTATCT
ACTTATTCAAAGACTCTTTATGTTTCAACAGAAATCTTTTGAATTGCCTTAAATACAAACTTTGCAGAGACTTTGCAGAGGTCCACAGTCTACAAGGTTGAGAA
GTCCAGGCTAATTACCTCTCCTGGCTCGTCTCATGATGGCAATAATGGAATATATAGGAATAAGTCACAGTCCACAGTCTACAAGGTTGAGAA
GTTAGGATTGCTCCTGGCTCGTCTCATCATGATGGCAATAATGGAATATATAGGAATAAGTCACAGTCCACAGTCTACAAGGTTGAGAA
GGTAGGGTACACCTTTCATCTGGCTCCAAGGCCATCACTATTGCTCTTGTTCCATTTAAGATACTGAGGTTTAGAAAATAAGAGTCTGCAAAGCC
CATATTGCCAAGTCTGAGATTACAAATTGAGGTCATGATGACATAATTCAGGCATGAAGTGTACCTAATGATGAAAGTAACCAATTAGAGAACCTTAGAGTTAGG
GAGAAAGAACACTTACTACTTTCCCACTACAAGCTTTCAGGAAGTGGGTAGGTGATCCTTTCCACCCTTTAGTTGGAAAGAATACAGATGCTTGAACCAGGCTTTGT
TTTAGTTTTCTACTTGGGTCAGCAGCAAGCACTGAGGACCAGATAATTCCAACTCACACCAAGTCAGTAGAATACTGCACATGAATTGATTCTG
CTTCCAGAGCATTTGGGTCAGCAGCAAGCACTGAGGACCAGATAATTCCAACTCACACCAAGTCAGTAGAATACTGCACATGAATTGATTCTG
GCCAATTTTTTCAGACACACCTTACATCCAACTGAGATCTAATAAACAGAAGATCAAGTATTAAAACTATAGATATGATTCTTCTCCAAGA
CTTGGCAGCAAAAGCTGCAGGTGACACTTGATATGACATCCATCCGTATTTCATTATTGTTCTGCTAATGGACAGAGAAA
GTCACCATGATTGCCCCAGGTGACAAATTATAGAAAGTGCCAAATGTGTAGTTGGGGGTTGAGAGAAACTCAGACCCGTGCTTCTGCCATGCT
GGCTGAATGCCTTGAAGGCCTGGGCTCACTCCTACAAACTGTTAGTTGTGCATTTCTATTTGGCAGAATACTTAACCAGAAGAA
TAGCTAACAGCTTTACCAATTTTACTATTTTGTTGTAATTAGACTCTCAATACAACACTTTCAAGACAAGTAAGATTGAAATAATAACTGAAGG

FIG. 9F

TAGTTTAAACAAGGCACAGCACCCTTGGTTGATGGTGATAGCCATGATGATGTGACACTGCTGTTAATACAGTGGGATTTAGTAGACAGAATAAATTGT
TCACATAAAATCTTGCCTAAATATTAGCCAAAAATTGATGTTGACATTAATGCCTTGTTTTCTATAAATTTTTTCTCCAGAACACATC
CAAATGTTCTTGTAAAAAAAAAAAAAAAAAAACTAGAGGCTGGGGTGCCATGCTCACGCCTGTAATCCCAGCACTTTGGGAGGCCGAGACGG
GTGGATCACGAGGTCAGGAGTTTGAGACCAGCCTGACCAACATGGTGAAACCCTGTCTACTAAAAATACAAAAATTAGCTGGGCATGGTGGCGTGC
ACCTGTAATCCCAGCTACTCAGGAGGCTGAGGCAGGAGAATGTCTGAACCGGGAGGTTGCAGTGAGCCAAGATTACCCACTGCACTCTA
GCCTGGGCAACAAGAGCAAGACTCCGTCTCAGAAAAAAAAGTCTATTTCACCTAAATTTCTAAGTTATAGTTATAGATGAGAGATGGTAAGAG
GAAAAAAAGTAGAAATAACCATTATAGCTTTAATTTTCTCTTGTTGAAACAAATTGCTTAAGTCATAATGATTTACTCTTATAAAGTTATATCAGTATCC
TACATTTTATTGTTGATATTTTATCAGTATTCATCCTGAGCAGGAACACATTTACTCTTATAAAGTTTCAGCTTGAGAGACAGCTGGCAA
GATGGCTGAATAGAGAACAGCTCCAGTCTGCAGGAATCAATGCAGAAGGTGGTGCATTCCAACTGAGGAACCCGGTTCATC
TCATTGGGACTGGTTGGACAGTGGGTGCAGCAGTGGGTTGCAGCCAAGGGTGCAGAACCACAAGGGTCGGGGATTTCCCTTTCCTAG
CCAAGGGAAGCCGTGAGTGCAACTGTGCTCGGGAGGAACAGTGCAATCTGGCCCAGATCTTTGCAACAGTCTTTGCAACTGGCAGACA
TTCCCTTCGGGTGCCTGGCTCAGTGAGTTCCCACACCCCAGGAGCCCAGGAGTAAGATTCACTGCCTTGAAATTCTCGGCTGCCACACACAGCAGTCTGA
GGTCGAACTGGGATGCTCGAGCTTGGTTGGGAGGCCTCCATTACTGAGGCTTGAGTAGGCCGTTTTCCCTTCACTGTGTAAACAGAGCCAC
CCAGAAGTTTGAAATGGGTGAAATTGGGAGCCCGCCTCAGCTGCAAGCCAACTGCTAGATTCCTCTCGGGCCATCTCGAGGCATCTCGAAAAAAGGC
AGCAGCCCCAGTCAGGGACTTATAGAGATAAAACTTCCATCTCCCTGGATAGAGCTCCCTGGGAAGGTCGTGGGGAAGCTTCAGCAGACTTAA
ACGTCCCTGCTTGACAGCTCTGAAGAGAGCAGCGGGTTTCTCAGCAGCGATTTGAGCTCTGATAAGGACACAGCCTGCCTCTCAAGTGAAACCCTGA
CCCCTGTGTATCCTGATTGGGAGACAGGAACAGGCCAGCAATCTTTGCTGTTGCTGTTCGTGTTGTGGTGATACCTGGGCATCTGTGGTGCCCCTCTCGG
ATGAAGCTTCCAGAGGAAGAACAGGCAGGGCAGCAGTCTTGCGCTGTAGCCTCGTTGGGATACAGAAACAGGGTCTGGAGTGAGGTCTCCAGC
AAACTGCAGGAGACCTGCAGCAGAGGGCCCTGACTGCCAGAGGAAAACTAACAACAGAAACTAATCAATACCAACAAAAAGGAGGTCACT
CATAGACCCATCCTAAAGTCACCACATCAAAGACCAAGTAGATAAAATCCACAAGCAGCCAAAAACCGCCAAAAGCTGAAATTCCAAA
AGCCCAGAAAATTCCAAAAGCCAGAATCCCTCTTCTCCCAAAGATCACAACTCCCTCCAAGCTAAAGGATCCAGCATGCAAGGAATGAGATCAAGGAAGCTATAAGAACCTT
AAATTGACAGAAGTAGGCTTCAGAAGGTGGTAATAACAGTTTAGAGAAGAATAATAAATGACCTGATGGAGCTGAAAAACACGACGAACTTGTGA
AGCATACAAGTATCAATAGCCGAATCGATCAAGTGGAGGAAGAATATCAGAGAATGAAGATCAATCAATGAAATAAAGTGGAAGACAACATTA

FIG. 9G

```
GAGAAAAAGAGTGAAAAGAACAAGCCTCCAAGAAGAAATATGGACTACGTGAAAAGACCAAATCTATGTTTCATCAGTGTATCTGAAAGTGATGGGG
AGAATGGAACCAAGTTGAAAACACTCTTCAGGATATTATCAGAGAACTTCCCAACTAGCAAGGCAGGCCAACATTCAAATTCAGGAAATACAG
AGAACGCCACAAAGATACATAATCGTCAGATTCACCAAGGTTGAAATGAAGGAAAAAATGTTAAGGGCAAGGCAAGAGAAAGGTCGGGTTACCCACAA
AGGGAAGCCCATCAGACTAACGCAGATCTCCCTGCAGAAACCTACAGAAGAGTGGAAGCCAATATTCAACATTCTTAAAGAAAAGAGTT
TTCAATCCAGAATTTCATATCCAGAGAGTCCTGAAGAACTTCATAAGCGAAGATAAAATCCTTTACAGACAAGCAAATGTGAGAGATTTTTGTCAC
CACCAGGCCTGCCTTACAGGAGCTCCTGAAGGAAGCACTAAACATGAAAACCAGTACCAGCCAGTCAAAAACATACCAAATGTAAAGAC
CATTGATGCTTTTGATAAACTGCATAAATGGGCAAAATAACCAGCTAGCATCATAATGACAGGATCAAATTCACACATAACAATATTAACCTTAA
ATGTAAATGGCTAAATGCCCAATTTATCAGCAACAACCAGAACACAACTAGCAAACGGAAAGCACACAACAGGGCTGCAATCCTAGTCTCTGATAAAACACTTAAACCAACAA
AGGTCAAAGAGACAAGAGCTGCATTACATAATGGTAAAGGAATCAACAGAGCTAGCTGTTCTAAATATATATGCACCAATACAGAG
GACCCAGATTCATAAGCTAACTTCTTAGAGACTTGGAAGTCCCACAACTAGAAGGATCTACGGACCTAATAATGGAGATTTTTAACACCGCACTGTCAATATT
AGATCAACGAGACAGAAATTAACAAGGATATCTAGGACCATCTCAAAATTGACCATATATAAGGATTGAAGTAAAACTCTCAGCAAATGCAAAGA
AATCAACAGAATATACATAACAACTGTCTCGAGACCACAGTGCAATCAAATTAGAACTCAGATTAGAAACTCACAATCTACACTACATGGAAACT
GCGGAAATCGTCCTGAATGACTACTGGGTACATAACGAAATGAAGGCAGAAATAAGATGTTCTTGAACAATGAGAACAAGACACACATACC
GAACAATCTCTGGACACATTTAAAGCAGAGACAGAGCAAAACACATTCAAAGCTGGTTTTTGAAAGATCAGAGCGAACTGAAGGAGAT
ACATCAAAATTAAAGAACTAGAAGACTAGAGAACAATGAATCCAGAAGCTGGTTTTTGAAAAGATCAGAGCCACTAGTGAGACGAATAAGG
AGAGACACAAAATACCCTTCAAAAATCAAAAATCAATGAATCAAATAAAATGATAAGGGATATCACCATGATCCAGAATATCACAAAAGATACAGAGATACTA
AAGAAAAGAGAAGGATCAAATAGAACGCAAATAAACTAGAAGAAATGATAAGGGATATCCACTGATCCCAAGACTAAGCCAGAAGAAGTCGAAT
TAAACACCTCTATGCAATAAACTAGAAGAAATGATAAATTCCTCGACACATACACCCCAAAAAAAGCCCAGGACCAGGTGATTCACAGCTGTATTC
CCCTTGAATAGACCATAACAATTCTGAAATTCAGAGCAGTAATTAATCCTACTAAACAAAACAATGAAAAGAGGGAATCCCCTAACTCATTTATGAGGCAG
TACCAGAGGTACAAACAGAGCTGGTACCATTCCTTCTAAAACTATTCCGAACAATGACAAATTTCAGGCCAATATCCCTTATGAATATGATGTGAAAATCCTTGATAAAA
CATCATCCTGCTACCAAACCTGCCAGAGACACCACAAAAAAAGAAAATTTCATCCCCTTATGATCACACCAAATCAATAACATAATCAACATAT
TACTGGCAAACCAAATCCAACCAAGATCAAGTTGGCTTCATCCCTGGATACCAGGCTGTTCAGCATGACAGGCTGTTCAGCATGATAAATAAACATAATCAACATAT
```

FIG. 9H

```
AATGACAAAAATGCCATGATTATCTCAATAGATGCAGAAAAGGCCTTGCCCAATATTCAGTAGCCCTTCATGTTAAAAACTCAATAACTAGTATTG
ATGAACATATCTCAAATAATAAGAGCTATTTATGACAAATCCACAGCCAATATCATACTGAATGGCCAAAACTGAAGCATTCCCTTTGAAATA
GGCACAAGACAAGATGCCCTCTCTTAGCTCTCTCTTATTCAACACAGTATTGGAAATTCGGCCAGGCAATCAGGCAAGGAAAGAAATAAAGG
GTATTCAGTTAGGAAAGAGGAAGTCAAATTGTCTCTGTTGCAGATGACATGATTGTGTATTTAGAAAACCCATGCTCAGCCAAAATCTCCTT
AAGCTGATAAGCAACTTCAGCAAGTCTCAGGATACAAAAATCAATGTGCAAAAATCACAAGCATTTCGTACACCAATAACAGAGAGTCAATCATG
AGTGAACTCCATTCACAATTGCTACAAGAGAGAATATACAACTTAGGATGAAAACAACAATTCTAAGGATGTAAGGAGACCTCTTCAAGGAGAGCTACAA
ACCACTGCTCAAGGAAATAAGAGAGGATGCAAACAAACAATTCTATGCCCATGGTTAGGAAGAACCAATATGTGAAAATGCCATA
CTGCCCAAAGTAATTATAGATTCAATGTCCATCCCATGGAAAACATTCTTCCTCACAGAATTGGAAAAACTGGGAAAATTCACATGAACC
AGAAAAGAGCCTGTATAGCCAAGACAATCCTAAGCAAAGAACAAACCTGAGCCATCATGCTACCTGACTTCAAGTATACTATAGGCAACAGTA
ACAAAACGCATGGTACTGCTGTACCAAAGTAATATAGACCAATCAAACGAACAGAGGCCTCAGAAATACACCACATCTACAACCATCTTGA
TCTTTGACAAACCTGACAAAACAGCAATGGGGAAAGGATTCCCTATTTAATAATGGTCTAGCCATATGCAATAAAAGCTAAAAGAAACT
CTTGGATCCCTTCCTTACACCTTATTCAAAGACATAAGCCAAGATCAAGATGGATTAAAGATTTAAAATGTTAAGACCTAAGATGCAACAATGGCAACAATGGATCTA
CAGGCAATACCATTCAGAGACATAAGCCAAAGAACTTAAGTAGAGGAAGAACATTTTACAAGAACATTCAAAAAATGGGAGAAAAATTGCAATCTATCATCTGACAAGGC
ATTAAACTAAAGAGCTCCTGCACAAGAACCTTAAAGACACAGATGAAATTTACAAGAGAAAATCTTAAAAAGTGCAAGGATATGCAACAACATGAAGGAGATATCCACACCAGT
TAATATCCAGAATCTACAAAGAACACTTGAAAAGTCAGGAAACAACAGATGGGCCTGTGTGAGGGGCTGTGAGGGAGAAATAGGAAGCCTTTTACACTGTTGGTGGAGTGTAAGTAG
ACATTTATGTGGCCATCATTAAAAAGTCAGGAAGACAGTGTGGCAATTCCTCAAGATCTAGAACACAGAAATACCATTGCACCCAGCAATCCATTACTGGTATATACCCAAAG
TAGAATGCCAATATGTTGGAAGACAGTGTTGGGAACAGCACCACCAGGAATACACATTGCACCCAGCAATCCATTACTGGTATATACCCAAAG
TGCAACCATGGTTGAAGACAGTGTGGCAATTCCTCAAGATCTAGAACACAGAAATACCATTGCACCCAGCAATCCATTACTGGTATATACCCAAAG
GATTATAAATCATTCTACTATAAATAATGCACCTATAATGCACATATCATGAATATACACCATGTTCAACAATAGCACAAGACTTGAACCAACAAATGCCATCA
ATGATAGACTGATAAAGAATGTGGCACATATACCATGGAATACTATGCAGCATAAAAAGAATGAGTTCATGTCCTTTGCAGGACATGGATG
AAGCTGAAACCATCATTCTCAGCAAATCATGGAACATCAGGCACTGGGGAGGATACCATAGGAGAAATACCTAATGTTCTCACTAGTGGGAGTTGAACATGAGAACACA
TCGCCACAGGGAGAGAACCATCATGGCACTGGGGGCTGTCGGGAGTGGAGTGGAGTGTCCGTCGTGGGGAGAGCCTGTCCGTCGTGCGCACGTGTCTCGCACCTGTATACCTATTGTAACAACCTGCATGTTCGCACGTATAGTGAAATACCTAATGTAGTAGAAATAATGA
GGGTCGCAGCAAACCACCATGGCCACATGTATACCTATTGTAACAACCTGCATGTTCGCACGTATAGTGAAGAATATGTAGAAATACCTAATGAT
AAAAAAAGTTTCAACTTGAACTTGAAATAGTTCAGAAATAAAATACTTTTAATCATTAAGCAATGTATAGTTGAGTTGATATATTAATAGTTTAATTTTACT
```

FIG. 9I

TTTCAAAGTATATACTAAGTCAATGAAATATTAGATCATCTTTCTCTGATATTTTGTTATATTGCTAATGTATGGTTGTTATATAATCAAGATC
ATAACATTCACCTTGAATTGCATAATCCAGCCTTCAGTGGGAGTCAGGTCAGTCATGGTCACTGCATACACCTCCGTCCATCATGACTGCCACAGAGCA
TCACCATCAGGGAGTCACAGAATCTTTCTACTGTACAATCATCATGAATAGCCAGTGCTCATTCACTTAAACAAAAAAACAAAATTTATGAC
AAATTGTGACAAAATACTTGAAGCAAATTTCACTTAAGCAACATAATTATTTAAGTAGAAACTGCTCATATTATATACTCTATAGAC
AAAACACTAATATAAATACATTGTTTCAGGAACATAAATACTAGGAGGATTGAGATATATGCCCTTTGTCTGATATTAGTACACACACCATAGAT
ATTAGTCTACACATGAAAAAAAGTATATATGTACACATGTAAATGAAAATCAAAAGAAAATACAATAATTTTTGACAGATATTTAACTTTTTAGATAG
CATATAAAGAAGTAGAGATGATTTTTAATTTTTAAAAATTTTACAGTGTCTGTTTATTAGGAAAGAATCATGAAGAATCACAATCCACTGGGC
TGGTCATTTTATTTTATTTTTTTAATACCGATAGGAATAGACAAAATGACACACATTTAAAACATCTGAAAGTATTATCTGGGTAACTAAAAGCTTGTA
ATGAATTTTTATGCTTTATCAAGATCTGAAAGGCTGAAGTGGAGGATGCTTGAGGCCAGCCTGACACATAGTGAGATCCAGTGTTAAAAAAATTAGCTGAGT
ATCCCAGCACTTTGAAAGGCTGAAAGGCTGAAAGGTGGAGGATGCTGAGGCCAGCCTGACACATAGTGCAACATAGTGAGATCCAGTGTTAAAAAAATTAGCTGAGT
GGTGGTGCAGGCCCATAGTCTCAGCTACTTGAGGGCCTGAGTTCAGGCCTGAGTTGTGATTGTGCCACTGACTCCAGCCT
GGGCCAGCAGAGTCAGACCCTGTGTCTCTGAAAATTGTTTAAAATGAAAAATTGATCTGACTCTGGAAAATATGCACAACCCATGATACTATCA
CCACAAGCAGGCACCAAATCGATCATTCAAAATTCCTTGTATTCTTGTGTGTGTATTCTTTGIGTGIGGTTTTGTTGGGGGTTGCTGTTTA
GAACACCCAACAGAGACATATCCTTAACATATGTTCAGTGCACAATATAATCCTGTCAACCATAGACATATGTCATACAGCAGATCTCTAGAAC
TTATTCTTTTGCATGAGAAACTTATAGCTACTGAAAAGTATTCATTTCCCCTTTCTCCAGATCCTATAATGTTAAATTGTTAATTGGCCAAAA
AAATGATTTTGAGTTTAAGAAATGAGTTTATAACAAACTGTTATAAAGCTAATTTATAACGTTGAATAATACTGTTATAAATTACCTTGTAATGTCTTAATATTGATTA
GTAAAATAAAATCTTATTAAATAGATATTCTGGATAGATATTTCTTTAATAAGTCTTGACTCCTAAACCTGATAACCAGTTAACACTTTGGAGAAATGTACT
TTTATGTATGGATATTCAAGTATTCTGGATAGATATTTCTTTAATAAGTCTTGACTCCTAAACCTGATAACCAGTTAACACTTTGATTAATGCAGAAGTATGATTAATCAGTTGTT
CATCAAGATACTACTGAAGAAATAGATTTGAAGGTGTCTAAGAAAAAACTTAAGTAGAACATATAAGTAGAACTAATGCAGCACACATCTGTGTGTT
GATCCTCTCTCTCTTCTCTTCTCTAACCCTCCCTCCACAGTTCCTTTCTCTTCTCTGAAGAGATGATTTTACATTAATTTTATCCAGA
AAGTTAGAAATTAAACATATCCATAATATATGTTGCATTCATTCACGTATGCTTGATTTATAGTCCAATCTTTTCTAAAGTCTTCTGCT
AGTCCCAGCATTCCAGGGAAGCTGAACTGAACAGGTGCAGCCGGAGGCTTGAGCCACTATGGAAGCAGCACGTTGATGCCTCAGAGATCCAGAGAAAG
ACCAGATAACTATAATTCAGCCCTTCACCCATATTGTGTCTTTTGATTTGTCTGAGTATATATGCCGCACAACAGCAGCTATCTCTGAGATTCAA
ATAGTTACTGCAATTCCATTATCTGTTTTTTACTGTGTGAGGGATTTGGAGCCACATTTAGTCGTGAGCCTACATCCTACATCACAGATACAGAGACTCAAGAGTCAAAGTGC

```
TAGGAAATGATGGGAAGGGTGTGGGAAGAACCCTTGTGTCAAATATCTTCTCTGAGTAAAAGATTACAACCAGCCATAGAATAATGTATGTCACAT
GGTTGGGTGAGGAAGGAAGGACATAAGCTAAAATAATTTTCAAAAACCACGATTAACTGGCTTAATTTATGAAGTCTCAGTAGTCACTAAATTGGGGAAA
TAGAAATGTGAACAGATTCAAGTATCCCAGAACTCCCAATTGGTTCGTGTCTCGGGCAGGCTTTAGAGGGACTGCAGGTCACAGTTTTTGCATACCTGGTGGG
TATCTGTAGGCCTAGAGTATATGCACTTGGTAGACATAAGCCAATGACTGAACTGTTTTTCTGTCACCTAGCTTGGCTTCTGCTTCTCCTTCCCTTGG
CACCTTGTTTCACTCTGTTCCATGAGTGCTGGCAAGTGACTTGGGTATGGACACTGGATTGTGGAGGACACATTGAGTTCTGCTGAGGGTAC
CAGGTCCATTATCAGTTGTCGTGTGGTGCAGACCACTGATCTATCCCGTCTCACTCACAGGACTGTATCATATTGTAAAATGTATATATCATAGAAAATGTCATG
TGAGAACCATGGCTAGCAAGCCCAGCATGCTAATCTATCCCGTCTCACTCACAGGACTGTATCATATTGTAAAATGTATATATCATAGAAAATGTCATG
CTGAATTAGCTAGAAATAAGGTCTAAAATGCCCTTTAATCACAATTATACATGAAAACCAGGAACATATCAACCTCTTGAATTTATATTCATAACTTC
ATAAAAATCTGTTGGGAAGATAATGTCCTTAGATTTACACTCGGCTCACTCGGATAGTGCAACTCGGGTGCAAGCAATTCTCCTGCCTCAGCCCTCCGAGTAGCTGGATT
CCACGCTGAGTACAGTGGTACAACATCGGCTCACTGCAACCTCGGGGTGCAAGCAATTCTCCTGCCTCAGCCTCCCGAGTACTCACTCGTTGC
ACAGGGGCATGCCAACATGCCTCGATAATTTGTATTTTTGTAGTAGACATAGACCACCACCATGCCCAGCTAATCTTTTATTTTATAATTTTTTAATCTATGCTAATC
GGTGATCCAAGCTCAGCCTCAAGGATGCATTACCTGACAGTGGATTTGCAGAACTCCAGAAGAGCAAGACAACCAGTCCAAGTTCATCCATGAGCCCTTA
TACCTCCCTTTAGAGGCATACCTCAAGGATGCATTAGTTCTGTGCTTTCCTTGAGGTAGAGTATTCACATTAAAGATTCATTATATATAATTTGTTTATACAGTATCTCCATGTTGATTTA
AACTGAGGGCTTCAGTGACAGTTTAGTTCTGTGCTTTCCTTGAGGTAGAGTATTCACATTAAAGATTCATTATATAATTTGTTTATACAGTATCTCCATGTTGATTGG
TTTTCCTTCCTTTTTTTCTGTGTAGTTCTTCCTTGAGGTAGAGTATTCACATTAAAGATTCATTATATAATTTGTTTATACAGTATCTCCATGTTGATTGG
AGGATGCTTTTAGCTGGATTTATACAACTTGAATTTAAATACTTTTTCTATTATGCCATCATTGTGGCCCCTTTGCGGCTGGACATGGAGACATCACCCTTTATGC
ATCTTAGTCTTAGGGAAGAACAGTGTAGTCTAGAAACAGTGTAGTCTAGAAAGTATCAATCTTAGACCCTCACCTGTGCGGGTACTGGAGCTGGAGACATCACCCTTTATGC
AGAGTCTTTCCGAAGCTATTTACCTGTATTGTTTGACATGTTTACATACATATAGTTTTCTTCCTAATGTTCATACATACATGGCACTCTTGTGAG
ATGTCCTAAACATTTATCTCTATTATTTCTTTGACATGTTTACATGTTTACATACTATCCGAAATCTGTCAGTTTCTGATAAGTCATTTTAAAAATCTCTGAATG
GCAAGATCTTTATCTCTATTATTTCTTTGACATGTTTACATGTTTACATCATAATTCCTACCTCAGCACATTTCAGAGAACTAAGATAGTTAG
GAAATTTACCTAAGGCTACTTGAAAGTCTAAATAACCACTCTTCCTTGCACTAAGTTACTCACATCAATTGATTCCCTTCAGAGAACTAAGATAGTTAG
ACAGTTATGCTTTTACCCTGACAGAAACATAACTCTCTTTCCTTGCACTAAGTTAGTCGTTAAGGTTCAGGAACTCACTTGAGGTCTTATA
AATTCCTCCATCAGAGACCAAGGAAACAGTTACTTGCTTGTCTGTTATCCTACTAACAGTTGAGCAGGTACTCGTACCACTTAGCTTCTAG
TTGGATTCCTTTATTGGTGTGCAACTTTAATGCAAGTGGAAGATTTAAAAGTTTTGCTTGTGTGCAAAAACTGCTGGTATTTCCTCCAGTGCCATTCTC
```

FIG. 9L

CCTTTCTTCCTTCCTAATAGGAGCCTTTTCATCCAAGTCCCTTTTCATCCAAGTGACTGGTCGCCCAGAATAAAGACAGCATGTCCAGCCTTCCTTGCATCTGGTGTGGCTAT
GTGGCTAAACTCAATAGCTAATGAATAGTGAATAGAAAGAAGTAGTGCAGCTGTTAGGAAATGTCCTGAAGAGAGAGCACACCCTTCTGCCCAATCTC
CTTCCTATGGACTGTAAAGTTGGGAGCTAGTGGCCCTTTTGGACCATGAAAGTCACATGCTGAGTGGGGCAGAACATAGACAGGAGAAC
CTGGGTCACTGGTCTGCGAGCCACTACAGTAGTCCTGAGTACTTTTTTGGGATGTAATTTACATAGAGAGAGAGAAAATTAAGTAATTTT
GTCTTTCCTGCCATTGACAGCTGAACCTATTCTTAACTGATATATTGAATTTAAATGATCATTTATAGATTCTTTTATTTTACTCAAATTTAGCC
TGTATCTGGCTTGCATGATTAAAGATATTCAGTTTCCTTTTTGTTTTTTTTTTTAAAGATGGGTCTTACTCTGTCACCCAGGCTAGAG
CATAGTGCCACAATCATAGCTTACTGCAGCTCAAACTCCTGAGCTCAAGCAATCCTCTGCCTCAGCTCCCAAGTGATCTGGGACTGAGGCACATG
CCACCACACCAGTAATTTAAGTTTTTTTTTGTAAAAATGTCTTGCTTGCCCAGCGTGTCCTGTATATTTATTTCCTCTTCCTCTTCAG
CTGCCTTGGCTTCCCAAAGTGCTGGATTACAGGTGTGAGCCGCCATGCCCAGCATGTGTTCCTTACCCTCCTACTTTACTGAATATGCTATTTCC
CCTCCCCCTGACCCCTTCTGCCATTCTTCTCTCTCATTCTTGTCTTCTTGCCCTTCAGTACTACTTTTTAAAATGACCCATAGGTTGTGTTTATTCAAG
TTCTTAACAACTCTTTGACATTTCTAATGGTCATAATCATTGCTTCTTCCAGTCCAGTCCAGTACTTTTTTTAAAATCATTTATTGTGTTCTTTGCTTTCCAGTCCAAAATTCTCTAAAA
GTTTTTAAATAAGGAGTTAAAATAATAATCTTAGGCTTCTTAAGGATATTTATTTGTTCCATTTCCAAAGCATTGTGAAATTATATACTAGTTAATTTCTGTGGTTTT
CAGAGTGTACACTATATAAATAATATATTTATTTTCTGTTCCATTTCCAAAGCATTGCTGAAATCTAGTTGTTCTTAAATAAAACCAAACCAGCT
GCACTGGTTTATTCACGTTGGCATTGGGTAGAAATATTCATCTTATTCTGGATGTGAAAACTAGTTGTTCTTAAATAAAACCAAACCAGCT
ATTTATCCAGCTCAGAAACCCTTCTCATTCGAGTCTCAGAACCATCCTCAGCACCGGCATAAGTCTGAGGTCCCCCTGAGTCTCCCGTGACTGATTG
CTGGTAGCAATCTCTGCTGATGTACTCGTTATTAGATAGAATCAAATGAATACAAACCCGGCTTACTGGTGTAATCAGGCACCCATACATGAAGTAAATTGGAT
TTCCAGGTAATGCCTCCATTGACCAGAATATTCCAAGACTGATTGTTGTGAATCAGCACCCATACATGAAGTAAATTGGAT
GAACTCAGCATTAGTGAGTTTAGATCCACAGAGACTAATAATCGACTACAACCCTAAGAAAAGAAGTAAAATAAAAAGTGATAAGGAATCTCG
ATTGCAGATTATAGATTTCTATGATTTTTTTTTTTGAGACAGGGTCTGCTCTGTCACCTGAGGTGCACGTGCACCATCACAGCTCAC
TGCAGCCTTGACCTCCTGGGTTCAAGTGATCCTCCCACCTCAGCCTCCCAAGTAGCTGGGACTACAGGGTACATGCCTCATGCTCAGTTCTAGTTTTTG
TAGAGACAGGGTTTGTTATGTTGTCCAGGCTGGTCTTGAACTCCTGACCTCGTGATCCTGCCTCGGCCTCCCAAAGTGCTGTATTCCATTC
TTTTAATATTATTTGTGATACCAGCCACATAGTATTGTGGCACTGATTTCTTACCCTCTTCTTACTATGCTACGTCTTAGTATTGCCTAGTA
CACAGTAGGTACCCAGCACATGTTTGCTGAACTTTGAAATTTCAGCATTCAAGACTTATTCAGAACAATGTATTCCAAGATAATTTTCTGTTTTT
CTTTTTCCTTTTTTTTAATGTTATTGGGCCAAGTTGAGTTATTGGGCCAAGTGAGTATGCCAGCCCAGGACACACATTCCAAGTTGCCTTGCCTTGGCTGTTTTTTTCAT

FIG. 9M

AAGCAAGATGAGAGCTGGAACTAATATAACTGTCCTTTATTTTATTAAACTATCTCCAGTTATTTCAGACACTATTAGATTTTAAAAATGAATCA
ACCACTAAGAAAATAGCATATTGAGATGACCATTTATTATGATTATTATTAATTTTGAGACAGTCTGCTGGAGTGCAGTGGTGCAGTCTC
GGCTCACTGCAACCTCCATCTCCTGGGTTCAAGTGATTCTCTTGCCTCCGCCTCCCGAGTAGCTGGGACCACAGTGTGTGCTACCACCACCCGGCTAA
TTTTGTATTTTTAGTAGAGACGGGGTTTCACCATGTTGGCCAGGCTGGTCTCGAACTCCTGACCTCAGGTGATCTGCCCACCTGGCCTCCAAAGT
GCTGGGATTACAGGCGTGAGCCACCGCCCGGCCTGTAAATGACTATTTTAATTCACACTTTAAAAATAGCTACATCTGAAATTTATAATTATACA
GATAATCTAATTACTGTAATGTTTTAAATTCACACTTTAGTTCTAAGTGAGGAAAAGTATCCTGAACACTGTATTCTTAATGTTGATATACGATTTTTTAGT
TGAACATATGTGAAAAACTCACTTTTAGTTCTAAGTGAGGAAAAGTATCCTGAACACTGTCAGTGTGCTGATTATAAAAGCTACAT
GCTATATGCCTTCTGCTACTCGAGCTAAAATGTTGTTATTTTTTTTTTTTTTTGAGACGGAGTCTCGCTCTGTCGCCCAGGCTGGAGTGCAGTGGCATGCTAAGGAAA
TAAAGAGCTGGCAGTAATTCTCGCCTCACTGCAAGCTCCGCCTCCCGGGTTCACGCCATTCTCCTGCCTCAGCCTCCCGAGTAGCTGGGACTACAGGCGCCCGCC
CAGTGCGGCCAATCTGGCTCACTGCAAGCTCCGCCTCCCGGGTTCACGCCATTCTCCTGCCTCAGCCTCCCGAGTAGCTGGGACTACAGGCGCCCGCC
ACCGGCCCGGCTAATTTTTTGTATTTTTAGTAGAGACGGGGTTTCACCGTTGTTAGCCAGGATGGTCTCGATCTCCTGACCTCATGATCCACCCG
CCTCGGCCTCCCAAAGTGCTGGGATTACAGGCGTGAGCCACCGCGCCCGGCCAAATTGTTATTTTAAAACATTAATTGTCTATCTAATCATGTAT
ACAAGAATTGTATTTTAAACAGAGTCGCCTTTGGCAGAAAAGTAGAGTGACTATAAATTCCCAAGAAAGTTTCCAAGCTT

```
GCAGTGGCGGCTCCGCCCAGCGCAGCCCCGGGCAGCGCTGGTGGCCGGG
AAGGGCTCATCGTCCCTTTTCCAGCCCTCGGCAGTTTACTGCGGCCCTG
TACCTGGAGCTCTGGCTGGGTGGTCATCTCCTGCCCTTGTGCTGTACGT
TGGATCTAGTGGCCATCCAGAAATGCTTGTCTCCTGCTGTTGGTGAATA
ACTGCAGACCATGGATCATGCTGAAGAAATGAAATCCCTGCAGAGACC
CAGAGGTACTACGTGGAAAGGCCCATCTTCAGTCATCCTGTCCTCCAAG
AGAGGCTGCACGTCAAGGACAAAGTCACAGAGTCCATTGGAGATAAGCT
GAAGCAGGCATTCACGTGTACTCCTAAAAAAATAAGAAACATCATTTAC
ATGTTCCTGCCTATCACTAAGTGCTGCCAGCATATAAATTCAAGGAGTA
TGTGTTAGGTGACTTGGTCTCGGGCATAAGCACTGGGGTACTCCAGCTT
CCCCAAGGCTTAGCCTTCGCCATGCTGGCAGCCGTGCCTCCGGTGTTTG
GCCTGTACTCATCGTTTTACCCCGTTATCATGTACTGTTTCTTTGGAAC
CTCAAGACACATATCTATAGGTCCTTTTGCTGTTATTAGCTTGATGATT
GGAGGTGTGGCCGTCCGGTTAGTACCAGATGATATTGTCATCCCAGGAG
GAGTAAATGCAACCAACGGGACAGAAGCCAGAGATGCACTAAGAGTGAA
AGTCGCCATGTCTGTTACCTTACTTTCAGGAATCATTCAGTTTTGCCTA
GGTGTCTGTAGGTTTGGATTTGTGGCCATATACCTCACGGAGCCATGGT
GCGAGGCTTTACCACTGCGGCTGCTGTCCACGTGTTCACGTCCATGTTA
AAATACCTGTTTGGGGTCAAAACAAAGCGGTACAGTGGAATCTTTTCAG
TGGTGTATAGTACAGTTGCTGTGTTGCAGAATGTTAAAAACCTCAACGT
GTGTTCCCTAGGCGTCGGCCTGATGGTTTTGGTTTGCTGTTGGGTGGC
AAGGAATTTAATGAGAGATTTAAAGAGAAATTGCCAGCACCCATTCCTC
TAGAGTTCTTTGCTGTGGTGATGGGGACTGGCATTTCTGCAGGATTTAA
CCTACATGAGTCCTACAGTGTGGATGTCGTTGGAACACTTCCTCTGGGG
CTACTTCCTCCGGCCAACCCAGACACCAGCCTGTTCCACCTGGTGTATG
TGGACGCCATTGCCATCGCCATCGTTGGATTTTCAGTGACGATCTCCAT
GGCCAAAACCTTGGCAAATAAGCATGGCTACCAGGTTGATGGCAATCAG
GAGCTCATTGCCTTGGGGATATGCAACTCCATTGGATCTCTCTTCCAAA
CCTTCTCGATTTCCTGCTCCTTGTCTCGAAGCCTTGTTCAGGAAGGAAC
TGGAGGGAAAACACAGCTTGCAGGTTGTTTGGCCTCGTTGATGATTCTG
TTGGTCATATTAGCCACCGGATTCCTCTTTGAGTCGTTACCCCAGGCTG
TCCTTTCCGCCATTGTGATCGTCAACCTGAAAGGAATGTTCATGCAGTT
CTCAGACCTGCCTTTTTTTTGGAGAACCAGCAAAATAGAGCTGACCATC
TGGCTGACCACCTTTGTGTCCTCCCTGTTCCTCGGCTTGGACTACGGAC
TGATTACCGCCGTGATCATTGCTCTGCTCACAGTGATTTATAGAACACA
GAGTCCAAGCTACAAAGTCCTGGGGCAGCTCCCTGACACGGATGTGTAC
ATTGACATAGATGCATATGAGGAGGTGAAAGAATTCCTGGAATAAAAA
TATTCCAAATAAATGCCCCAATTTACTATGCAAATAGCGACTTGTATAG
CAGCGCTTTAAAAAGAAAGACTGGAGTAAACCCAGCACTCATTATGGGA
GCGAGAAGAAAGGCCATGAGGAAGTACGCCAAGGAAGTTGGAAATGCCA
ACGTGGCCAATGCTACTGTTGTCAAAGTGGATGCAGAAGTAGACGGAGA
AAATGCTACAAACCTGAAGAAGAGGATGATGAAGTCAAATTTCCCCCA
ATAGTCATCAAAACAACATTTCCTGAAGAGCTGCAGAGATTTTTGCCCC
AGGGGGAAAATGTCCACACTGTCATTCTAGACTTTACGCAGGTCAATTT
TGTGGATTCTGTTGGAGTGAAAACTCTGGCCGGGATTGTGAAAGAATAT
GGAGATGTTGGAATTTATGTATATTTAGCAGGATGCAGCCCACAAGTTG
TGAATGACCTCACCCGCAACAACTTTTTGAAAATCCTGCCTTGAAAGA
GCTTCTGTTCCACAGTATCCACGATGCAGTCCTGGGCAGCCAAGTTCGG
GAGGCAATGGCTGAACAAGAAGCCACAGCGTCACTTCCCCAGGAGGATA
TGGAGCCCAATGCCACACCCACCACCCCCGAGGCATAA
```

FIG 10A

```
MDHAEENEIP AETQRYYVER PIFSHPVLQE RLHVKDKVTE SIGDKLKQAF TCTPKKIRNI IYMFLPITKW

LPAYKFKEYV LGDLVSGIST GVLQLPQGLA FAMLAAVPPV FGLYSSFYPV IMYCFFGTSR HISIGPFAVI

SLMIGGVAVR LVPDDIVIPG GVNATNGTEA RDALRVKVAM SVTLLSGIIQ FCLGVCRFGF VAIYLTEPLV

RGFTTAAAVH VFTSMLKYLF GVKTKRYSGI FSVVYSTVAV LQNVKNLNVC SLGVGLMVFG LLLGGKEFNE

RFKEKLPAPI PLEFFAVVMG TGISAGFNLH ESYSVDVVGT LPLGLLPPAN PDTSLFHLVY VDAIAIAIVG

FSVTISMAKT LANKHGYQVD GNQELIALGI CNSIGSLFQT FSISCSLSRS LVQEGTGGKT QLAGCLASLM

ILLVILATGF LFESLPQAVL SAIVIVNLKG MFMQFSDLPF FWRTSKIELT IWLTTFVSSL FLGLDYGLIT

AVIIALLTVI YRTQSPSYKV LGQLPDTDVY IDIDAYEEVK EIPGIKIFQI NAPIYYANSD LYSSALKRKT

GVNPALIMGA RRKAMRKYAK EVGNANVANA TVVKVDAEVD GENATKPEEE DDEVKFPPIV IKTTFPEELQ

RFLPQGENVH TVILDFTQVN FVDSVGVKTL AGIVKEYGDV GIYVYLAGCS PQVVNDLTRN NFFENPALKE

LLFHSIHDAV LGSQVREAMA EQEATASLPQ EDMEPNATPT TPEA
```

FIG. 10B

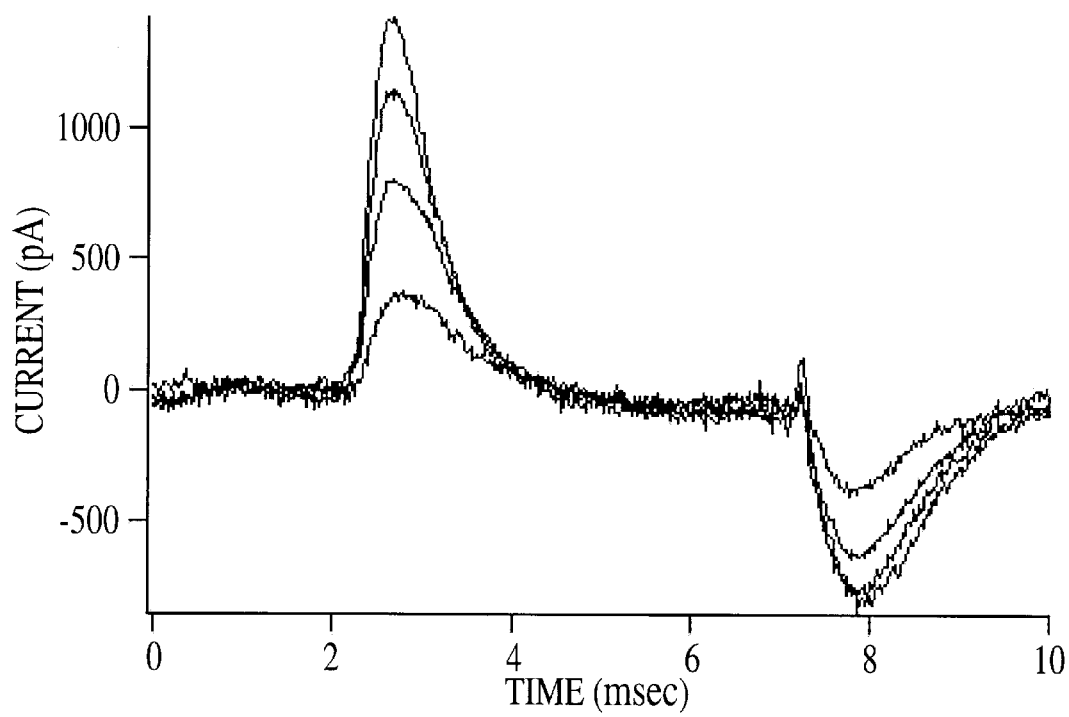
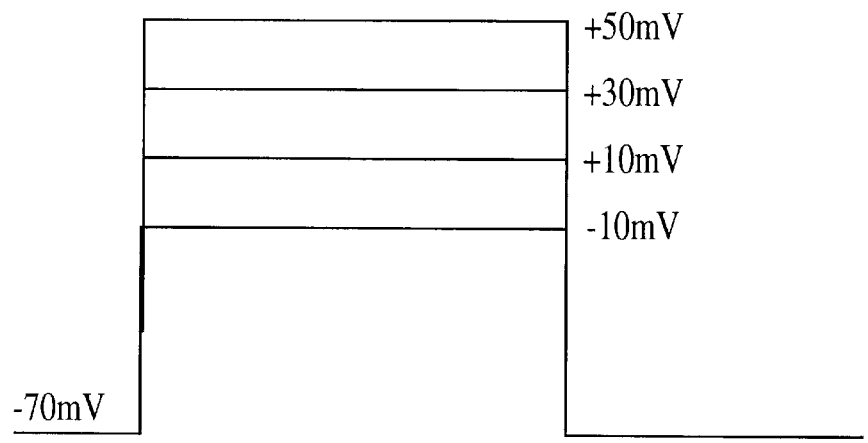
FIG. 20

MAMMALIAN PRESTIN POLYNUCLEOTIDES

CROSS REFERENCE TO RELATED APPLICATIONS

This application claims priority under 35 U.S.C. §119(e) to U.S. Provisional Application No. 60/183,461, filed on Feb. 19, 2000.

STATEMENT REGARDING FEDERALLY SPONSORED RESEARCH OR DEVELOPMENT

The invention was made in part using funds obtained from the U.S. Government (National Institutes of Health Grant No. DC00708) and the U.S. government may have certain rights in the invention.

BACKGROUND OF THE INVENTION

The mammalian cochlea has two types of hair cells. Cochlear hair cells are non-neuronal epithelial cells that transduce acoustic signals. Outer hair cells (OHCs) are responsible for the exquisite sensitivity and frequency-resolving capacity of the normal mammalian hearing organ, the ear; they provide local mechanical amplification (the "cochlear amplifier") in the form of feedback (1987, Ashmore, et al., J. Physiol. (London), 388:323–347). In contrast, inner hair cells (IHCs) convey auditory information to the brain (Dallos, P., Overview: Cochlear Neurobiology, pages 1–43, Springer, N.Y., 1996). OHCs have cylindrical somata of constant diameter and variable length. It is generally believed that the mammalian cochlea owes its remarkable sensitivity, frequency selectivity, and various complex nonlinear properties to a mechanical feedback action by OHCs.

In response to membrane potential change, the OHC rapidly alters its length and stiffness (1985, Brownell et al., Science, 227:194–196). These mechanical changes, driven by putative molecular motors, are assumed to produce amplification of vibrations in the cochlea that are transduced by IHCs. These somatic shape changes may be up to 5% of the cell length; The cell shortens when depolarized and lengthens when hyperpolarized. Length changes do not depend on either ATP or $Ca^{2+}$(1988, Holley et al., Proc. R. Soc. Lond. Ser. B. Biol. Sci., 232:413–429.) and they can be elicited with unchanging amplitude at microsecond rates up to high audio frequencies. Motile responses are accompanied by charge movement, reflected in nonlinear capacitance, akin to the translocation of gating charges of voltage-gated ion channels (1991, Santos-Sacchi et al., J. Neurosci., 11:3096–3110). This nonlinear capacitance is widely used as a "signature" of the electromotile process. Motility is also accompanied by axial stiffness change of the cell. By virtually any test, electromotility and electrically-induced stiffness changes can be correlated with each other and they are collectively described as voltage-dependent mechanical changes of the OHC, heretofore called electromechanics. These observations make it apparent that the fast mechanical changes in OHCs are powered by a novel molecular motor, fundamentally different from other biological force generators, such as the myosin, kinesin or dynein families. The OHC molecular motor performs direct, rapid, reversible electromechanical conversion.

Despite extensive studies of cellular and biophysical mechanisms of OHC function, very little is known about the genes and molecular events involved in OHC function. OHC electromotility is the likely result of the concerted action of a large number of independent molecular motors that are closely associated with the cell's basolateral membrane, possibly by the densely packed 10 nanometer particles seen therein.

There have been some suggestions as to the identity of these motor molecules. Based on similarities between the cortical structure of erythrocytes and OHCs, it has been proposed that the motor molecule is a modified anion exchanger. Because their shallow voltage dependence matches that of charge movement in OHCs, transporters have been favored, as opposed to modified voltage-dependent channels, as likely candidates. A recent suggestion is that the motor is related to a fructose transporter, GLUT5. Until the present invention, molecular identification of the motor protein has not been achieved.

SUMMARY OF THE INVENTION

The invention includes an isolated polynucleotide comprising a portion that anneals with high stringency with at least twenty consecutive nucleotide residues of a coding region of a mammalian pres gene.

In one aspect, the mammalian pres gene comprises a nucleotide sequence listed in SEQ ID NO:2 or SEQ ID NO:4.

In another aspect, the coding region is one other than a coding region corresponding to any of exons 1–6 of the human pres gene.

The invention also includes an isolated polynucleotide comprising the coding regions of a mammalian prestin gene, wherein the coding regions of the prestin gene are at least 75% homologous with the coding region of at least one of the gerbil and murine prestin gene.

In a preferred aspect, the isolated polynucleotide comprises a promoter/regulatory region operably linked with the coding regions.

An isolated mammalian prestin protein is also encompassed by the invention. In one aspect, the mammalian prestin protein is isolated from a gerbil, a mouse, or a human. In another aspect, the protein has an amino acid sequence listed in SEQ ID NO:1 or SEQ ID NO:3. Preferably, the protein is substantially purified.

Also contemplated by the invention is an isolated antibody which binds specifically with a mammalian prestin protein.

The invention includes a method of alleviating a hearing disorder in a mammal afflicted with the disorder comprising providing a mammalian prestin protein to cochlear outer hair cells of the mammal, thereby alleviating the disorder. In one aspect, the protein is provided to the outer hair cells by providing a nucleic acid vector comprising a polynucleotide encoding the protein to the outer hair cells.

A method of rendering the surface area of a lipid bilayer susceptible to modulation by membrane potential is also envisaged in the invention. The method comprises providing a mammalian prestin protein to the bilayer, whereby the bilayer is rendered susceptible to modulation by membrane potential. In an aspect of the invention, the lipid bilayer is the plasma membrane of a cell.

In another aspect, the protein is provided to the lipid bilayer by providing an expressible nucleic acid vector comprising a polynucleotide encoding the protein to the cell and then expressing the protein in the cell.

The invention also includes a method of modulating the surface area of a lipid bilayer. The method comprises providing a mammalian prestin protein to the bilayer and modulating the membrane potential, thus modulating the surface area of the bilayer.

A method for modulating stiffness of a lipid bilayer surrounding a relatively fixed volume is also within the scope of the invention. The method comprises providing a mammalian prestin protein to the bilayer, modulating the membrane potential, and thus, modulating bilayer stiffness.

The invention also encompasses a method of modulating the volume of a porous bilammelar lipid vesicle. The method comprises providing a mammalian prestin protein to the bilayer and modulating the membrane potential, thereby modulating the volume of the vesicle.

The invention further includes a method for generating a force between two surfaces. The method comprises interposing a structure having a lipid membrane comprising prestin and enclosing a relatively fixed volume of fluid between the surfaces, restraining the ability of the structure to expand in a direction at least partially parallel to at least one of the surfaces, and altering the membrane potential of the lipid membrane. The structure impacts upon the two surfaces and a force is generated between them.

The invention also describes a method for generating an electrical impulse by applying a mechanical force to the prestin protein. The method comprises applying a mechanical stress on the prestin protein, such that the protein creates an electrical impulse in response to the mechanical force.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. However, it should be understood that the invention is not limited to the precise arrangements and instrumentalities shown. In the drawings:

FIG. 1, comprising FIG. 1A represents forward-subtracted probe (OHC—IHC). FIG. 1B represents reverse-subtracted probe (IHC—OHC). FIG. 1C represents OHC probe, and FIG. 1D represents IHC probe. A signal comparison between OHC or OHC—IHC hybridization and IHC or IHC—OHC hybridization is indicated by the arrows.

FIG. 2 depicts the amino acid sequence of gerbil prestin (upper row), GenBank Accession Number AF230376 and SEQ ID NO:1, and rat pendrin (lower row), GenBank Accession Number AF167412 (SEQ ID NO:11). Bolded and underlined residues indicate the differences between the deduced human prestin sequence. Identical residues are indicated with an asterisk (*), while highly similar amino acids are indicated with a solid circle (●). The sulfate transport motif is boxed with a solid line. The positive charge cluster is outlined by a dotted line, and the negative charge cluster is boxed with a dashed line.

FIG. 3, comprising FIGS. 3A and 3B, lists the alignment of various sulfate transport motifs in selected proteins. FIG. 3A aligns prestin, pendrin, down-regulated in adenoma (DRA), and distrophic dysplasia (DTD) sequences from human and rodent species. Divergent residues in the prestin sequences are bolded. Amino acid residue numbers refer to gerbil prestin. FIG. 3B depicts sulfate transport motifs in a variety of putative transporters in lower organisms. Invariant residues are indicated with asterisks. The sulfate transport motif is defined by PROSITE PS01130.

FIG. 4, comprising FIG. 4A is a virtual Northern blot analysis of cDNA pools derived from mRNA of gerbil tissues hybridized with a [$^{32}$P]-labeled pres probe. FIG. 4B depicts PCR results where cDNA pools from different tissues were amplified with pres-specific and cyclophilin-specific primers. In FIGS. 4A and 4B, cochlea was derived from the organ of Corti. FIG. 4C is also a virtual Northern blot analysis. cDNA pools derived from the organ of Corti mRNA at 0, 6, 12, 16, and 20 days after birth (DAB) were hybridized with a [$^{32}$P]-labeled pres-specific probe, followed by stripping and rehybridization with a [$^{32}$P]-labeled cyclophilin probe. FIG. 4D indicates PCR results from the cDNA in FIG. 4C, amplified with pres and cyclophilin-specific primers.

FIG. 5, comprising FIG. 5A illustrates the charge movement measured as transient capacitive currents using a standar subraction technique (P/4). The cell is held at −70 millivolts and voltage steps are 20 millivolts to +50 millivolts. FIG. 5B is a stair-step protocol quantifying voltage dependence of nonlinear capacitance of 20 presentations which were averaged. Voltage was increased from −130 millivolts to +40 millivolts in 10 millivolt increments. FIG. 5C illustrates the membrane capacitance-voltage curve obtained from the stair-step current trace in FIG. 5B. The trace fits data points with a derivative of a Boltzmann function. FIG. 5D demonstrates that localized application of 10 millimolar sodium salicylate reversibly blocks charge movement.

FIG. 6, comprising FIG. 6A is an image of a TSA201 cell being partially drawn in to a microchamber. FIG. 6B is a trace representing motile responses from control and transfected cells. The top two traces depict motile responses for the transfected cells, while the bottom trace depicts lack of motile response for the control cell. FIG. 6C demonstrates the effect of 10 millimolar sodium salicylate in the external bathing solution on the motile response. FIG. 6D depicts response (top) and stimulus (bottom) waveforms with two different command frequencies. FIG. 6E illustrates Fourier transforms of the response segments in FIG. 6D (top). A 1.2 decibel correction for frequency response was incorporated into the resultant Fourier transforms in FIG. 6E. Response waveforms are the average of 200 presentations.

FIG. 7, comprising FIGS. 7A and 7B, lists the gerbil cDNA sequence encoding prestin (SEQ ID NO:2).

FIG. 8, comprising FIGS. 8A, 8B, and 8C lists a portion of the nucleotide sequence (SEQ ID NO:2) and the amino acid sequence of gerbil prestin (SEQ ID NO:1) with the corresponding human amino acid sequence beneath it (SEQ ID NO:5).

FIG. 9, comprising FIGS. 9A–9M, lists a portion of the nucleic acid sequence of BAC clone RG107G13 (GenBank Accession Number RG107G13; SEQ ID NO:6) from nucleotide residue number 90,000 to nucleotide residue number 119, 484.

FIG. 10, comprising FIGS. 10A and 10B, lists the murine cDNA sequence of prestin (FIG. 10A, SEQ ID NO:4) and the murine amino acid sequence of prestin (FIG. 10B, SEQ ID NO:3).

FIG. 12, comprising

FIG. 13, comprising FIG. 13C depicts the same responses in graph form.

FIG. 16, comprising FIG. 16A represents a hybridization blot hybridized with radioactive forward subtracted (OHC—IHC) probe. FIG. 16B represents hybridization with radioactive reverse subtracted (IHC—OHC) probe. FIGS. 16C and 16D represent hybridization with radioactive tester (OHC) and driver (IHC) probes, respsectively.

FIG. 19, comprising FIG. 19A illustrates cells transfected with control vector and FIG. 19B demonstrates cells transfected with C-terminal tagged prestin.

FIG. 20 depicts the nonlinear capacitance of TSA201 cells transiently transfected with N-tagged prestin construct.

FIG. 21, comprising FIGS. 21A and 21C) and N-tagged prestin (Xpress epitope; FIGS. 21B and 21D). FIGS. 21A and 21B depict permeabilized cells and FIGS. 21C and 21D depict nonpermeabilized cells. C-tagged prestin magnification is 100×. N-tagged prestin magnification is 40×.

FIG. 22, comprising FIGS. 22A and 22B represent the identical cells transfected with C-tagged prestin, with different filters. Magnification at 40×. FIG. 22C and 22D represent identical cells viewed with different filters. Magnification at 20×. FIGS. 22A and 22C depict cells binding with FITC-labeled anti-rabbit IgG, indicating cells expressing native prestin FIGS. 22B and 22D depict cells binding with Cy3-conjugated mouse IgG, indicating cells expressing the V5 tag epitope.

FIG. 23, comprising FIGS. 23A and 23B depict images of the same cells, viewed through different filters at 20× magnification. FIGS. 23C and 23D depict images of the same cells viewed through different filters at 40× magnification. FIGS. 23A and 23C depict cells binding with FITC-labeled rabbit IgG, indicating cells expressing prestin. FIGS. 23B and 23D depict cells stained with propidium iodide, indicating location of the cell nuclei.

FIG. 24, comprising FIGS. 24A and 24C are magnified 20× and FIGS. 24B and 24D are magnified 40×.

DETAILED DESCRIPTION OF THE INVENTION

The invention relates to discovery of an integral membrane protein which modulates the shape of mammalian cochlear outer hair cells in response to the membrane potential of the plasma membrane of the cells. Inasmuch as the most distinguishing feature of this novel molecular motor of the invention is its speed, it has been designated as "prestin", from the musical notation presto. The gene (Prestin) coding for this protein is abbreviated "Pres", herein.

Figure 8A:
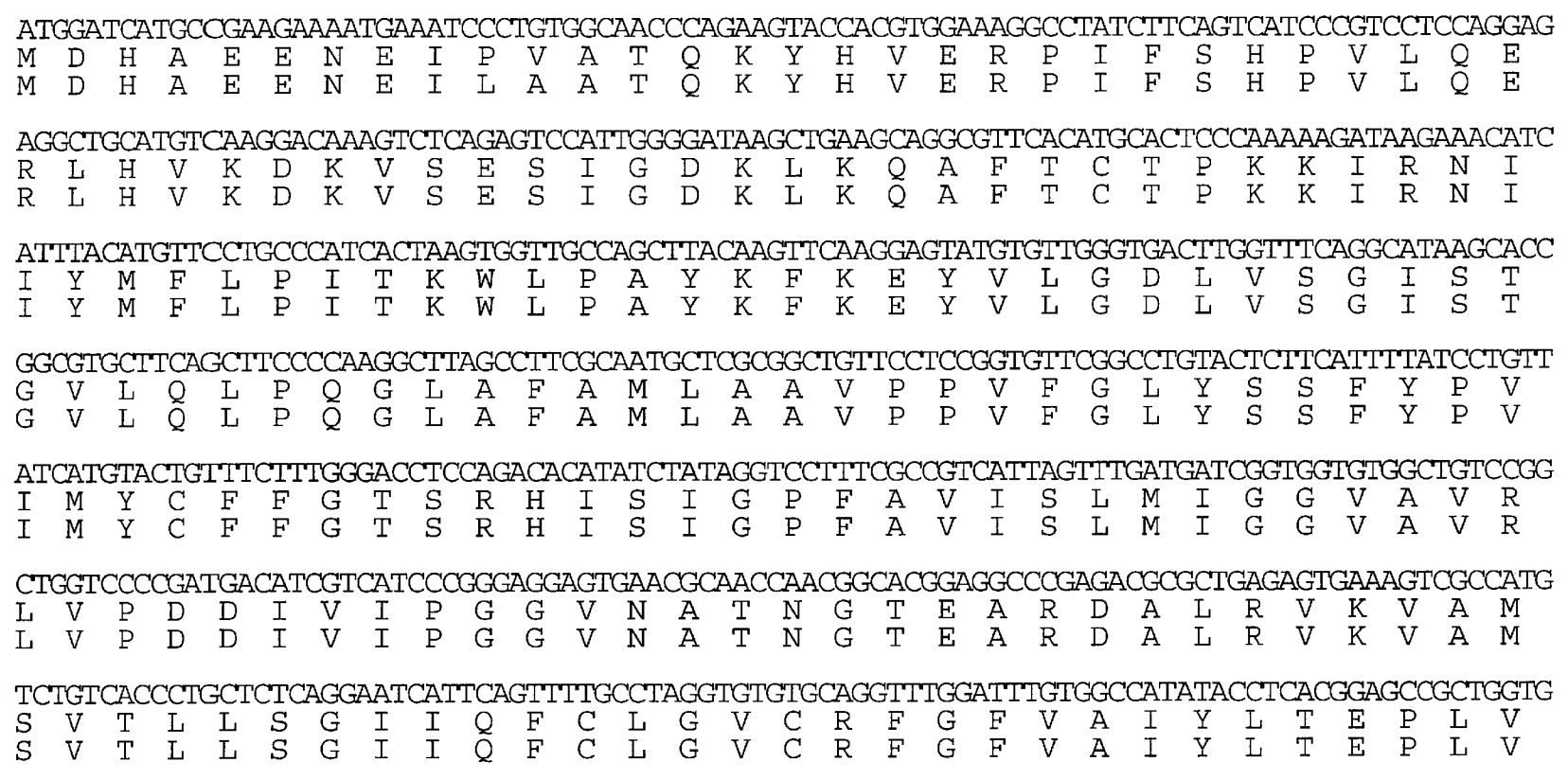
Figure 8B:
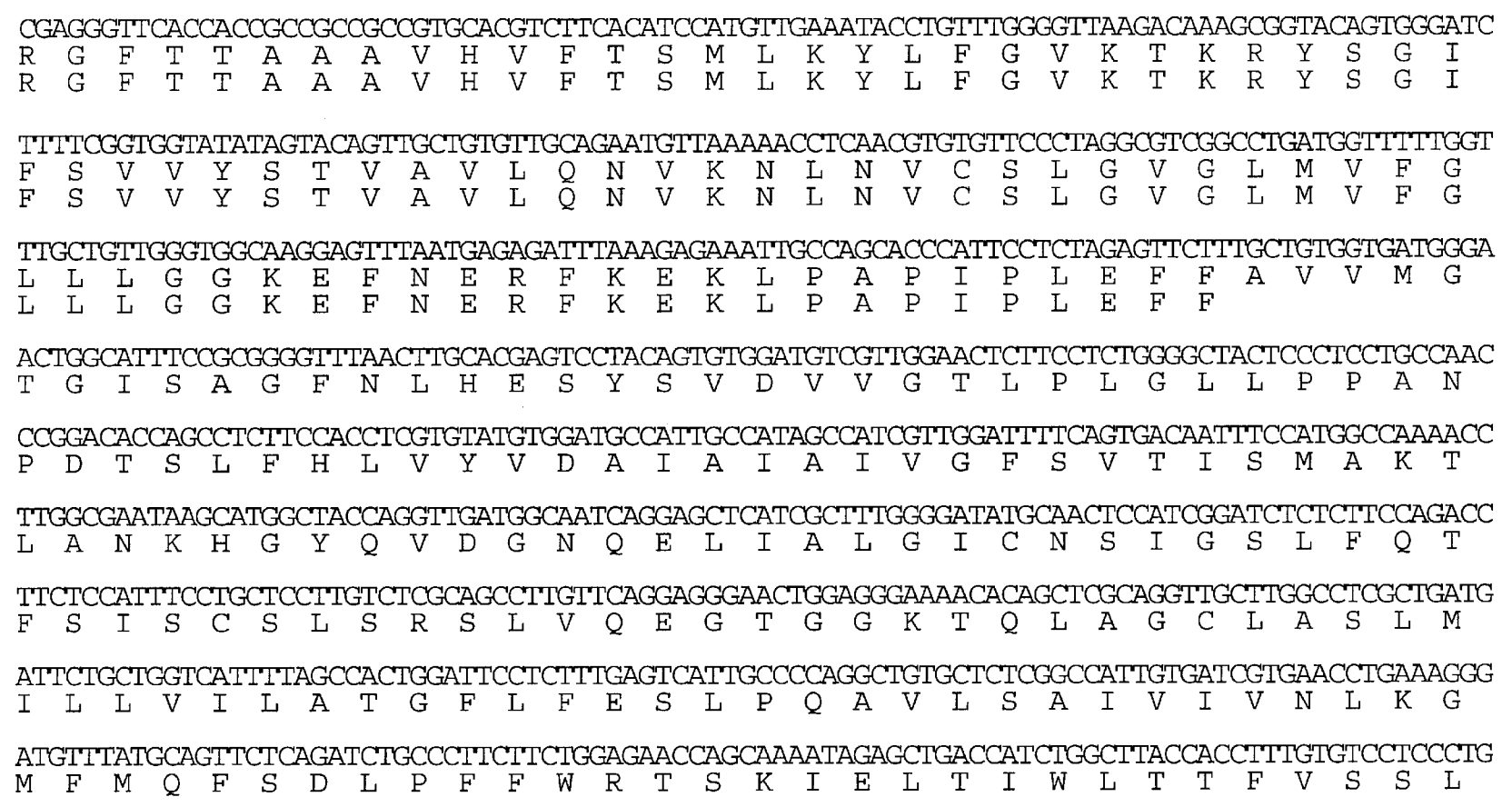
Figure 9A:
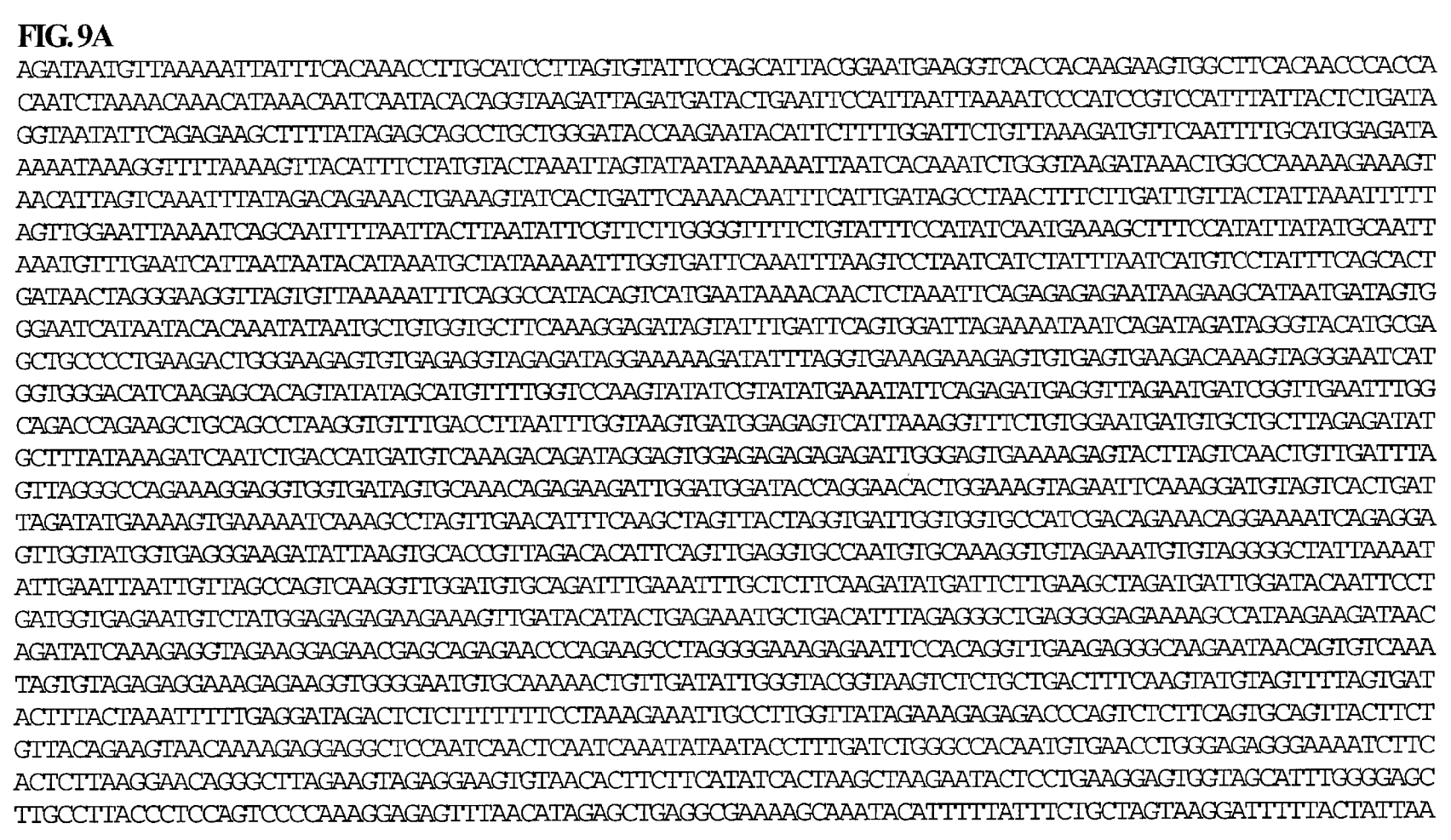
Figure 9D:
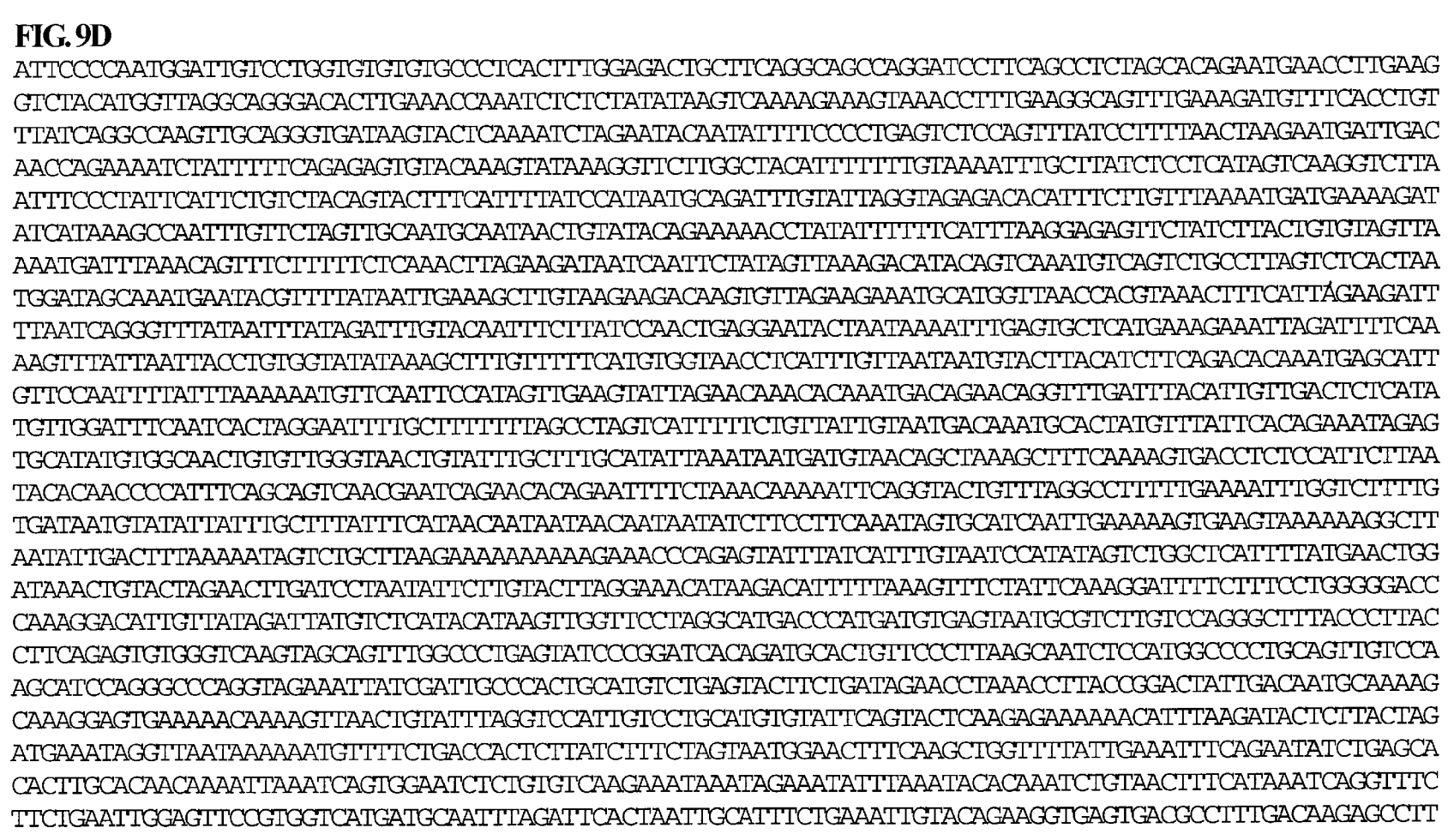
Figure 9J:
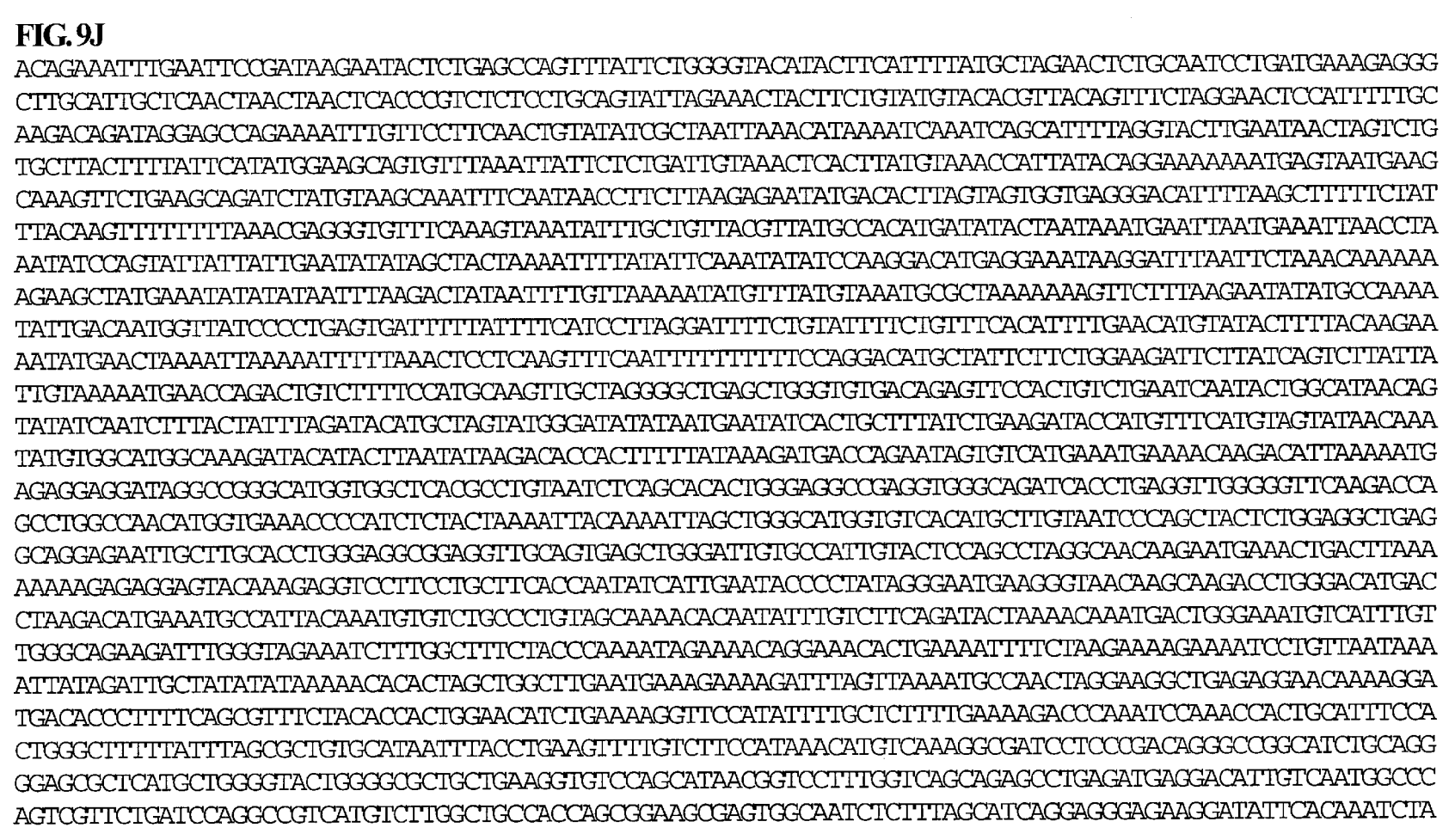
Figure 19A:
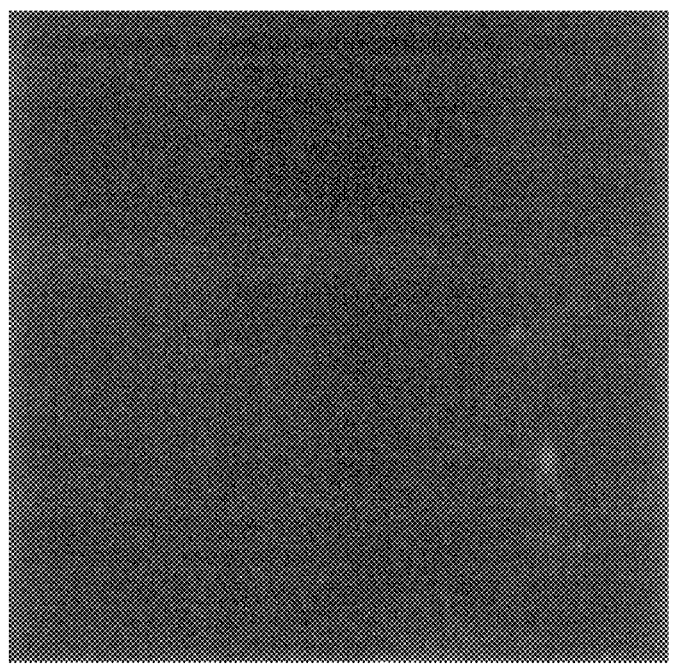
FIGS. 19A and 19B, is a pair of images depicting immunofluorescent expression of C-terminal tagged pres in transfected TSA201 cells.
Figure 19B:
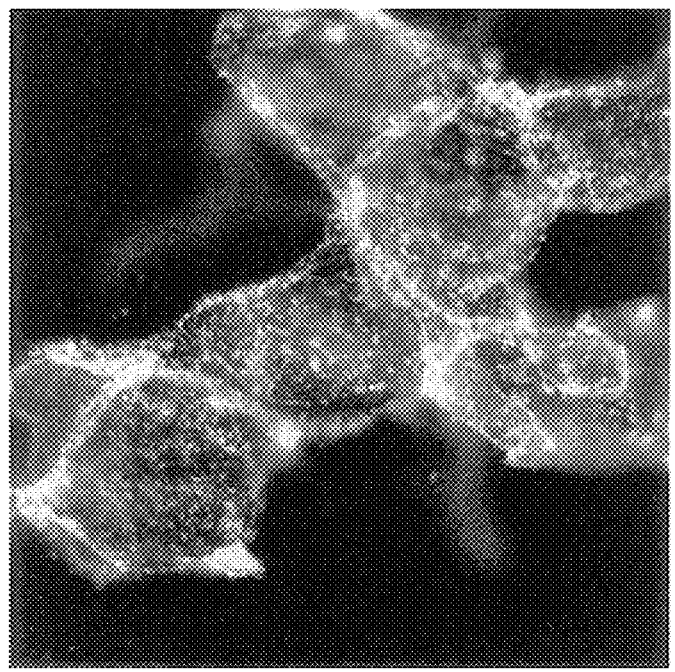

The amino acid sequence (SEQ ID NO:1) of gerbil prestin is listed in FIG. 2, and the nucleotide sequence (SEQ ID NO:2) of a gerbil cDNA which encodes prestin is listed in FIG. 7. A portion of the human gene (herein designated the pres gene) encoding prestin has been sequenced as a part of the human chromosome 7 sequencing effort. This portion corresponds to at least nucleotide residues 99,895–113,558 of BAC clone RG107G13 (GenBank Accession number RG107G13). The nucleotide sequence of residue numbers 90,000 to 119,484 of this clone (SEQ ID NO:6) is reproduced in FIG. 9. The portion of the amino acid sequence of human prestin (SEQ ID NO:5) corresponding to the sequenced region is referred to in FIG. 2 and is listed below the corresponding gerbil prestin amino acid sequence (SEQ ID NO:1) in FIG. 8. FIG. 19 depicts surface expression of C-tagged prestin in TSA201 cells which were transfected as described in that example. The amino acid sequence (SEQ ID NO:3) of murine prestin and the nucleotide sequence (SEQ ID NO:4) of a cDNA encoding it have been determined, and are listed in FIG. 10B and 10A, respectively. Portions of the murinepres gene were reported by others in a BAC clone derived from murine chromosome 5. The nucleotide sequence of this BAC clone is listed in GenBank accession number AC023284.

The invention includes an isolated polynucleotide which anneals with high stringency with at least twenty consecutive nucleotide residues of at least one strand of a mammalian pres gene, (e.g. the human, murine, or gerbil pres gene), or with one strand having a nucleotide sequence comprising SEQ ID NO:2 having naturally-occurring introns interposed therewithin, or a coding region thereof. Preferably, the isolated polynucleotide of the invention anneals with high stringency with at least 25, more preferably with at least 30, and even more preferably with at least 40, at least 50, or at least 100 consecutive nucleotide residues. In certain embodiments, the isolated polynucleotide of the invention has a length not greater than about 200 nucleotide residues, more preferably not greater than about 100 nucleotide residues, and even more preferably not greater than about 50, 40, or even 35 nucleotide residues.

The isolated polynucleotide of the invention preferably has a sequence that is substantially homologous with at least 20, 25, or 35 consecutive nucleotide residues of at least one strand of the mammalian pres gene. More preferably, the isolated polynucleotide of has a sequence completely homologous with at least 20, 25, or 35 consecutive nucleotide residues of at least one strand of the mammalian pres gene, and even more preferably with at least 20, 25, or 35 consecutive nucleotide residues of at least one strand of a DNA having the nucleotide sequence SEQ ID NO:2 or SEQ ID NO:4.

The isolated polynucleotide can be inserted into a gene vector in order to facilitate cloning, fusion protein production, or delivery of the polynucleotide to a cell (i.e. in vitro or in vivo) for the purpose of inducing or enhancing expression of pres in the cell or for the purpose of inhibiting or preventing expression of pres in the cell (e.g. using an antisense oligonucleotide which binds specifically with at least one strand of a portion of the pres gene). When the vector is intended for use to induce or enhance expression of pres in a cell, the vector includes one or more promoter/regulatory sequences which cause the gene to be expressed in the presence of the normal transcription and/or translation mechanism of the cell.

When the isolated polynucleotide of the invention is to be hybridized or annealed with a nucleic acid having a sequence wherein at least a portion is complementary to the isolated polynucleotide, the necessary degree of homology between the isolated polynucleotide and the at least one strand of pres is dependent on the length of the polynucleotide. It is well known in the art that, as the length of a polynucleotide increases, the degree of complementarity necessary to anneal the polynucleotide with another polynucleotide with high stringency decreases. Numerous methods, algorithms, computer programs, and the like are known whereby the skilled artisan may predict the stringency of binding between two polynucleotides (e.g. Suhai, Ed., 1992, *Computational Methods in Genome Research*, Plenum Press, New York; Swindell, Ed., 1997, *Sequence Data Analysis Guidebook*, Humana Press, New Jersey; Bishop, Ed., 1998, *Guide to Human Genome Computing*, Academic Press, New York). Any of these methods, etc., may be used by the skilled artisan, in light of the present disclosure, to design or select isolated polynucleotides of various lengths which will anneal with at least one strand of a human pres gene with high stringency. All such isolated polynucleotides are included within the invention.

When the isolated polynucleotide of the invention is to be used to express all or a portion of a mammalian (e.g. human, murine, or gerbil) prestin protein, either in vitro or in vivo, it is important that (i) the homology of the isolated polynucleotide of the pres gene (e.g. SEQ ID NO:2) is such that the amino acid sequence encoded by the isolated polynucleotide is identical to the corresponding region of pres, (ii) the differences between the sequence of the isolated polynucleotide and the corresponding region of pres does not result in differences in the encoded amino acid sequence (i.e. any sequence difference in a coding region merely substitutes a codon encoding an amino acid in place of another codon encoding the same amino acid), or (iii) any differences in the encoded amino acid sequence between the isolated polynucleotide and the corresponding region of pres results only in one or more conservative amino acid substitutions, as described in greater detail elsewhere herein. The following Human Codon Table may be used to select or identify alternate codons which encode the same amino acid.

Human Codon Table

| Amino Acid | Codons Encoding the Amino Acid |
|---|---|
| Alanine | GCA GCC GCG GCU |
| Cysteine | UGC UGU |
| Aspartic acid | GAC GAU |
| Glutamic acid | GAA GAG |
| Phenylalanine | UUC UUU |
| Glycine | GGA GGC GGG GGU |
| Histidine | CAC CAU |
| Isoleucine | AUA AUC AUU |
| Lysine | AAA AAG |
| Leucine | UUA UUG CUA CUC CUG CUU |
| Methionine | AUG |
| Asparagine | AAC AAU |
| Proline | CCA CCC CCG CCU |
| Glutamine | CAA CAG |
| Arginine | AGA AGG CGA CGC CGG CGU |
| Serine | AGC AGU UCA UCC UCG UCU |
| Threonine | ACA ACC ACG ACU |
| Valine | GUA GUC GUG GUU |
| Tryptophan | UGG |
| Tyrosine | UAC UAU |

In situations in which it is necessary or desirable to introduce nucleotide residue changes into a polynucleotide, or into a prestin protein or a portion thereof, a variety of well-known techniques may be used, such as site-specific mutagenesis. Site-specific mutagenesis, for example, allows production of mutants through the use of specific oligonucleotides which encode the sequence of the desired mutation, as well as a sufficient number of adjacent nucleotides, to provide a primer sequence of sufficient size and sequence complementarity to form a stable duplex on both sides of the nucleotide sequence to be altered (e.g. a codon). Typically, a primer of about 17 to 25 nucleotides in length is preferred, with about 5 to 10 residues on both sides of the junction of the sequence being altered. This technique typically employs a phage vector which exists in both a single stranded and double stranded form. Typical vectors useful in site-directed mutagenesis include vectors such as M13 phage. Such vectors are commercially available, and their use is well known in the art. Double stranded plasmids are also routinely employed in site-directed mutagenesis protocols, to eliminate the need to transfer the gene of interest from a plasmid to a phage vector. Site-directed mutagenesis is performed by first obtaining a single-stranded vector or dissociating the two strands of a double stranded vector which includes within its sequence a DNA sequence which comprises the desired site of mutagenesis. The oligonucleotide primer described above is annealed with the single-stranded vector, and subjected to DNA polymerization, in order to generate a mutation-bearing strand. A heteroduplex is formed between the mutation-bearing strand and either the original non-mutated strand of the double-stranded vector or an added or synthesized strand which is substantially complementary to the mutation-bearing strand. This heteroduplex is then used to transform appropriate cells, such as *E. coli* or cultured human cells, and clones are selected which comprise recombinant vectors bearing the mutated sequence arrangement. Preparation of sequence variants of the isolated polynucleotide of the invention using site-directed mutagenesis is provided merely as an example of a method of producing potentially such variants, and is not intended to be limiting, as there are other well-known methods for producing such variants. By way of example, recombinant vectors comprising or encoding the desired isolated polynucleotide may be treated with mutagenic agents, such as hydroxylamine, to obtain sequence variants.

The isolated polynucleotide of the invention may be single stranded or double-stranded, it being understood that a single-stranded form is the form referred to herein when annealing of the isolated polynucleotide of the invention with another nucleic acid is described.

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264–2268), modified as in Karlin and Altschul (1993, Proc. Natl. Acad. Sci. USA 90:5873–5877). This algorithm is incorporated into the NBLAST and XBLAST programs of Altschul, et al. (1990, J. Mol. Biol. 215:403–410), and can be accessed, for example at the National Center for Biotechnology Information (NCBI) world wide web site having the universal resource locator "http://www.ncbi.nlm.nih.gov/BLAST/". BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389–3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used. See http://www.ncbi.nlm.nih.gov.

The percent identity between two sequences can be determined using techniques similar to those described above, with or without allowing gaps. In calculating percent identity, typically exact matches are counted.

The invention also relates to an isolated prestin protein which has a sequence which is identical or highly homologous (e.g. 70%, 80%, 85%, 90%, 95%, 98%, or 99% or more homologous) with the amino acid sequence of gerbil prestin (SEQ ID NO:1) or murine prestin (SEQ ID NO:3). Preferably, the isolated prestin protein is substantially purified. The isolated prestin protein may be in the form of a suspension of the native or denatured protein in a liquid such as water, a buffer, or the like, a lyophilized powder, an immunogenic composition comprising the protein and one or more adjuvants or immunogenicity enhancers such as are known in the art, or a pharmaceutical composition.

The isolated prestin protein of the invention may be made by a variety of techniques. For example, the protein may be expressed in an in vitro expression mixture using an isolated polynucleotide of the invention. The isolated polynucleotide of the invention may also be operably linked with a constitutive or other promoter, and the prestin protein is then over-expressed in a human or non-human cell, and subsequently purified therefrom. Alternately, the prestin protein may be purified using, for example, standard chromatographic techniques from a naturally occurring source of prestin protein (e.g. mammalian cochlear outer hair cells).

The isolated prestin protein can have an amino acid sequence completely homologous with SEQ ID NO:1 or SEQ ID NO:2, or it can comprise one or more conservative amino acid substitutions relative to either of these two sequences). For example, the protein can have an amino acid sequence which incorporates the differences between any two of the gerbil, murine, and human prestin amino acid sequences described herein. Furthermore, it is within the level of skill of the ordinary worker to determine the remainder of the sequence of the human pres gene (e.g. by constructing an oligonucleotide primer that is complementary to the end of BAC clone RG107G13 corresponding to pres, isolating a genomic fragment that hybridizes with the primer, and determining the sequence of the genomic fragment beyond that provided in BAC clone RG107G13). Thus, the present invention includes isolated human prestin as well.

Certain amino acids of prestin may be substituted for other amino acids without appreciably affecting the biological activity of the protein. Preferably, the amino acid sequence of the isolated prestin protein is substantially homologous with SEQ ID NO:1 or the sequence of human prestin. The hydropathic index of naturally occurring prestin amino acid residues may be compared with those of potential substitute amino acid residues. The significance of amino acid hydropathic index similarity between naturally occurring and potential substitute amino acid residues, as it relates to retention of biologic function of a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each naturally occurring amino acid residue has been assigned a hydropathic index on the basis of their hydrophobicity and charge characteristics, as described (Kyte et al., 1982, J. Mol. Biol. 157:105). These hydropathic index values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (+1.3); proline (−1.6); histidine (−3.2); glutamate (−3.5);glutamine (−3.5); aspartate (−3.5); asparagine (−3.5); lysine (−3.9); and arginine (−4.5). Amino acid residues may be substituted in place of other amino acid residues which having a similar hydropathic index without significantly affecting biological activity of the protein. Preferably, the substitute amino acid residue has a hydropathic index which differs from the hydropathic index of the naturally occurring amino acid residue by less than 2.0, preferably by less than 1.0, and more preferably by less than 0.5. For example, if the hydropathic index of a naturally occurring amino acid residue is 1.8, then a substitute amino acid residue should have a hydropathic index in the range from 3.8 to −0.2, preferably in the range from 2.8 to 0.8, and more preferably in the range from 2.3 to 1.3.

An alternate method may be used to predict amino acid residues which may be substituted in place of naturally occurring prestin amino acid residues in regions of prestin which are predicted to interact with other molecules, such as regions predicted to interact with the plasma membrane of cells. This method has been described in the art (Hoop et al., 1981, Proc. Natl. Acad. Sci. USA 78:3824), and involves assigning the following hydrophilicity values to amino acid residues: arginine (+3.0); lysine (+3.0); aspartate (+3.0); glutamate (+3.0); serine (+0.3); asparagine (+0.2); glutamine (+0.2); glycine (0); proline (0.0); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Amino acid residues may be substituted in place of other amino acid residues having a similar hydrophilicity value without significantly affecting biological activity of the protein. Preferably, the substitute amino acid residue has a hydrophilicity value which differs from the hydrophilicity value of the naturally occurring amino acid residue by less than 2.0, preferably by less than 1.0, and more preferably by less than 0.5. For example, if the hydrophilicity value of a naturally occurring amino acid residue is 1.8, then a substitute amino acid residue should have a hydrophilicity value in the range from 3.8 to −0.2, preferably in the range from 2.8 to 0.8, and more preferably in the range from 2.3 to 1.3.

As outlined above, amino acid substitutions may be based on the relative similarity of the amino acid side-chain substituents, for example, their hydrophobicity, hydrophilicity, charge, size, and the like. For example, conservative amino acid substitutions may include substitutions within the following groups:

glycine, alanine;

valine, isoleucine, leucine;

aspartic acid, glutamic acid;

asparagine, glutamine;

serine, threonine;

lysine, arginine;

phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Isolated prestin protein, or a fragment thereof, may be used to generate polyclonal or monoclonal antibodies using known methods. As is well known, administration of prestin protein to an animal can induce a soluble immune response against the protein or fragment in the animal. Preferably, the protein or fragment is mixed with an adjuvant or other immune system enhancer. Such adjuvants include, but are not limited to, mineral gels such as aluminum hydroxide, surface active substances such as lysolecithin, pluronic polyols, and polyanions, other peptides, and oil emulsions. Antibodies which bind specifically with the prestin protein or fragment may be identified and isolated using well known methods (see, e.g. Harlow et al., 1988, *Antibodies: A Laboratory Manual*, Cold Spring Harbor, N.Y.). Likewise, immortal hybridomas may be generated using known methods to provide a supply of such antibodies.

The amino acid and nucleotide sequences of prestin and pres, respectively, which are provided herein can be used to diagnose a disorder associated with aberrant expression of pres. Aberrant expression of pres includes, for example, expression of prestin protein having an amino acid sequence that differs from the normal (i.e. wild type) sequence of prestin, over- or under-expression of pres relative to normal expression levels, expression of pres in tissues in which it is not normally expressed, and non-expression of pres in tissues in which it normally is expressed. By way of examples, disorders which are associated with aberrant expression of pres include various forms of deafness, other hearing impairment, and other hearing disorders, including disorders linked with the autosomal recessive locus designated DFN B14, such as a congenital, sensorineural, autosomal recessive form of non-syndromic deafness associated with this locus.

The amino acid and nucleotide sequences of prestin and pres, respectively, which are provided herein can also be used to treat a disorder associated with aberrant expression of pres. For example, wild type prestin protein or wild type pres can be provided to a cell which expresses less than a normal amount of the wild type protein (e.g. one which expresses a non-functional form of prestin or one which expresses no prestin). Alternatively, an antisense oligonucleotide which binds specifically with at least one strand of pres can be provided to a cell which expresses more than a normal or desirable amount of wild type or altered prestin protein, in order to inhibit or prevent such expression.

The ability of prestin to alter the surface area of a lipid bilayer, as described herein, can be used to affect the properties of either a naturally occurring lipid bilayer or a synthetic lipid bilayer. By way of example, providing prestin (i.e. in the form of the protein or in the form of a gene vector which will express the protein) to a cell renders the surface area of the plasma membrane of the cell susceptible to modulation by prestin. In the presence of an increased membrane potential (i.e. a membrane potential having a more negative value), a lipid bilayer comprising prestin is expanded relative to the surface area of the bilayer in the presence of a lower (i.e. less negative; more positive) membrane potential. If the lipid bilayer encloses a fixed volume (or a volume which cannot change as quickly as the surface area changes), then the tension within the bilayer is altered as the membrane potential changes. Thus, in the presence of a low membrane potential, the surface area of a lipid bilayer comprising prestin tends to decrease, so the surface tension of the bilayer increases if the bilayer surrounds a fixed volume, yielding a stiffer structure. Upon increasing membrane potential, the surface area of the bilayer increases, so the surface tension of a bilayer surrounding a fixed volume decreases yielding a more pliant structure.

The ability of prestin to modulate the surface area of a lipid bilayer can be used to modulate the volume of structure which is enclosed by a lipid bilayer if fluid can pass across the bilayer upon expansion or contraction of the bilayer mediated by prestin. Thus, for example, the volume (i.e. and diameter) of a 'leaky' (i.e. porous) bilammelar lipid membrane vesicle which comprises prestin can be modulated by changing the potential across the membrane. Similarly, the stiffness or shape of a structure which comprises a lipid bilayer surrounding a fluid can be modulated if the bilayer comprises prestin and if the rate at which the volume of the structure can change is less than the rate at which prestin can change the surface area of the bilayer (i.e. taking into account the geometric relationship between volume and surface area). Thus, a structure which comprises a lipid membrane comprising prestin enclosing a fixed (or relatively fixed) volume of fluid can be used as a force generator by interposing the structure between two surfaces upon which force can be exerted, restraining the ability of the structure to expand in a direction at least partially parallel to (i.e. absolutely parallel to or oblique with respect to) at least one surface, and modulating the membrane potential of the lipid membrane. Upon increasing the membrane potential (i.e., the electrical aspect), the structure expands in a direction normal to at least one surface, and outward force (relative to the structure) is exerted upon the surfaces, thereby urging the surfaces apart (i.e., the mechanical aspect). Upon decreasing the membrane potential, the structure contracts in a direction normal to at least one surface, and inward force (relative to the structure) is exerted upon the surfaces, thereby urging the surfaces together. Because structures comprising a lipid bilayer can be made on a microscopic (or even sub-microscopic) scale, these force generators can be exceedingly small, and are suitable for incorporation into very small (e.g. microscopic or nanometer-scale) apparatus.

It is also contemplated by the invention that by applying a mechanical force to prestin, an electrical impulse is created in response to the mechanical force. While the electrical impulse generated may be small, this aspect of the invention has use in electrical circuitry, and more specifically, in nanocircuitry. Thus, for example, prestin has the ability to modulate the electrical characteristics associated with the functions of the cochlea and, more generally, electrical functions associated with hearing.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is anti-parallel to the first region if the residue is thymine or uracil. Similarly, it is known that a cytosine residue of a first nucleic acid strand is capable of base pairing with a residue of a second nucleic acid strand which is anti-parallel to the first strand if the residue is guanine. A first region of a nucleic acid is complementary to a second region of the same or a different nucleic acid if, when the two regions are arranged in an anti-parallel fashion, at least one nucleotide residue of the first region is capable of base pairing with a residue of the second region. Preferably, the first region comprises a first portion and the second region comprises a second portion, whereby, when the first and second portions are arranged in an anti-parallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

An "isolated" polynucleotide or protein refers to a molecule which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to molecules which have been substantially purified from other components which naturally accompany the nucleic acid, e.g., RNA or DNA or proteins, which naturally accompany it in the cell.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked with the coding region of a gene is able to promote transcription of the coding region.

A first oligonucleotide anneals with a second oligonucleotide "with high stringency" if the two oligonucleotides anneal under high stringency hybridization conditions.

By "high stringency hybridization conditions" is meant those hybridizing conditions that (1) employ low ionic strength and high temperature for washing, for example, but not limited to 0.015 molar NaCl, 1.5 millimolar sodium citrate, and 0.1% (w/v) sodium dodecyl sulfate (SDS) at 50° C.; (2) employ during hybridization a denaturing agent such as formamide, for example, but not limited to 50% (v/v) formamide, 0.1% (w/v) bovine serum albumin, 0.1% (w/v) Ficoll, 0.1% (w/v) polyvinylpyrrolidone, and 50 millimolar sodium phosphate buffer at pH 6.5 with 750 millimolar NaCl, 75 millimolar sodium citrate at 42° C.; or (3) employ 50% (v/v) formamide, 5×SSC (0.75 molar NaCl, 75 millimolar sodium pyrophosphate, 5×Denhardt's solution, sonicated salmon sperm DNA (50 micrograms per milliliter), 0.1% (w/v) SDS, and 10% (w/v) dextran sulfate at 42° C., with washes at 42° C. in 0.2×SSC and 0.1% (w/v) SDS. Under stringent hybridization conditions, only highly complementary nucleic acids hybridize. Preferably, such conditions prevent hybridization of nucleic acids having 1 or 2 mismatches out of 20 contiguous nucleotides.

The term "substantially pure" describes a compound, e.g., a protein, polynucleotide, or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state.

By the term "specifically binds," as used herein, is meant a protein (e.g., an antibody) which recognizes and binds a prestin protein but does not substantially recognize or bind other molecules in a sample.

By the term "lipid bilayer", as used herein, is meant a membrane formed by phospholipids in a bimolecular layer. This term should be construed to include naturally-occurring, as well as artificially prepared membranes.

The term "modulation" describes regulation of some quantity or measure of a product or process. For example, a protein is said to be modulated when expression is either increased or decreased.

The invention is now described with reference to the following Examples. These Examples are provided for the purpose of illustration only and the invention is not limited to these Examples, but rather encompasses all variations which are evident as a result of the teaching provided herein.

EXAMPLES

Example 1: Prestin is the Motor Protein of Cochlear Outer Hair Cells Tissue Preparation and Pres cDNA Isolation by Subtractive PCR Hybridization Outer hair cells and inner hair cells are distinct sensory receptor cells in the mammalian organ of Corti. They both have hair bundles at the cell apex, though their bundle lengths, numbers and configuration are quite different. They both are rich in mitochondria in order to maintain their active physiologic function. It is likely that a vast array of housekeeping genes as well as genes that code for metabolism, the transducer apparatus and a variety of common ion channels are duplicated in IHC and OHC. These and other similarities between OHC and IHC make IHC an ideal "driver" in order to "subtract-away" common hair cell genes, allowing isolation of OHC specific genes. The use of inner and outer hair cells as sources of cell-type specific mRNA should reduce the number of candidate genes obtained after the subtraction-hybridization process and thus enhance the likelihood of successful isolation of OHC specific genes.

A unique and abundant OHC-specific cDNA from a gene, designated Prestin (Pres), has been identified herein via OHC minus IHC subtractive PCR hybridization and differential screening. The protein prestin is novel, but some of its regions exhibit moderate homology to pendrin and sulfate/anion transport proteins. Voltage-induced shape change can be elicited in human kidney (TSA201) cells that express prestin. The OHC's mechanical response to voltage change is accompanied by a "gating current," manifested as non-linear capacitance. This nonlinear capacitance was also demonstrated in transfected TSA201 cells.

The materials and methods used in the experiments presented herein are now described.

Mature gerbils were euthanized and the organ of Corti and associated basilar membrane were isolated by dissection as described in He et al.(1997, J. Neurosci., 15:3634–3643). The tissue was placed in calcium-free S-MEM medium, followed by brief trypsin treatment (1 milligram per milliliter) and trituration (20 minutes at 37 degrees Celsius). OHCs and IHCs were isolated in a low-calcium solution. Single OHCs and IHCs were identified and separated based on the presence of particular stereocilia configuration, depicted in FIG. 12. Using a glass pipette, the cells were separately isolated based on their morphological appearance and were collected in lithium chloride buffer. Messenger RNA was isolated from tissue using 20 microliters of oligo-dT magnetic beads (Dynal, Oslo, Norway). cDNA pools were created with Superscript II RNAase H reverse transcriptase (Gibco BRL, Gaithersburg, Md.) followed by amplification using a 5'-cap and oligo dT-dependent PCR technique according to manufacturer's specifications (SMART PCR™, Clontech, Palo Alto, Calif.). These cDNA pools were used for PCR subtractive hybridization, qualitative PCR, and virtual Northern (cDNA) dot-blot hybridization experiments.

The PCR subtractive hybridization procedures, control reactions, and subcloning were according to the manufacturer's instructions (PCR Select cDNA Subtraction Kit, Clontech). Clones were subjected to a differential screening procedure using a PCR-Select Differential Screening Kit (Clontech). PCR amplified cDNA inserts from these clones were denatured and vacuum filtered onto four identical nylon membranes. Each cDNA sample was separately hybridized with one of the following probes: forward subtracted (OHC—IHC) cDNA; reverse subtracted (IHC—OHC) cDNA; un-subtracted OHC cDNA; and un-subtracted IHC cDNA. These cDNA pools were random primed labeled with [$^{32}$P]-dCTP and hybridized to the blots. Positively hybridizing clones were scored for differential hybridization with forward (OHC—IHC) and reverse (IHC—OHC) subtracted probes. This differential expression was confirmed by correlation with simultaneous differential hybridization with the original un-subtracted OHC and IHC cDNA pools. Sequencing was performed using dRhodamine terminator cycle sequencing ready reaction kit (ABI Prism, Foster City, Calif.) and an automated DNA sequencer (Model 377, Perkin Elmer, Norwalk, Conn.). DNA and amino acid sequences were compared and analyzed using sequence analysis software of GCG and TMHMM (1998, Sonnhammer, et al., Proc. 6$^{th}$ Intern. Conf. On Intelligent Systems for Mol. Biol., 175–182) and Tmpred (1993, Hoffmnan, et al., Biol. Chem., 347:166).

Virtual Northern (cDNA) Dot-blot Hybridization 0.5 Micrograms of SMART™ cDNA from gerbil thyroid, IHC, OHC, and 0, 6, 12, 16, and 20 day old organs of Corti were denatured and vacuum filtered onto membranes. A 1067 base pair NcoI restriction fragment of Pres cDNA was radioactively labeled with [$^{32}$P]-dATP and used as a probe (Strip-EZ Kit™ and UltraHyb™ buffer, Ambion, Austin Tex.).

PCR

PCR reactions used templates of 200 nanograms of SMART™ cDNA from gerbil thyroid, newborn and adult organs of Corti, isolated IHC, and organ of Corti from various post-natal ages (0 to 20 days after birth). Pres-specific primers (sense: 5'-TACCTCACGGAGCC-GCTGGT-3' (SEQ ID NO:7), and antisense: 5'-GCAGTAATCAGTCCGTAGTCC-3' (SEQ ID NO:8)) were used to amplify an 863-base pair fragment from the cDNA. Cyclophilin primers (sense: 5'-TGG-CACAGGAGGAAAGAGCATC-3' (SEQ ID NO:9), and antisense: 5'-AAAGGGCTTCTCCACCTCGATC-3' (SEQ ID NO:10)) that amplify a 301-base pair DNA fragment were used as an internal control. Cycle parameters were 3 minutes at 94 degrees Celsius followed by 25–30 cycles of 94 degrees Celsius for 45 seconds, 56 degrees Celsius for 45 seconds, and 72 degrees Celsius for 1 minute, with a final extension at 72 degrees Celsius for 10 minutes.

Transient Transfection

TSA201 cells, clones of human embryonic kidney 293 cells that express the simian virus 40 (SV40) large T-antigen in a stable manner, were cultured in DMEM with 5% fetal calf serum, 100 units of penicillin per millilter, and 100 micrograms of streptomycin per milliliters. Cells were plated for 24 hours before calcium phosphate transfection. The transfection reaction mixture contained:

a) control plasmid, pcDNA3.1; b) 2 micrograms of Pres cDNA plasmid; c) 2 micrograms of Pres cDNA plasmid plus 0.2 micrograms of green fluorescent protein (GFP) plasmid as transfection marker; or d) 2 micrograms of pendrin cDNA plasmid plus 0.2 micrograms GFP plasmid.

After 24 hours the transfected cells were used for electrophysiological and physical measurements. Large, rounded, non-clustered TSA201 cells exhibiting considerable granulation were selected for electrophysiological and motility experiments.

Capacitance Measurements

Whole-cell voltage-clamp recordings were made with an Axopatch™ 200B amplifier (Axon Instruments, Foster City, Calif.) Recording pipettes had open tip resistances of 2–3 megaohms and were filled with internal solution containing 140 millimolar CsCl, 2 millimolar MgCl$_2$, 10 millimolar EGTA, and 10 millimolar HEPES at pH 7.2. The external solution contained: 120 millimolar NaCl, 20 millimolar TEA-Cl, 2 millimolar CoCl$_2$, 2 millimolar MgCl$_2$, 10 millimolar HEPES, and 5 millimolar glucose at pH 7.2. Osmolarity was adjusted to 300 milliosmolar per liter with glucose. Capacitive currents were filtered at 5 kilohertz and digitized at 50 kilohertz using pClamp 7.0 software (Axon Instruments).

Voltage-dependent capacitance was measured using two methods. First, a standard P/4 linear subtraction procedure was employed to detect the presence of nonlinear charge movement. After nonlinear transient current was detected, a stair-step voltage protocol was used to obtain the parameters of charge movement. For each voltage step, the measured membrane capacitance ($C_m$) was plotted as a function of membrane voltage ($V_m$) and fitted with the derivative of a Boltzmann function:

$$C_m = \frac{Q_{max}\alpha}{\text{Exp}\,[\alpha(V_m - V_{1/2})](1 + \exp[-\alpha(V_m - V_{1/2})])^2} + C_{lin} \quad (1)$$

where Qmax is maximum charge transfer, $V_{1/2}$ is the voltage at which the maximum charge is equally distributed across the membrane, $C_{lin}$ is linear capacitance, and $\alpha = ze/kT$ is the slope factor of the voltage dependence of charge transfer where k is Boltzmann's constant, T is absolute temperature, z is valence, and e is electron charge. From the stair-step analysis we have obtained the membrane resistance: $R_m = 130.45 \pm 20.14$ megaohms.

Motility Measurements

Figure 6A:
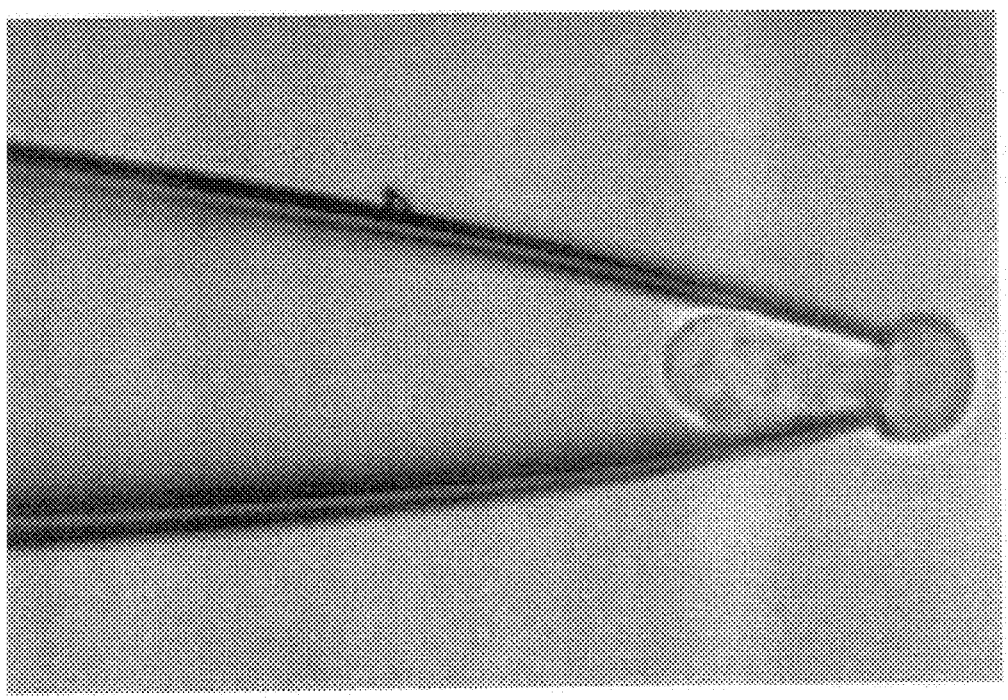
FIGS. 6A–6E, depicts examples of voltage-dependent motility expressed in TSA201 cells.

TSA201 cells were drawn into a microchamber with gentle suction (FIG. 6A). The microchamber was mounted on a three-dimensional micromanipulator attached to the stage of a Zeiss inverted microscope. The most distal part of the excluded segment of the cell was imaged onto a photodiode with a rectangular slit interposed into the light path. A change of photocurrent signified cell extension or contraction. The signal was current-to-voltage transformed, amplified, A/D converted, and averaged. The command voltage, delivered between the electrolyte solutions (L15, Gibco BRL) surrounding and filling the microchamber, produces different voltage drops on the included and excluded cell membrane segments, determined by the electrical voltage-divider effect of these membranes. During motility measurements, the location of the cell within the slit was monitored via a video camera placed behind the slit. The appearance of the whole cell in the microchamber was also continuously displayed with the aid of a second video camera. This permitted an independent verification of a lack of movement of the microchamber itself.

The results of these experiments are now described.

Cloning of Pres and the Properties of Prestin

The molecular approach to identify the OHC sensor-motor protein faced two initial challenges: first, isolation of cDNA from limited amounts of biological material, and second, recognition of the candidate motor protein cDNA among the isolated unknown genes. Isolation of sufficient number of OHCs is a fairly routine task.

Obtaining comparable numbers of IHCs requires some modification of techniques. mRNA was isolated from approximately 1000 OHCs and 1000 IHCs and reverse transcribed followed by 5'-mRNA cap and oligo dT-dependent PCR amplification to obtain OHC and IHC cDNA pools.

Recognition of the cDNAs that encoded the candidate motor protein was based on the following assumptions: (1) the protein is expressed in OHC and not in the non-motile IHC, (2) ontogenic expression should relate to the known development of electromechanical responses, (3) the protein should be relatively abundant in OHC, (4) the protein should be a transmembrane protein, and (5) electromechanical responses should be demonstrable when expressed in a heterologous system. It was reasonable to expect that gene expression related to mechano-electric transduction and genomic, metabolic, and structural functions would be shared by these two types of hair cells. Therefore suppression subtractive hybridization PCR procedure was used to amplify and enrich the OHC cDNA pool for uniquely expressed gene products. This procedure uses two rounds of cDNA hybridization to subtract out common OHC cDNAs using a vast excess of IHC cDNA. The unique fragments are amplified by PCR, RsaI-digested, and cloned to create a library of candidate clones. This technique is useful because it simultaneously enriches for differentially expressed cDNA fragments and suppresses non-target DNA amplification.

Approximately 1300 fragment clones were screened using four cDNA pools (OHC—IHC, IHC—OHC, OHC unsubtracted and IHC unsubtracted) to identify differentially expressing clones (FIG. 1). Once false positive clones were excluded, 487 clones were identified as differentially expressing genes and of these, 108 clones were sequenced. These 108 sequences contained 50 unique cDNA fragments. Eighteen of the clones contained sequences which were highly similar to known proteins including Type I collagen pro-alpha 2, serine kinase, oncomodulin, ribonucleotide reductase, ATP synthase, etc., while 32 were believed to be unique in that there were no obvious homologous sequences to them in the genetic database searched. Eleven of the 32 apparently unique clones contained DNA having open reading frames. These were examined in greater detail by dot-blot hybridization using radioactively labeled clone cDNA against immobilized OHC and IHC cDNA pools. Pres was one of the eleven candidate clones identified. Pres fragments in the PCR subtracted library were abundant (>10% of 487 differentially expressed clones) and demonstrated consistent differential hybridization with OHC and IHC derived probes (FIG. 16).

Using one of these Pres cDNA RsaI fragments as a probe, three cDNA clones were subsequently isolated from a gamma-gt11 gerbil adult cochlea library. The largest of these clones was 4.1 kilobases in length having an open reading frame of 2232 base pairs, encoding a 744 amino acid-protein (FIG. 2). The sequence around the putative translation start site contains a consensus Kozak sequence and an in-frame stop codon is present 12 bases upstream of this predicted start site. There is a short 223 base pair untranslated 5' end and a large 1654 base pair, 3' untranslated region. A computer search of the Pres sequence revealed that about one-third of the human PRES gene has been fortuitously sequenced as part of the human chromosome 7 effort (BAC clone RG107G13, bases 99,895 to >113,558). The amino acid homology between human and gerbil prestin, deduced from the genomic sequence of the first 6 exons, is 98% (FIG. 2).

Analysis of the prestin sequence revealed that its highest homology was to members of a family of anion/sulfate transport proteins including pendrin and DRA. The pendrin homology (40%) is of particular interest because this chloride-iodide transport protein is known to be a cause of the genetically inherited deafness observed in Pendred's syndrome. This homology, although modest overall, is similar to the homology among other members of the sulfate/anion transport family. Because gerbil cDNA was used and only rat, mouse, and human pendrin sequences were known at the time, it was necessary to demonstrate that prestin was not the gerbil homolog of pendrin.

It has been shown by others that mouse pendrin is expressed in the endolymphatic duct and sac, the utricle and saccule, and within the cochlea only in the external sulcus, but not in the organ of Corti. Confirmation that prestin was not a gerbil homolog of pendrin was achieved by cloning an 824 base pair fragment of gerbil pendrin cDNA, and demonstrating that the sequence was distinct from prestin. The gerbil pendrin amino acid sequence derived from the above cDNA fragment was 88% homologous to the amino acid sequence of human pendrin, but only 38% homologous to the amino acid sequence of gerbil prestin.

The protein prestin (744 amino acids; 81.4 kiloDaltons) is hydrophobic, containing approximately 50% non-polar residues; 27.8% of the protein is composed of the amino acids valine, leucine and isoleucine. Computer modeling of the amino acid sequence produces ambiguous results using multiple modeling programs. Specifically, the models TMHMM and TMPred report ambiguous results as to the number and location of transmembrane regions and are unable to predict the topology of the amino and carboxy termini in relation to the membrane. By comparison, when pendrin is subjected to the same modeling programs, 11 transmembrane regions, and an intracellular amino terminus are unambiguously predicted. The consistent ambiguity of the modeling programs with regard to prestin is potentially significant, and suggests that the mechanism by which prestin produces electromechanical action is by altering the protein/membrane interface as a result of voltage induced changes in its structure.

Two distinctive charged regions are located in the carboxy terminal region of prestin. A positive charge cluster of residues is located at 557–580; adjacent to the positive cluster, a negative charge cluster is at residues 596 to 613 (FIG. 2). Prestin's overall predicted hydropathy profile is similar to pendrin, DRA, and other members of the sulfate/anion transport family. The homology to pendrin is highest in the 50 amino acid region (97–146) that encompasses the sulfate transport motif (109–130), but does not have long regions of amino acid identity elsewhere. Instead, there is a pattern of moderate homology using both amino acid identity and similarity throughout the protein with multiple, discrete 8–12 residue segments of amino acid identity. The charged cluster regions of prestin are conserved in their net charges, but are otherwise not remarkably homologous. The proteins differ most in the region between the two charge clusters and at the termini. Although prestin exhibits high homology in the sulfate transport region, a highly conserved domain, found in homologs in organisms as distant as yeast, C. elegans, and plants, does not conform to the sulfate transporter signature as currently defined. Specifically, both human and gerbil prestin differ from the consensus sequence at three positions (FIG. 3). Consequently, while prestin appears related to sulfate transporters, these differences in the conserved region suggest that the protein may have distinct properties.

Figure 1A:
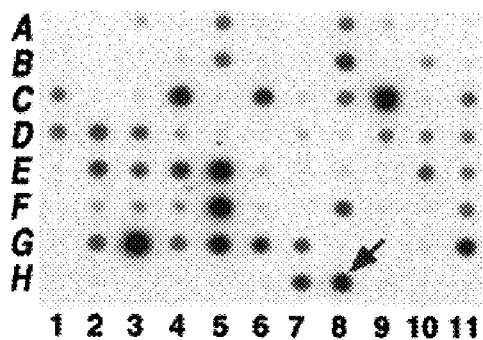
FIGS. 1A–1D, is a quartet of images depicting the results of subtractive hybridization experiments. Identical cDNA was fixed to each of the 4 blots and separately hybridized with radioactive probes.
Figure 1B:
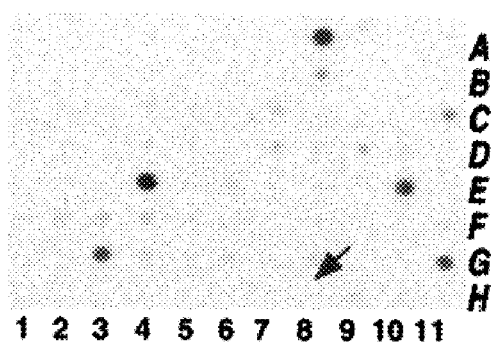
Figure 1C:
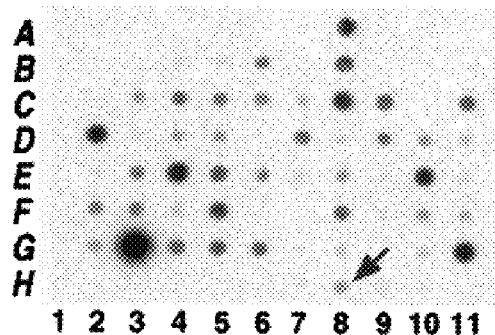
Figure 1D:
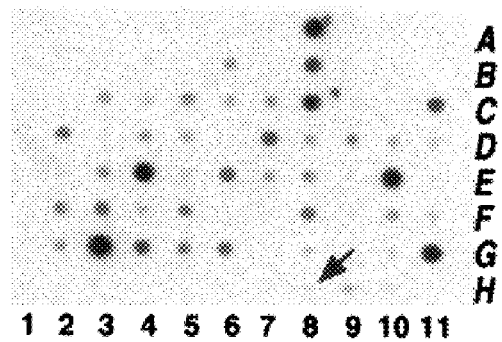
Figure 4A:
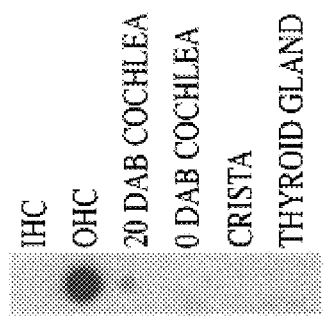
FIGS. 4A–4D, represents an analysis of pres gene expression.
Figure 4B:
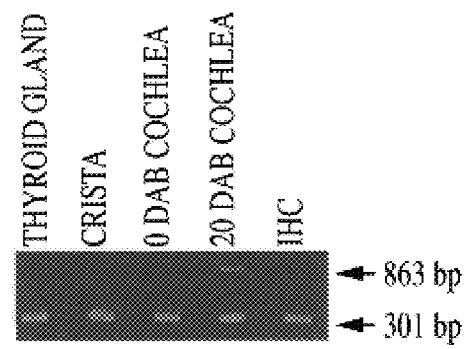
Figure 4C:
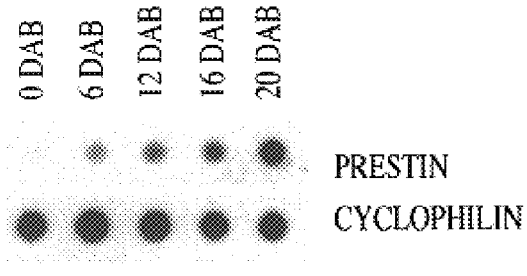
Figure 4D:
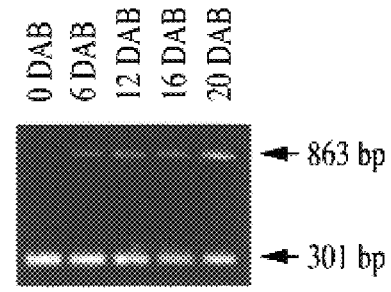

The tissue-specific and developmental expression pattern of Pres in the gerbil was also determined. Northern blot analysis using a Pres probe did not detect expression of prestin in liver, lung, brain, spleen, ovary, kidney, muscle, and heart (total RNA 20 micrograms). Virtual Northern dot-blot analysis using cDNA prepared from IHC, OHC, mature and newborn organs of Corti, and thyroid revealed prestin expression only in mature OHC and 20 day old organ of Corti (FIG. 4A). Similar results were obtained using Pres-specific primers and a qualitative PCR assay (FIG. 4B). Both virtual Northern and PCR exhibited progressively increasing Pres expression in isolated organ of Corti from birth up to 20 days after birth (FIGS. 4C and 4D), by which time electromotility is fully developed in the altricial gerbil. In OHCs, the motors are usually congruent with abundant approximately 10 nanometer membrane particles. The density of these particles in gerbil OHCs increases with development which density then decelerates toward adult values 16–18 days after birth. Thus the ontogenic expression of Pres is similar to that of membrane particles, electromotility, and the onset of high sensitivity hearing.

Functional Tests of Prestin

In order to investigate the function of the prestin cDNA, the functional properties of prestin in eukaryotic cells were examined. To accomplish this, Pres was subcloned into the eukaryotic expression vector pcDNA3.1. A carboxy-terminal epitope-tagged (V5) version (pcDNA6/V5-HisA vector) of the expression vector was created to facilitate detection of expression of the full-length protein in transfected cells. The expression of the V5 version was examined by indirect immunofluorescence to assure its presence in transfected cells. The epitope-modified prestin was found to be located in the cell membrane, with a punctate distribution in permeabilized cells. In addition, Western blot analysis using an anti-V5 antibody against transfected cell extracts demonstrated production of the appropriate sized prestin protein.

Figure 5A:
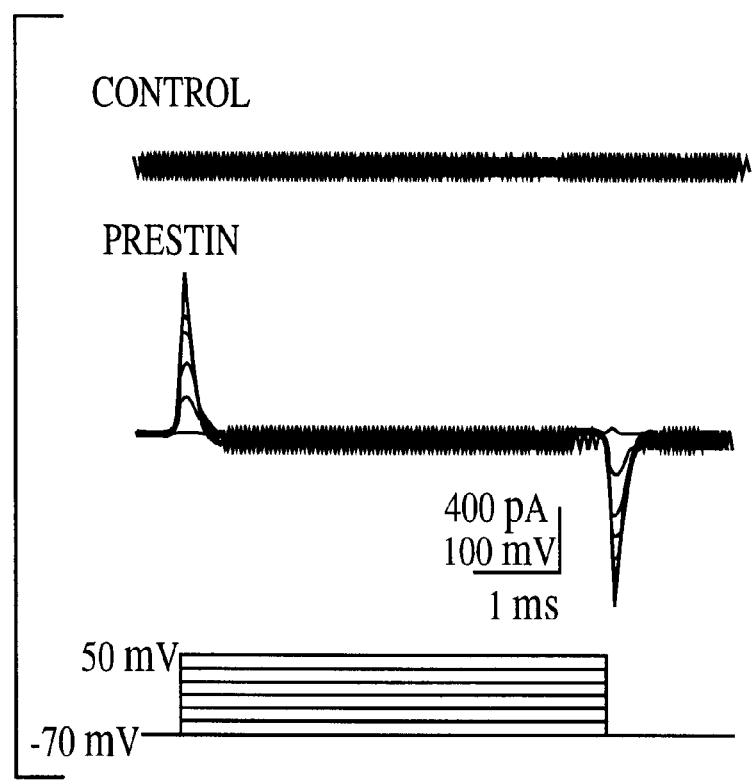
FIGS. 5A–5D, depicts the voltage-dependent charge movement in TSA201 cells. All recordings were within 24–60 hours of transfection.
Figure 5B:
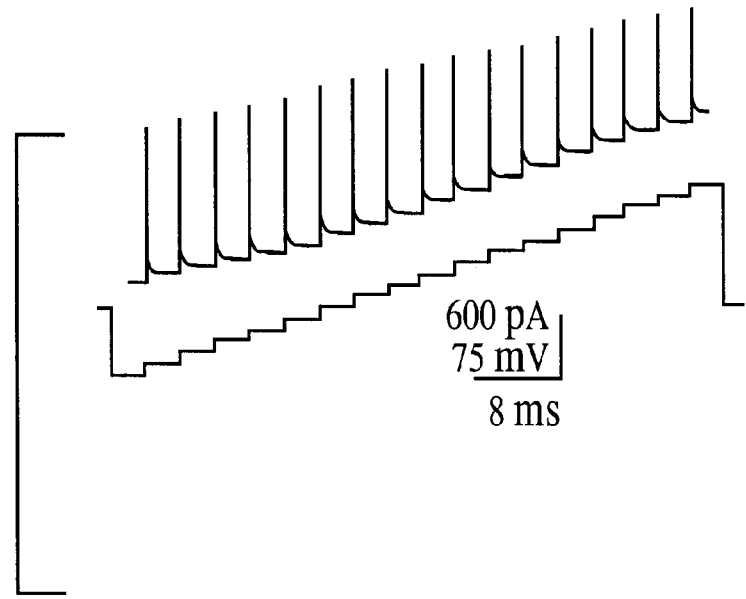
Figure 5C:
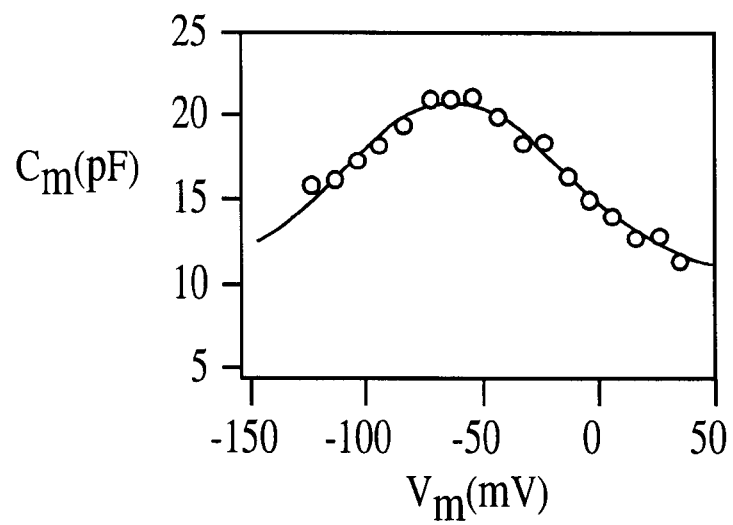

To test the sensor-motor function of prestin, voltage-dependent charge movement was measured in TSA201 cells after transient transfection of unmodified, native Pres cDNA. A second plasmid (pEGFP-N2) containing GFP cDNA was used as an independent marker for successful transfection of the cells. Transfection efficiency was 30–40% as judged from the fluorescence of GFP in transfected cells. Consistent with this, 36.8% of cells transfected with Pres alone displayed transient capacitive currents under voltage clamp using a standard subtraction protocol after blocking ionic currents (FIG. 5A). In experiments conducted on cells co-transfected with prestin and GFP cDNA, transient capacitive currents were obtained from 91.8% of the GFP positive cells. In contrast, untransfected cells or cells transfected solely with the control plasmid exhibited no measurable nonlinear capacitance. The capacitive currents were directed towards the outside as the membrane potential was depolarized and toward the inside as it was hyperpolarized. Charges transferred at command onset and offset were approximately equal. The decay of transient currents was rapid (100–200 microseconds) and could be well-fitted with a single exponential. The voltage protocol used to estimate membrane capacitance and charge transfer across the membrane was an ascending stair-step voltage waveform (FIG. 5B). The membrane capacitance was fitted to the derivative of a first-order Boltzmann equation (FIG. 5C). In a group of seven cells, these curve-fits yielded values of $Q_{max}=1.76\pm0.20$ pC, $V_{1/2}=-57.30 \pm 2.98$ mV, $1/a\sim=kT/ze=28.00\pm2.13$ mV, and $C_{lin}=20.50\pm2.65$ pF, respectively (mean±SEM). The valence can be calculated from a, $z=0.91$. The average charge density, a possible measure of transiently transfected motor protein density in TSA201 cells, was 5360 square micrometers. The numerical values that characterize the charge movement ($V_{1/2}$, z) are quite similar to those obtained for OHCs. The maximum charge and charge density are less in the transfected cells, even though the linear capacitance is about the same as that of an average OHC.

Figure 5D:
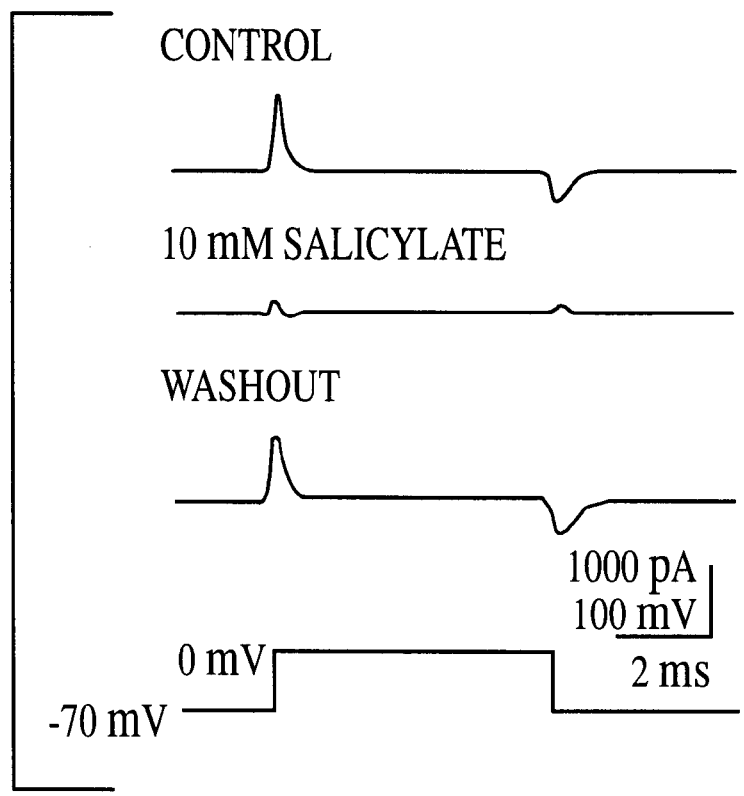

In OHCs, nonlinear capacitive current and electromotility can be reversibly blocked by sodium salicylate. As further evidence that transient currents stem from the transfected motor protein, salicylate was locally applied to cells that had been shown to present charge movement. Sodium salicylate (10 millimolar) reduced the transient currents to 15.5±2.9% of control (FIG. 5D). Of these, 3 cells showed recovery after 2–5 minutes of washing in normal extracellular solution without sodium salicylate (to 88.4±8.8% of control).

Finally, the existence of nonlinear capacitance was tested in cells that were transfected with both GFP and human pendrin CDNA. None of the GFP-positive cells demonstrated nonlinear capacitance. This result is significant because of the similarity of pendrin and prestin, demonstrating the specificity of the candidate motor protein. It also indicates that the electrophysiological results are not simply the consequence of the introduction of an anion transport protein.

Figure 6B:
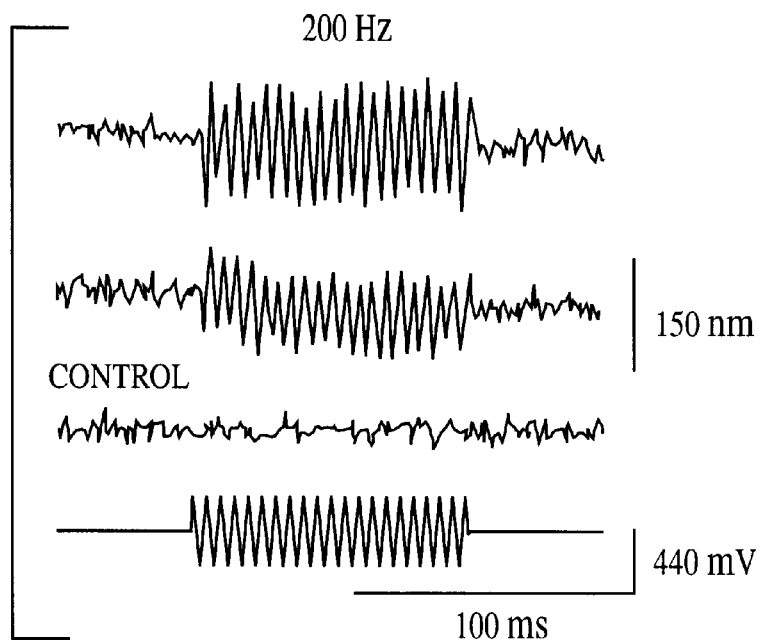
Figure 6C:
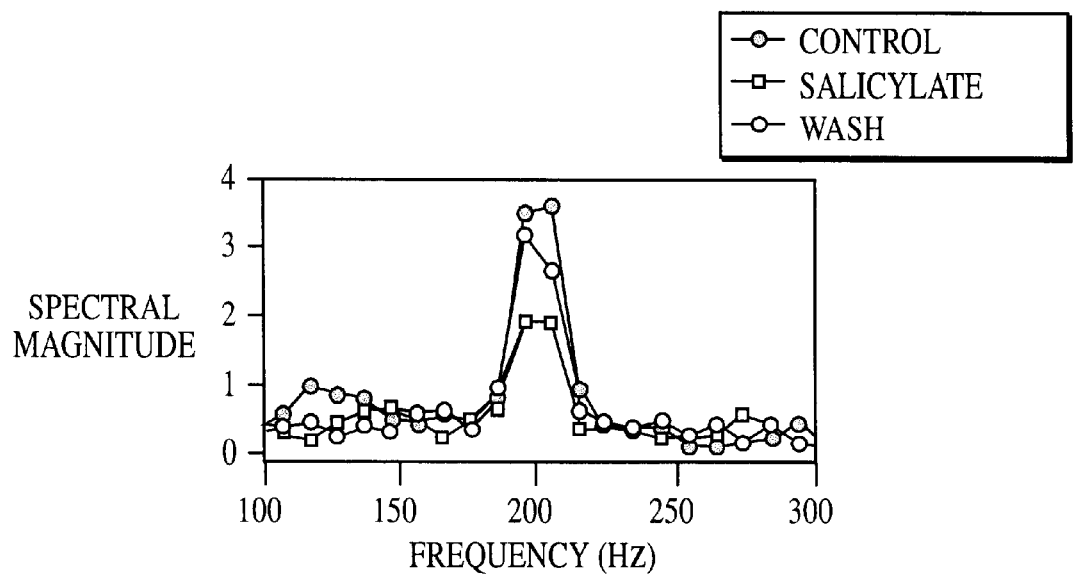
Figure 6D:
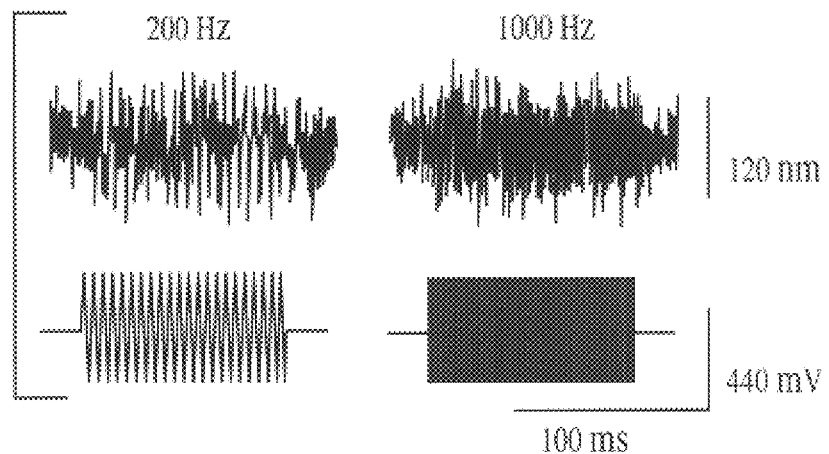
Figure 6E:
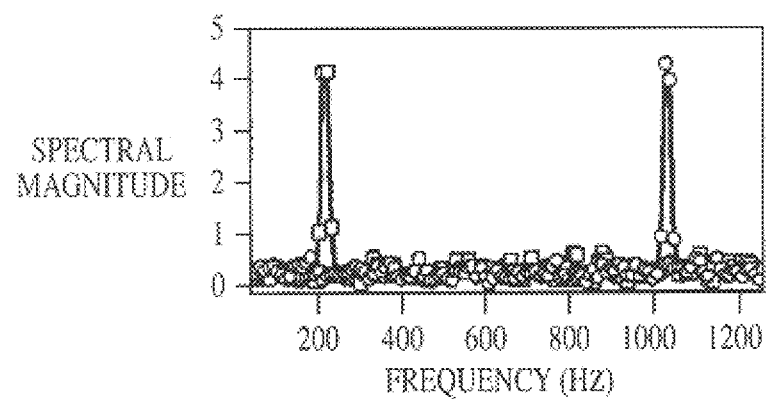
Figure 11:
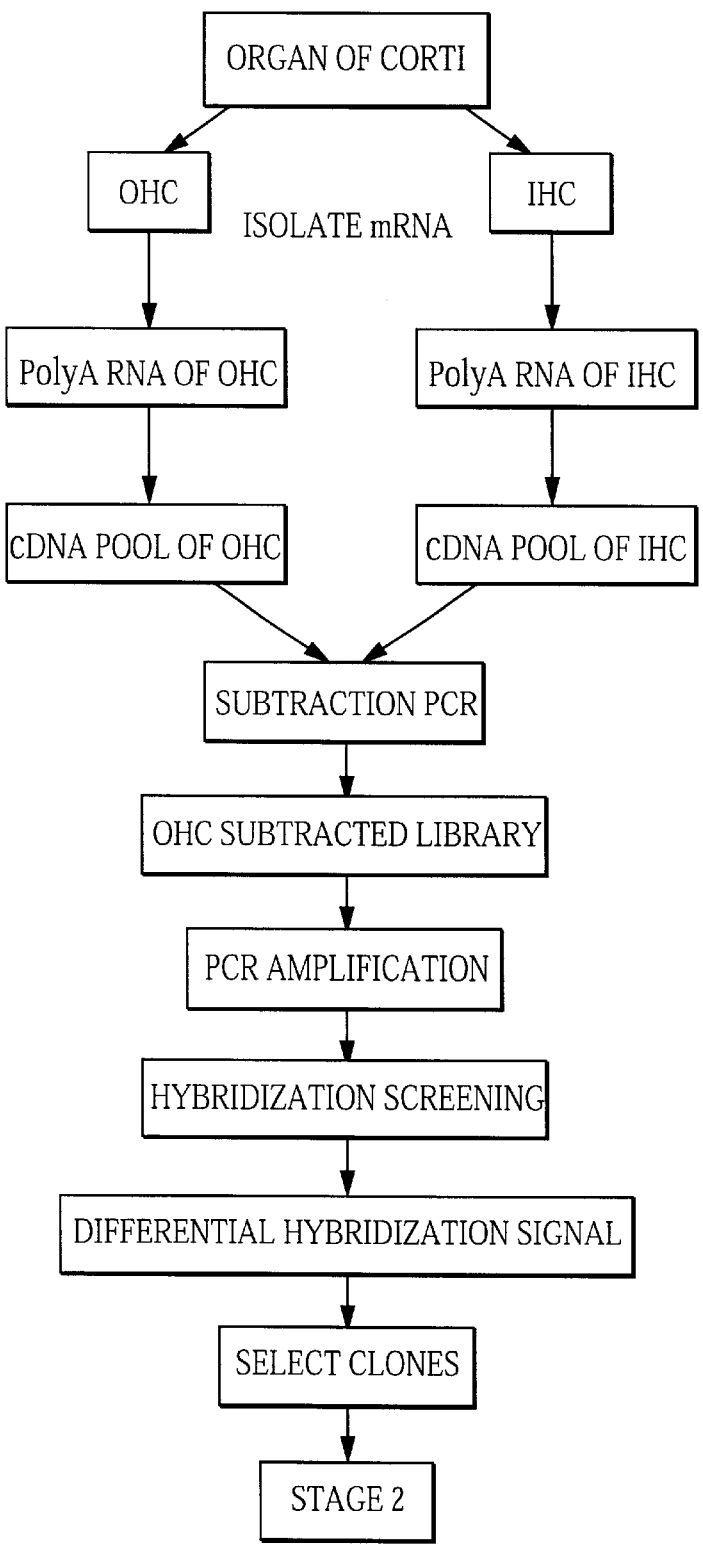
FIG. 11 is a schematic diagram depicting Stage 1 of the procedure for establishing the OHC subtracted library. After obtaining poly A RNA from each of the OHCs and IHCs, 5'-cap reverse transcription oligo-dT dependent PCR is performed to obtain the cDNA pools of each of the OHCs and IHCs. After the hybridization screening, the cDNA can be reverse or forward subtracted or subtracted using tester or driver cDNA alone.

In TSA201 cells the organized cytoskeletal network is probably missing, thereby making the conversion of mechanical molecular events to gross cellular deformation more difficult. Consequently, even if the motor protein is expressed, gross cellular deformation is expected to be very small. Furthermore, OHCs are efficient producers of axial motility because of their cylindrical shape. Fast mechanical effects occur at constant cell volume and are generally assumed to be the result of a change in cell surface area, due to the aggregate conformational shape changes of large numbers of motor proteins. A spherical cell cannot change its surface area while its volume remains constant, whereas a cylindrical cell can. In order to test that the generally spherical TSA201 cells may produce measurable motility, the cells were distorted to alter their shape by drawing them into a suction pipette (microchamber), thereby producing a dumbbell or hourglass shape (FIG. 6A). Electromotility in about 22% of cells tested was demonstrated. Two of the best responses are shown in FIG. 6B, in contrast to a trace from a non-transfected, non-responsive cell. The usual electrical driving signal was a brief 200 Hertz sinusoid. Sodium salicylate produces a reversible decrease in the electromotile response (FIG. 6C), just as it does in OHCs. In order to examine motility at higher frequencies, comparison between responses at 200 and 1000 Hertz are shown in FIGS. 6D and 6E. When corrected for the characteristics of the recording system, the two responses are essentially identical (FIG. 6E), in accord with OHC data obtained in the past.

The protein prestin has been shown to convey to a heterologous system novel mechanical responsiveness, almost indistinguishable from that measured in OHCs A portion of the human pres gene has been sequenced and mapped. The location of the motor protein in relation to the other members of its family can be predicted and any relationship to genetic loci known to be related to hearing disorders or deafness can be ascertained. The bacterial artificial chromosome clone (RG107G13) which contains a portion of the pres gene at its 3' end, has a single known other gene, RELN, which is about 50 kilobases centromeric to the pres gene fragment. This location is approximately 3.7 megabases centromeric to the location of the pendrin (PDS) and DRA genes. Thus, it appears likely that pres is located in an as yet unsequenced portion of 7q31, centromeric to PDS and DRA, and 50 kilobases telomeric to the RELN gene.

There are at present two autosomal nonsyndromic recessive deafness loci mapped to 7q31 in addition to the PDS gene: DFNB14 and DFNB17. DFNB14 is the most likely candidate to be pres, since it maps centromeric to the PDS gene locus, while DFNB17 maps to the telomeric side of PDS and DRA. The proof that DFNB14 is itself distinct from PDS is derived from the fact that, in the kindred analyzed, there were no useful polymorphic markers in a genomic region of 15 centimorgans that contains both the RELN gene and PDS. In this kindred, the PDS exons were sequenced and appeared to be normal, indicating that the causative mutation was distinct from that seen in Pendred's syndrome. The clinical phenotype in this kindred of a congenital, sensorineural, autosomal recessive form of non-syndromic deafness, is consistent with prestin's functional role.

These results support earlier work on OHCs, demonstrating that neither the subsurface cortical lattice nor the subsurface cisterns are essential for electromotility. It is unlikely that either of these organelles would be present in TSA201 cells, either in their native or transfected form. Demonstration of nonlinear capacitance and motility simplifies the concept of electromechanical changes in OHCs and obviates the need for exotic schemes. Presumed conformational changes of prestin, resulting in a change of cell surface area, produce dimensional changes in the cell. This is the basic electromotile response. It is contemplated that stiffness change may accompany these shape changes in TSA201 cells as they do in OHCs, thus the expression of prestin plays a role in the full electromechanical process.

While the reliance of the mammalian cochlea on local, OHC-based, amplification is widely accepted, there is no universal agreement about the amplifying mechanism. One view is that, powered by the cell's receptor potential, OHC electromotility provides mechanical feedback and thereby amplification. This view places the motor process in the cell's basolateral membrane and calls for a novel motor protein to drive somatic shape changes. An alternative concept is that amplification arises as a byproduct of the cell's forward transducer process and thus resides in the stereocilia. Whichever mechanism dominates, the existence of electromechanical action in OHCs is indisputable. The novel pres gene herein identified is the gene that codes for a specialized motor protein that produces this electromechanical action when expressed in cells that, in their native form, do not exhibit this phenomenon.

Isolated OHCs are capable of producing an average maximum axial isometric (stall) force of approximately 6 nanoNewtons (2000, He and Dallos, JARO, 1:64–81). From the number of molecules producing this force it can be estimated that the individual molecular stall force is on the order of 2.4 picoNewtons. In comparison, the stall force of kinesin is 5 to 6 picoNewtons. The potential of prestin to perform as a fast, voltage-driven actuator, individually or in assemblies, forming the basis of futuristic nanomachinery, is substantial.

Example 2: Isolation of a Novel Gene from Gerbil Outer Hair Cells

The materials and methods for the experimental procedures employed in this Example are now described. The methods are similar to those employed for Example 1.
Isolation of Outer Hair Cells (OHCs) and Inner Hair Cells (IHCs)

Mature gerbils were decapitated immediately following euthanasia. The organ of Corti and the associated basilar membrane were then treated with XX milligrams per milliliter of trypsin for 20 minutes at 37 degrees Celsius. OHCs and IHCs were obtained by gentle trituration of the trypsinized organ of Corti and the basilar membrane. The preparation was mounted on an inverted microscope as described in He, et al (2000, Hearing Res., 145:156–160).

Figures 12A, 12B, 12C, 12D:
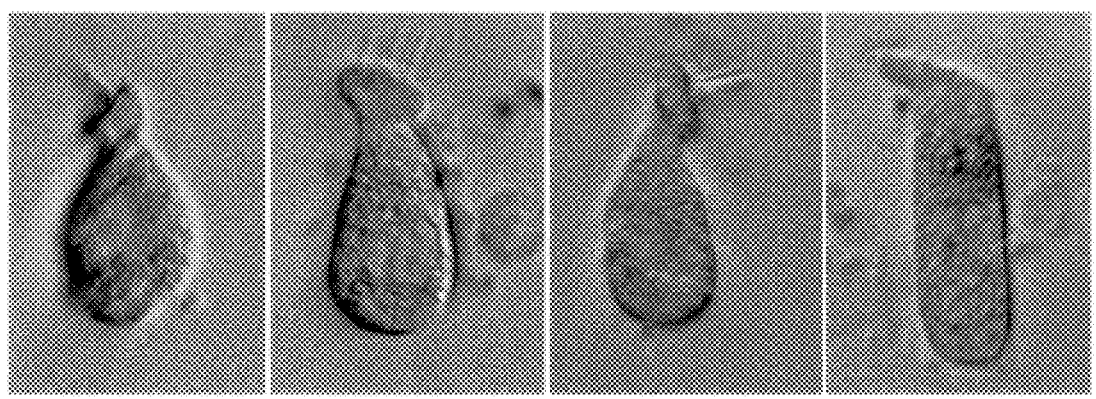
FIGS. 12A–12D, is a quartet of images depicting IHCs and OHCs isolated from adult gerbil cochlea. Note the differences in stereocilia configuration.
Figure 13A:
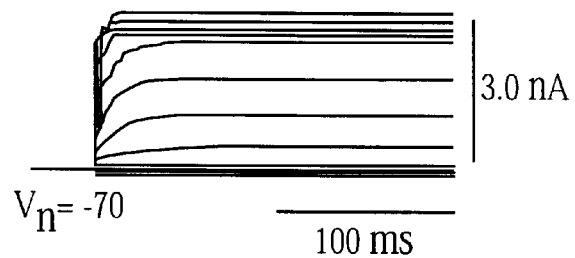
FIGS. 13A, 13B, and 13C, is a series of images depicting the typical whole-cell current responses recorded in OHCs (FIG. 13A) and IHCs (FIG. 13B).
Figure 13B:
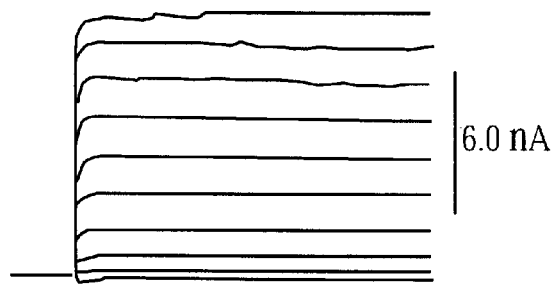
Figure 13C:
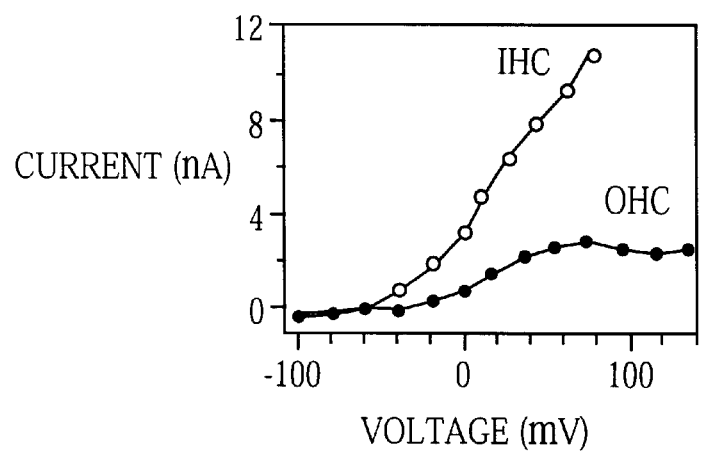
Figure 14:
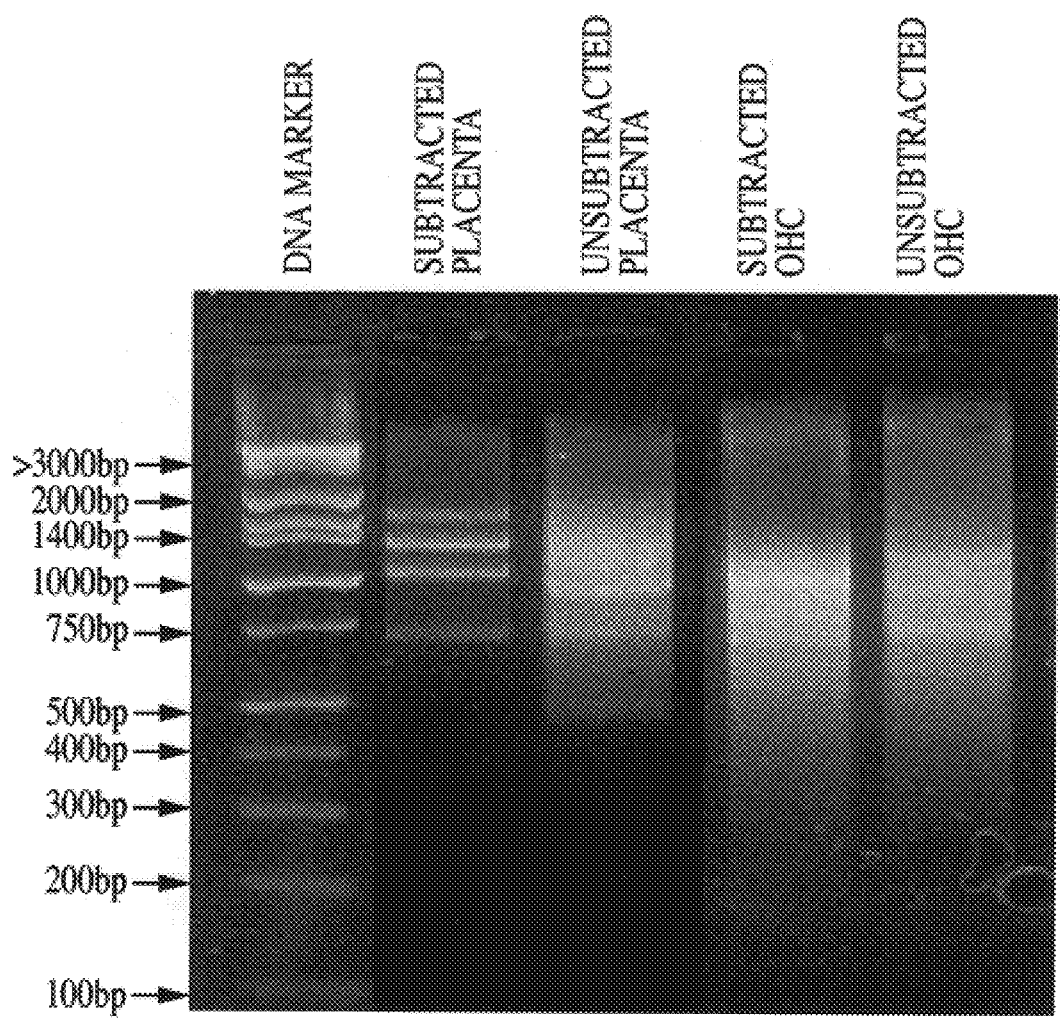
FIG. 14 is an image of an agarose gel stained with ethidium bromide. The image depicts subracted cDNA pools prior to cloning. Forward-subtracted cDNA is compared to unsubtracted cDNA.
Figure 15:
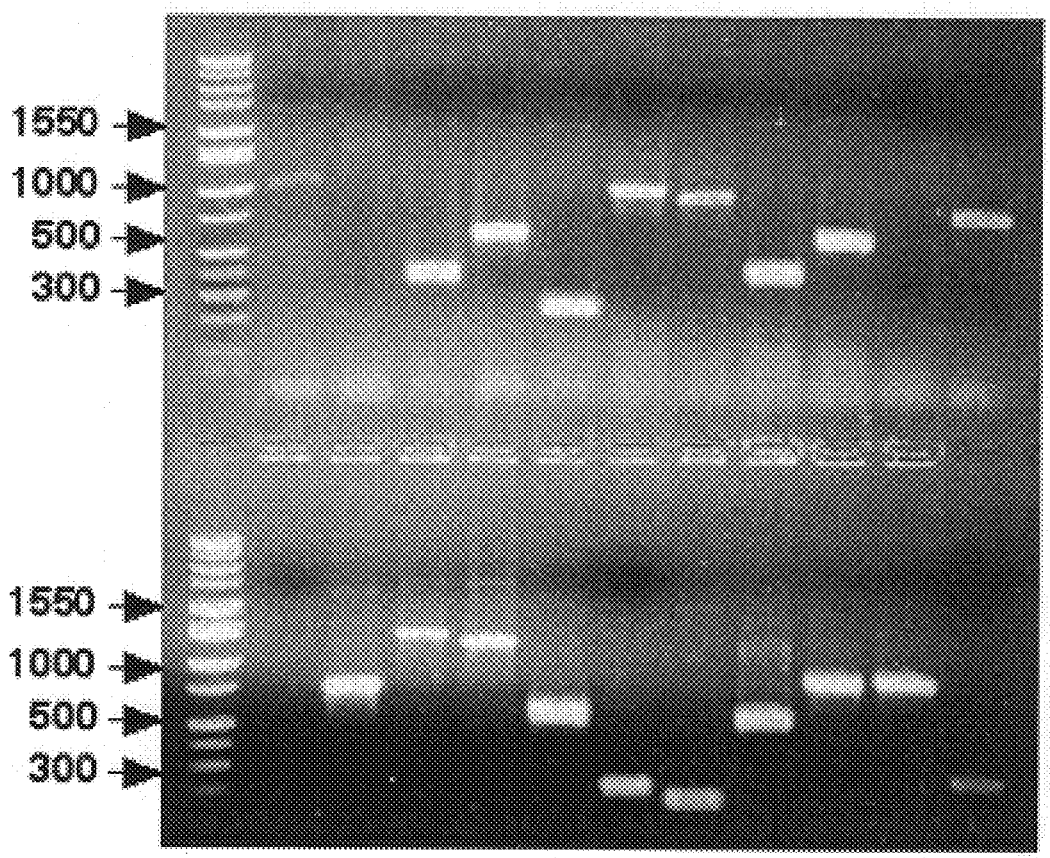
FIG. 15 is an image depicting amplification and size determination of cloned OHC—subtracted cDNAs. These cDNAs were used for the hybridization screening analysis depicted in FIG. 16.
Figure 16A:
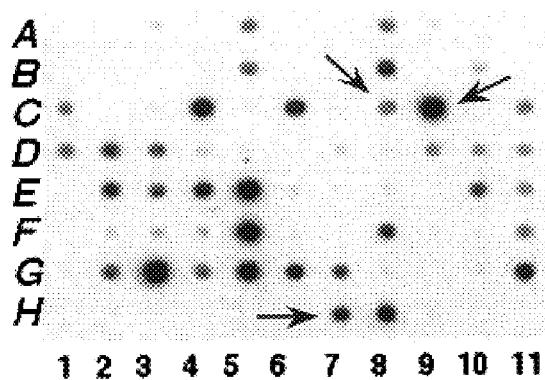
FIGS. 16A–16D, is a series of cDNA hybridization dot-blot assays. These blots demonstrate differential hybridization of the cloned, subtracted OHC cDNAs shown in FIG. 15.
Figure 16B:
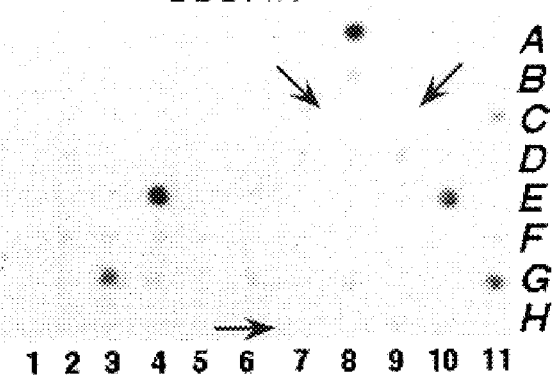
Figures 16C, 16D:
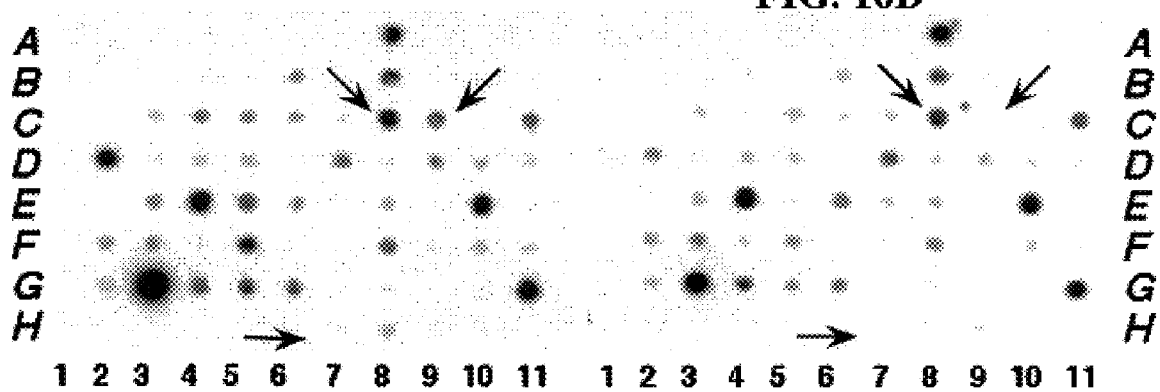
Figure 17:
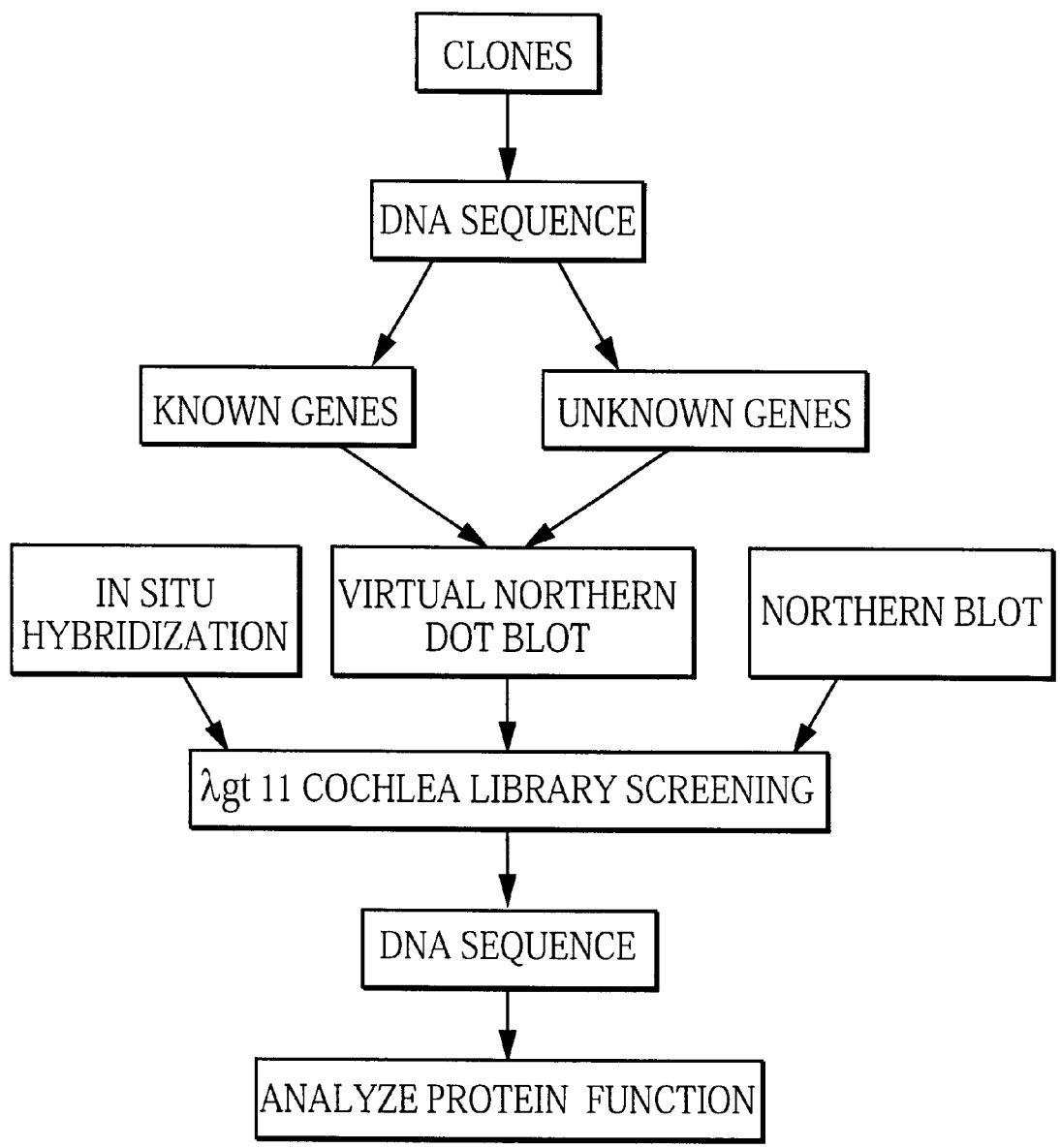
FIG. 17 is a schematic diagram depicting Stage 2 of the procedure for analyzing an OHC subtracted library.

Solitary OHCs and IHCs were identified by appearance and by the presence of a particular stereocilia configuration, shown in FIG. 12. OHCs and IHCs were then separately isolated by a small glass pipette (30–50 micrometers in tip diameter) mounted on a three dimensional stage micromanipulator. Approximately 1,000 IHCs and 1,000 OHCs were collected from 7 animals.
PCR Amplification Messenger RNAs were isolated from both OHCs and IHCs using 40 microliters of oligo-dT magnetic beads in Lithium Chloride buffer (Dynal). OHC and IHC cDNA pools were created by reverse transcription using 200 units of Superscript II RNAase H reverse transcriptase at 42 degrees Celsius for one hour, followed by amplification with a 5'-Cap and oligo dT-dependent PCR technique according to manufacturer's instructions (Clontech).
PCR-Select cDNA Subtraction In the subtraction experiment, OHC is the tester cDNA, and IHC is the driver cDNA. The OHC cDNA pool generated from PCR amplification was divided into two groups and then ligated to two different adapters (adapter 1 and 2). The OHC cDNAs were then subjected to two rounds of subtractive hybridization with excess driver cDNA, i.e., the IHC cDNA. After subtraction hybridization, the new hybrids carry different adapters (adapter 1 & 2), allowing them to be preferentially amplified. The hybrids with OHC-specific expressed genes underwent two rounds of selective PCR amplification. The PCR amplification, hybridization and control reaction were according to manufacturer's instructions (Clontech). As shown in FIG. 14, the distribution pattern of OHC cDNA subtracted with IHC is quite different from that of the unsubtracted OHC cDNA pool.
Construction of OHC Subtracted cDNA Plasmid Library The final subtracted OHC cDNA pool was restriction digested with NotI and EagI and cloned into pGEM5Z(-), previously cut with NotI. The plasmid was then transformed into E. coli, produced an OHC subtracted cDNA plasmid library. 1320 Colonies were selected. A sample of these clones was used for T7/Sp6 PCR reaction to confirm the presence and the size of the inserts, as shown in FIG. 15. The PCR amplified cDNA was vacuum-filtered onto four identical nylon membranes (BioRad, Richmond, Va.) for hybridization. Forward-subtracted (OHC—IHC) and reverse-subtracted (IHC—OHC) cDNA, as well as tester (unsubtracted OHC) and driver (unsubtracted IHC) cDNA were radioactively labeled with $^{32}$P-dCTP using a random primer labeling method. The cDNA was hybridized with $5 \times 10^6$ counts per minute per milliliter of each individual probe overnight. After a final washing with 0.2×SSC/0.05% SDS, nylon membranes were exposed to autoradiographic film for 8 hours. Results are shown in FIG. 16. Positively hybridizing clones were scored for differential hybridization with forward (OHC—IHC; FIG. 16A) and reverse (IHC—OHC; FIG. 16B) subtracted probes. This differential hybridization was confirmed in most cases by confirming hybridization with tester (OHC; FIG. 16C) and driver (IHC; FIG. 16D) cDNA. In some cases, strongly differential hybridizing clones seen in the forward and reverse pair of blots were also selected for DNA sequencing despite a lack of signal from the tester and driver hybridization blots. 103 Clones were analyzed and selected from the OHC subtracted plasmid library. Of those, 18 clones were known genes, while 32 clones were unknown. Eleven of the unknown clones had evident open reading frames and 21 clones had no apparent coding sequence. Results for known genes are shown in Table 1.

TABLE 1

| KNOWN GENES | NUMBER OF CLONES |
| --- | --- |
| Collagen alpha-2 (I) | 8 |
| Mitochondria cytochrome c oxidase II | 3 |
| Acidic Protein Rich in Leucine (APRIL) | 2 |
| Mitochondrial tRNA | 2 |
| Oncomodulin | 2 |
| Adenine nucleotide translocase-2 (Ant2) | 1 |
| Acid sphiagomylenase (ASM)-like phosphodiesterase 3a | 1 |
| ATP synthase | 1 |
| Collagen alpha-1 (I) | 1 |
| Glycerol 3 phosphate acyltransferase | 1 |
| Inward rectifier K-channel | 1 |
| Mitochondrial DNA control region | 1 |
| Mitochondrial 12S RNA | 1 |
| Osteonectin (SPARC: secreted protein acidic rich in cysteine) | 1 |
| Prolylcarboxypeptidase | 1 |
| Receptor tyrosine kinase | 1 |
| Ribonucleotide reductase | 1 |
| Serine kinase (SRPK2) | 1 |

Figure 18:
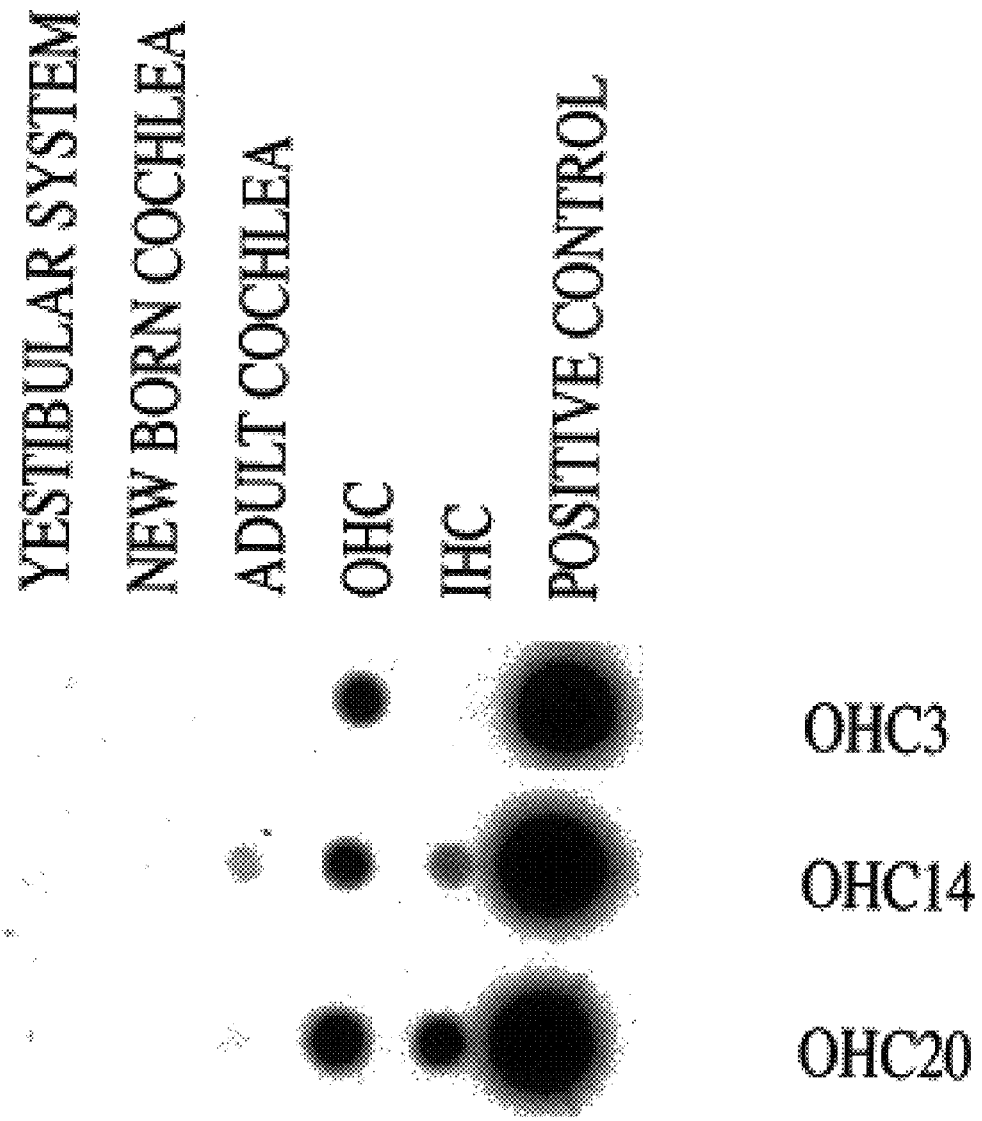
FIG. 18 is an image of a virtual Northern dot blot which confirms the differential expression of OHC—subtracted cDNAs.

Virtual Northern Dot Blot Experiments mRNAs were isolated using oligo-dT magnetic beads (Dynal) from thyroid, adult cochlea, newborn cochlea, IHC, OHC, and cultured organ of Corti treated with and without T3. cDNA pools from these tissues were created using the 5'-Cap PCR strategy as described above (Clontech). 0.5 Micrograms of each sample cDNA was mixed with 0.4 molar NaOH and 10 millimolar EDTA and then boiled at 100 degrees Celsius for 10 minutes. The cDNA samples were then vacuum filtered onto nylon membranes (BioRad). The membranes were neutralized with 0.5 molar Tris-HCl before hybridization. Unknown-gene fragments were radioactively labeled with $^{32}$P-dATP according to Random-Primed stripAble DNA probe Synthesis & Removal Kit™ (Ambion). Results for three genes are shown in FIG. 18.

Gamma-gt11 Gerbil Cochlea Library Screening

The library screening was performed using standard experimental procedure as described in, for example, Sambrook, et al., 1989 (*Molecular Cloning: A Laboratory Manual*, $2^{nd}$ Ed., Cold Spring Harbor Laboratory Press, N.Y.).

Example 3: Prestin is a Cytoplasmic Protein

N-tagged and C-tagged prestin constructs were created in the same general manner as above and subsequently transiently transfected into TSA201 cells. Immunofluorescence with FITC-labeled secondary antibodies against prestin was used to determine where in the cells the prestin protein is expressed. It has been concluded that prestin is expressed in the cytoplasm of the TSA201 cells.

Generation of C-tagged and N-tagged Prestin Constructs

The C-terminal end of prestin was amplified using an oligonucleotide (5'-GCCCTGAATTCCTCGGGTGTGG-3'; SEQ ID NO:13) which was complementary to the C-terminus of prestin, together with an upstream oligonucleotide primer (5'-GGACTACGGACTGATTACTGC-3'; SEQ ID NO:14). The first primer was modified to create an EcoRI restriction site for ligation into an expression vector. PCR was performed with these primers, resulting in an amplified C-terminal fragment of prestin. The PCR product was cloned into the expression vector pcDNA6/V5-HisA (Invitrogen, Carlsbad, Calif.) to create a full-length C-terminus tagged with a V5 epitope located downstream and in-frame with prestin. C-tagged pendrin was also generated by this method.

The N-terminal end of prestin was amplified using an oligonucleotide complementary to the N-terminus of prestin (5'-CTGCAGAATTCGGATCATGCCG-3'; SEQ ID NO:15) and a second downstream oligonucleotide primer (5'-CAACGATGGCTATGGCAATGGC-3'; SEQ ID NO:16) in a PCR reaction. As above, the first primer was modified to create an EcoRi restriction site for ligation into an expression vector. The amplified PCR product was cloned into the expression vector pcDNA3.1/HisB (Invitrogen) to produce a full-length N-tagged prestin protein with an Xpress epitope located upstream and in-frame with prestin.

Generation of Prestin-specific Antibodies

A peptide consisting of the first twenty N-terminal amino acids (MDHAEENEIPVATQKYHVER; SEQ ID NO:12) was synthesized commercially and used to immunize two rabbits (SynPep Corporation, Dublin, Calif.). Twenty milliliters of serum from the first bleed was affinity purified by SynPep using standard affinity purification techniques.

Immunofluorescence

TSA201 cells transfected with the various prestin constructs were fixed 1 percent paraformaldehyde in PBS for 10 minutes at room temperature, followed by two washes with PBS. Permeabilized cells were incubated for I hour at room temperature with 500 nanograms per milliliter anti-prestin in PBS containing 0.1 percent saponin and 2 milligrams per milliliter bovine serum albumin (BSA). The cells were washed and incubated with Cy3- or FITC-conjugated anti-rabbit (or anti-mouse) IgG secondary antibody (Sigma, St. Louis, Mo.) in blocking solution (PBS containing 10 percent goat serum and 2 milligrams per milliliter BSA) containing 0.1 percent saponin. The saponin was used to permeabilize the cell membrane, allowing antibody to bind to intracellular epitopes. The cells were incubated at room temperature for 30 minutes, followed by a 15 minute incubation with 1 microgram per milliliter propridium iodide (PI, Molecular Probes, ), a membrane-impermeant DNA-binding compound used to test plasma membrane integrity. The cells were washed with PBS and mounted using Fluoromount-G™ (Southern Biotechnology Associates, Birmingham, Ala.). Nonpermeabilized cells were similarly treated with the exception of adding saponin to the incubation solution. All cells were then immediately observed using a Nikon Eclipse E400 Microscope.

In vivo fluorescence experiments were also conducted. Adult Mongolian gerbils were euthanized and decapitated. Cochleae were dissected out and incubated with 4 percent paraformaldehyde in PBS for 1 hour at room temperature (1999, Mammano et al., J. Neurosci., 19(16):6918–6929). The cochleae were then washed 4 times with PBS, followed by a 1–2 hour incubation at room temperature with blocking solution (PBS containing 5 percent goat serum and 2 percent BSA). Blocking solution for perneabilized samples also contained 0.1 percent saponin. Samples were washed again 4 times with PBS and then the tectorial membrane was dissected out. The remaining cochlear sample was divided into three segments by cutting the modiolus. The segments were immunolabeled with antibody and stained with PI as described above. Samples were observed using a laser confocal microscope.

Immunofluorescence of Native Prestin

Specificity of anti-prestin antibody was tested using TSA201 cells transiently transfected with the C-tag (V5 epitope) prestin construct. The cells were incubated with both anti-prestin and anti-V5 antibodies as discussed above, followed by extensive washing. The cells were then incubated simultaneously with FITC-labeled anti-rabbit IgG and Cy3-labeled anti-mouse IgG. The anti-prestin antibody attached to the FITC-labeled anti-rabbit IgG, fluoresced as green and the anti-V5 antibody, conjugated with Cy3-anit-mouse IgG, stained red.

Nonlinear Capacitance Measurements

The method for measuring nonlinear capacitance is discussed above. Nonlinear capacitance in TSA201 cells was measured in order to determine whether the attached V5 or Xpress epitope tags interfered with the normal function of prestin (i.e., voltage-dependent charge movement).

The results of the experiments are now described.

Nonlinear capacitance measurements demonstrated that when TSA201 cells are transfected with N-tagged prestin/GFP or C-tagged prestin/GFP, a typical nonlinear capacitance curve is observed (FIG. 20). This suggests that the V5 and Xpress epitope tags do not interfere with the voltage-dependent charge movement function of prestin.

Figure 21A:
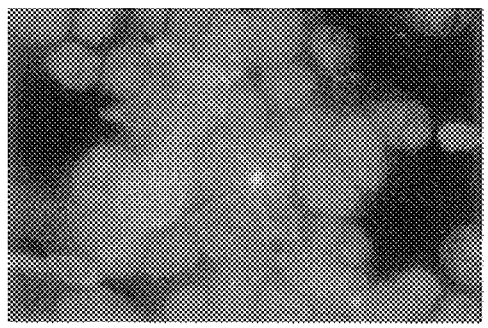
FIGS. 21A–21D, depicts inmmunofluorescence images of TSA201 cells transiently transfected with C-tagged prestin (V5 epitope.
Figure 21B:
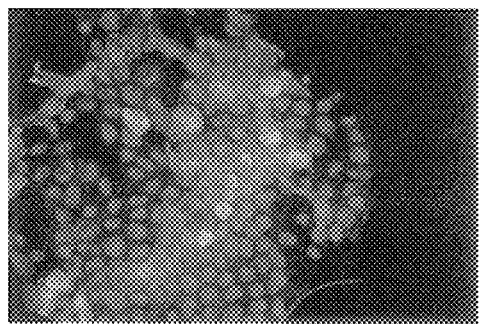
Figure 21C:
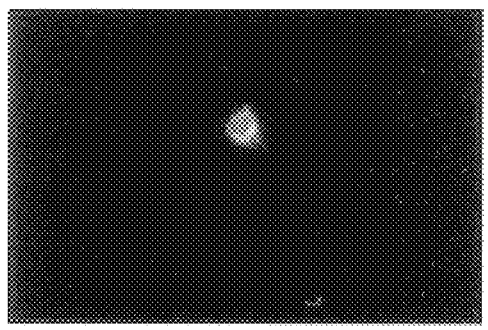
Figure 21D:
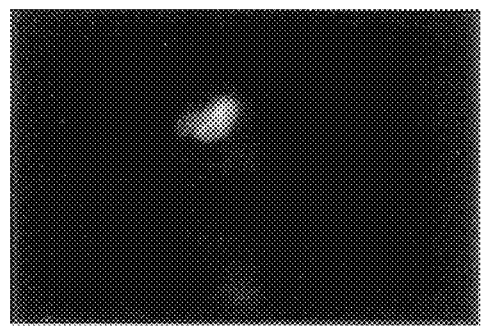

Indirect immunofluorescence with FITC-labeled secondary antibody revealed that the anti-Xpress antibody (FIG. 21A) and the anti-V5 antibody (FIG. 21B) expressed green fluorescence in the plasma membrane of about one-third of the cells. This roughly reflects calcium phosphate transfection efficiency (about 30 percent) for TSA201 cells. Propidium Iodide staining was observed in nuclei of all cells. Cells transfected with control vectors did not express green fluorescence.

Figure 22A:
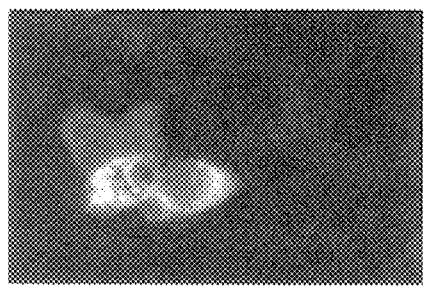
FIGS. 22A–22D, is a set of images depicting immunofluorescence of transiently transfected TSA201 cells.
Figure 22B:
Figure 22C:
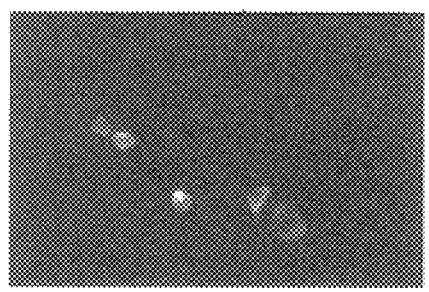
Figure 22D:
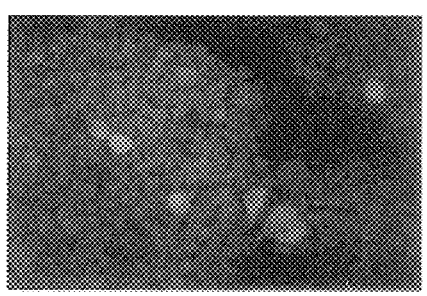
Figure 23A:
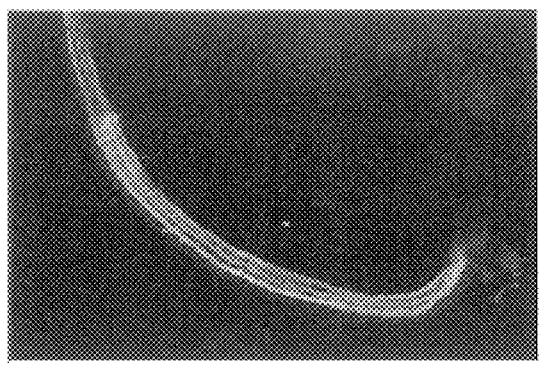
FIGS. 23A–23D, is a set of immunofluorescent images of the basilar membrane/organ of Corti complex.
Figure 23B:
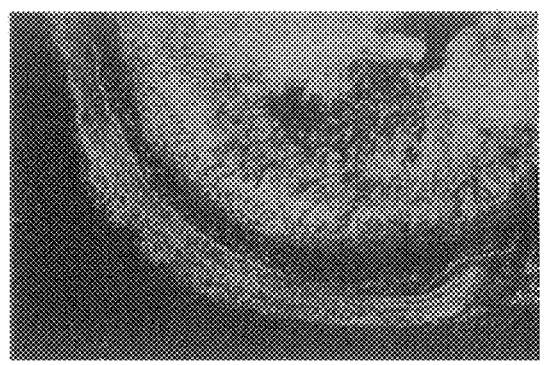
Figure 23C:
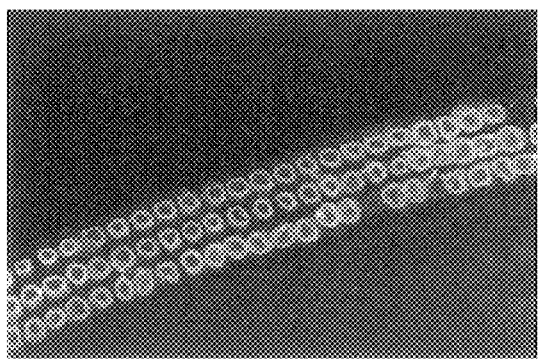
Figure 23D:
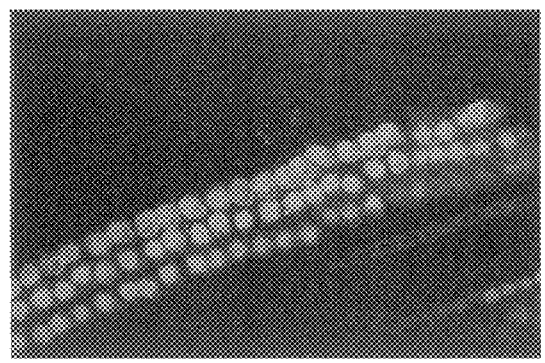

Because very few nonpermeabilized cells expressed green fluorescence and propidium iodide staining, it is proposed that these cells lacked plasma membrane integrity (FIGS. 22C and 22D). All of these data suggest that the N and C. termnini of prestin are located in the cytoplasm of TSA201 cells expressing the synthetic epitope tagged versions of prestin.

Figure 24A:
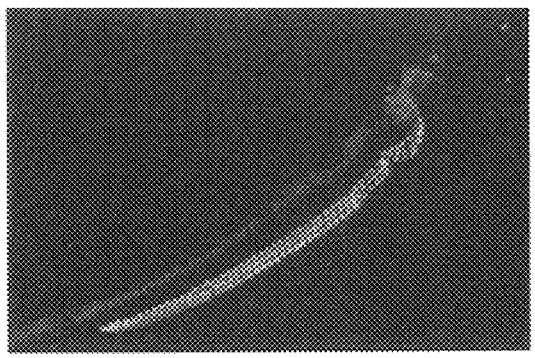
FIGS. 24A–24D, is a set of immunofluorescent images of permeabilized (FIGS. 24A and 24B) and nonpermeabilized (FIGS. 24C and 24D) cells binding with FITC-labeled rabbit IgG.
Figure 24B:
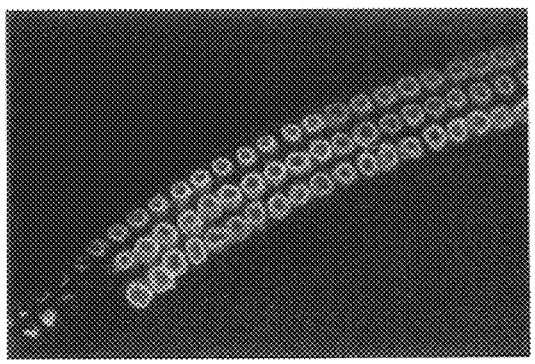
Figure 24C:
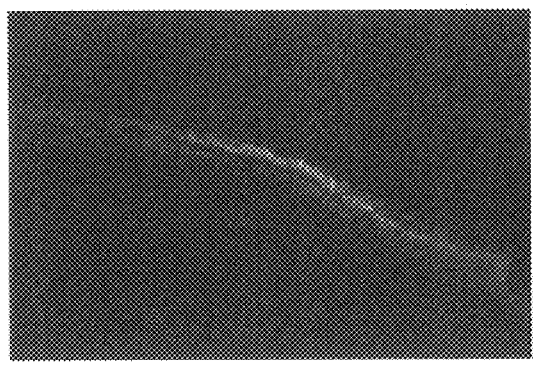
Figure 24D:
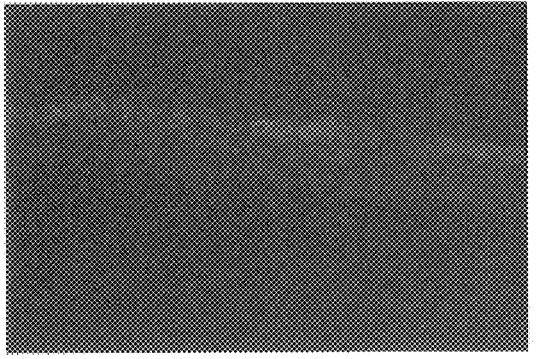
Figure 25:
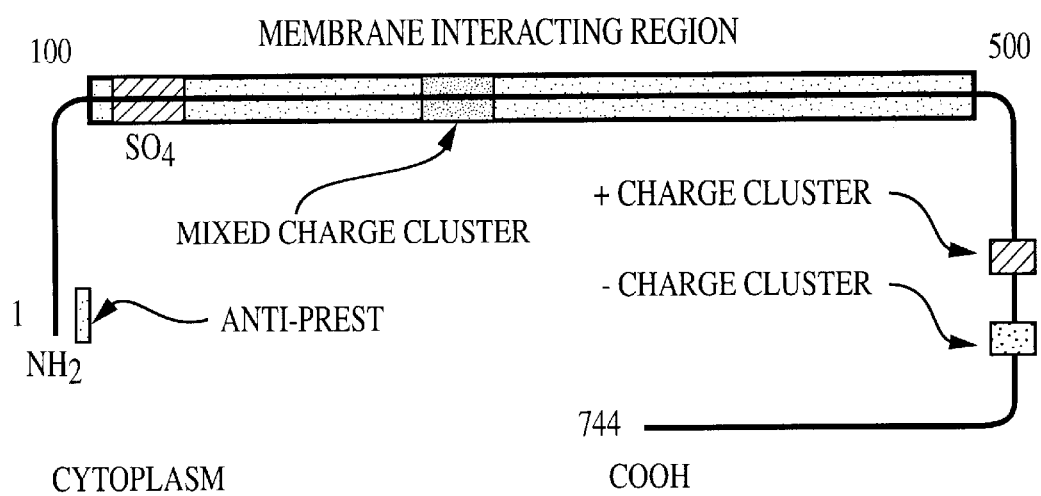
FIG. 25 represents a predicted topology of the prestin protein. Charge clusters and sulfate transporter motif are indicated by boxes.

Immunofluorescence studies of native prestin were also performed. FIG. 22 depicts green fluorescence of cells, indicating the presence of the native prestin epitope in the cells. These cells also stained red, confirming the presence of the V5 epitope. The Xpress epitope apparently does not interfere with the immunofluorescent reaction of anti-prestin and its eptiope. These data suggest that the anti-prestin antibody specifically binds with prestin. FIGS. 24A and 24B demonstrate that prestin expression was observed in OHCs, but not in IHCs or other basilar membrane and organ of Corti cells. Prestin is localized in the basolateral wall of OHC as shown in FIGS. 24C and 24D.

Immunofluorescence results for permeabilized versus nonpermeabilized organ of Corti samples are shown in FIG. 24. Permeabilized samples are shown in FIGS. 24A and 24B and nonpermeabilized samples are shown in FIGS. 24C and 24D. Some nonpermeabilized cells, as in FIG. 24C, exhibited weak fluorescent staining. These cells may have damaged plasma membranes. The results shown in FIG. 24 further confirm that the N-terminus of native prestin is located in the cytoplasm.

The results ultimately suggest that both the C- and N-termini are located within the cytoplasm of cells. Both termini are possible sites of interaction with OHC cytoplasm proteins. The results also suggest that the positive and negative cluster regions near the C-terminus may play a unique role in protein function.

The disclosure of every patent, patent application, and publication cited herein is hereby incorporated herein by reference in its entirety. While this invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed is:

1. An isolated polynucleotide consisting of 22 to 400 consecutive nucleotides of the murine prestin cDNA sequence set forth in SEQ ID NO:4, wherein said polynucleotide hybridizes with high stringency with the coding region of a mammalian prestin nucleic acid under the following hybridization conditions at about 50 degrees Celsius:
   a. 0.015 M NaCl;
   b. 1.5 mM sodium citrate; and
   c. 0.1% (w/v) sodium dodecyl sulfate.

2. The isolated polynucleotide of claim 1, wherein the mammalian pres nucleic acid comprises the nucleotide sequence listed in SEQ ID NO:4.

3. An isolated polynucleotide comprising the coding region of a mammalian prestin nucleic acid, wherein the coding region is at least 87% homologous with SEQ ID NO:4, and further wherein said isolated polynucleotide encodes a polypeptide that modulates the shape of mammalian cochlear outer hair cells in response to the membrane potential of the plasma membrane of the cells.

4. The isolated polynucleotide of claim 3, further comprising a promoter/regulatory region operably linked with the coding region.

5. An isolated polynucleotide comprising the sequence listed in SEQ ID NO:4.

6. An isolated polynucleotide consisting of 22 to 400 consecutive nucleotides of the murine prestin cDNA sequence set forth in SEQ ID NO:4, wherein said polynucleotide hybridizes with high stringency with the coding region of a mammalian prestin nucleic acid under the following hybridization conditions at about 42 degrees Celsius:
   a. 50% (v/v) formamide;
   b. 0.1% (w/v) bovine serum albumin;
   c. 0.1% (w/v) Ficoll;
   d. 0.1% (w/v) polyvinylpyrrolidone;
   e. 50 mM sodium phosphate buffer at pH 6.5;
   f. 750 mM NaCl; and
   g. 75 mM sodium citrate.

* * * * *

SEQUENCE LISTING

<160> NUMBER OF SEQ ID NOS: 16

<210> SEQ ID NO 1
<211> LENGTH: 744
<212> TYPE: PRT
<213> ORGANISM: Meriones unguiculatus

<400> SEQUENCE: 1

```
Met Asp His Ala Glu Glu Asn Glu Ile Pro Val Ala Thr Gln Lys Tyr
1               5                   10                  15

His Val Glu Arg Pro Ile Phe Ser His Pro Val Leu Gln Glu Arg Leu
            20                  25                  30

His Val Lys Asp Lys Val Ser Glu Ser Ile Gly Asp Lys Leu Lys Gln
        35                  40                  45

Ala Phe Thr Cys Thr Pro Lys Lys Ile Arg Asn Ile Ile Tyr Met Phe
    50                  55                  60

Leu Pro Ile Thr Lys Trp Leu Pro Ala Tyr Lys Phe Lys Glu Tyr Val
65                  70                  75                  80

Leu Gly Asp Leu Val Ser Gly Ile Ser Thr Gly Val Leu Gln Leu Pro
                85                  90                  95

Gln Gly Leu Ala Phe Ala Met Leu Ala Ala Val Pro Pro Val Phe Gly
            100                 105                 110

Leu Tyr Ser Ser Phe Tyr Pro Val Ile Met Tyr Cys Phe Phe Gly Thr
        115                 120                 125

Ser Arg His Ile Ser Ile Gly Pro Phe Ala Val Ile Ser Leu Met Ile
    130                 135                 140

Gly Gly Val Ala Val Arg Leu Val Pro Asp Asp Ile Val Ile Pro Gly
145                 150                 155                 160

Gly Val Asn Ala Thr Asn Gly Thr Glu Ala Arg Asp Ala Leu Arg Val
                165                 170                 175

Lys Val Ala Met Ser Val Thr Leu Leu Ser Gly Ile Ile Gln Phe Cys
            180                 185                 190

Leu Gly Val Cys Arg Phe Gly Phe Val Ala Ile Tyr Leu Thr Glu Pro
        195                 200                 205

Leu Val Arg Gly Phe Thr Thr Ala Ala Ala Val His Val Phe Thr Ser
```

-continued

```
                    210                 215                 220
Met Leu Lys Tyr Leu Phe Gly Val Lys Thr Lys Arg Tyr Ser Gly Ile
225                 230                 235                 240
Phe Ser Val Val Tyr Ser Thr Val Ala Val Leu Gln Asn Val Lys Asn
                    245                 250                 255
Leu Asn Val Cys Ser Leu Gly Val Gly Leu Met Val Phe Gly Leu Leu
                260                 265                 270
Leu Gly Gly Lys Glu Phe Asn Glu Arg Phe Lys Glu Lys Leu Pro Ala
            275                 280                 285
Pro Ile Pro Leu Glu Phe Phe Ala Val Val Met Gly Thr Gly Ile Ser
        290                 295                 300
Ala Gly Phe Asn Leu His Glu Ser Tyr Ser Val Asp Val Val Gly Thr
305                 310                 315                 320
Leu Pro Leu Gly Leu Leu Pro Ala Asn Pro Asp Thr Ser Leu Phe
                    325                 330                 335
His Leu Val Tyr Val Asp Ala Ile Ala Ile Ala Ile Val Gly Phe Ser
                340                 345                 350
Val Thr Ile Ser Met Ala Lys Thr Leu Ala Asn Lys His Gly Tyr Gln
            355                 360                 365
Val Asp Gly Asn Gln Glu Leu Ile Ala Leu Gly Ile Cys Asn Ser Ile
        370                 375                 380
Gly Ser Leu Phe Gln Thr Phe Ser Ile Ser Cys Ser Leu Ser Arg Ser
385                 390                 395                 400
Leu Val Gln Glu Gly Thr Gly Gly Lys Thr Gln Leu Ala Gly Cys Leu
                    405                 410                 415
Ala Ser Leu Met Ile Leu Leu Val Ile Leu Ala Thr Gly Phe Leu Phe
                420                 425                 430
Glu Ser Leu Pro Gln Ala Val Leu Ser Ala Ile Val Ile Val Asn Leu
            435                 440                 445
Lys Gly Met Phe Met Gln Phe Ser Asp Leu Pro Phe Phe Trp Arg Thr
        450                 455                 460
Ser Lys Ile Glu Leu Thr Ile Trp Leu Thr Thr Phe Val Ser Ser Leu
465                 470                 475                 480
Phe Leu Gly Leu Asp Tyr Gly Leu Ile Thr Ala Val Ile Ile Ala Leu
                    485                 490                 495
Leu Thr Val Ile Tyr Arg Thr Gln Ser Pro Ser Tyr Lys Val Leu Gly
                500                 505                 510
Gln Leu Pro Asp Thr Asp Val Tyr Ile Asp Ile Asp Ala Tyr Glu Glu
            515                 520                 525
Val Lys Glu Ile Pro Gly Ile Lys Ile Phe Gln Ile Asn Ala Pro Ile
        530                 535                 540
Tyr Tyr Ala Asn Ser Asp Leu Tyr Ser Asn Ala Leu Lys Arg Lys Thr
545                 550                 555                 560
Gly Val Asn Pro Ala Leu Ile Met Gly Ala Arg Arg Lys Ala Met Arg
                    565                 570                 575
Lys Tyr Ala Lys Glu Val Gly Asn Asn Ile Ala Asn Ala Ala Val
                580                 585                 590
Val Lys Val Asp Gly Glu Val Asp Gly Glu Asn Ala Thr Lys Pro Glu
            595                 600                 605
Glu Glu Asp Asp Glu Val Lys Tyr Pro Pro Ile Val Ile Lys Thr Thr
        610                 615                 620
Phe Pro Glu Glu Leu Gln Arg Phe Met Pro Gln Thr Glu Asn Val His
625                 630                 635                 640
```

```
Thr Ile Ile Leu Asp Phe Thr Gln Val Asn Phe Ile Asp Ser Val Gly
                645                 650                 655

Val Lys Thr Leu Ala Val Met Val Lys Glu Tyr Gly Asp Val Gly Ile
            660                 665                 670

Tyr Val Tyr Leu Ala Gly Cys Ser Pro Gln Val Val Asn Asp Leu Thr
            675                 680                 685

Arg Asn Arg Phe Phe Glu Asn Pro Ala Leu Lys Glu Leu Leu Phe His
            690                 695                 700

Ser Ile His Asp Ala Val Leu Gly Ser His Val Arg Glu Ala Met Ala
705                 710                 715                 720

Glu Gln Glu Ala Ser Ala Pro Pro Gln Asp Asp Met Glu Pro Asn
                725                 730                 735

Ala Thr Pro Thr Thr Pro Glu Ala
            740

<210> SEQ ID NO 2
<211> LENGTH: 4113
<212> TYPE: DNA
<213> ORGANISM: Meriones unguiculatus

<400> SEQUENCE: 2
gcggccgcgt cgacggcagc ggcggctccg ccctgcgcag ccccggcagc gctggctggt      60
ggcgggggag ggcgaacagt ccctttttcca gccctcagca gttgactgcc ctgtacctgg    120
agttcccagc cggcttttcca tcccctgtac cttgtgctat acgttggatc tggtgcctgt    180
ccagaaatgc tcgtctcctg ctgttggtga ataactgcag accatggatc atgccgaaga    240
aaatgaaatc cctgtggcaa cccagaagta ccacgtggaa aggcctatct tcagtcatcc    300
cgtcctccag gagaggctgc atgtcaagga caaagtctca gagtccattg gggataagct    360
gaagcaggcg ttcacatgca ctcccaaaaa gataagaaac atcatttaca tgttcctgcc    420
catcactaag tggttgccag cttacaagtt caaggagtat gtgttgggtg acttggtttc    480
aggcataagc accggcgtgc ttcagcttcc ccaaggctta gccttcgcaa tgctcgcggc    540
tgttcctccg gtgttcggcc tgtactcttc attttatcct gttatcatgt actgtttctt    600
tgggacctcc agacacatat ctataggtcc tttcgccgtc attagtttga tgatcggtgg    660
tgtggctgtc cggctggtcc ccgatgacat cgtcatcccg ggaggagtga acgcaaccaa    720
cggcacggag gcccgagacg cgctgagagt gaaagtcgcc atgtctgtca ccctgctctc    780
aggaatcatt cagttttgcc taggtgtgtg caggtttgga tttgtggcca tatacctcac    840
ggagccgctg gtgcgagggt tcaccaccgc cgccgccgtg cacgtcttca catccatgtt    900
gaaatacctg tttggggtta agacaaagcg gtacagtggg atcttttcgg tggtatatag    960
tacagttgct gtgttgcaga atgttaaaaa cctcaacgtg tgttccctag cgtcggcct    1020 gatggttttt ggtttgctgt tgggtggcaa ggagtttaat gagagattta agagaaatt    1080 gccagcaccc attcctctag agttctttgc tgtggtgatg ggaactggca tttccgcggg    1140
gtttaacttg cacgagtcct acagtgtgga tgtcgttgga actcttcctc tggggctact    1200
ccctcctgcc aacccggaca ccagcctctt ccacctcgtg tatgtggatg ccattgccat    1260
agccatcgtt ggatttttcag tgacaatttc catggccaaa accttggcga ataagcatgg    1320
ctaccaggtt gatggcaatc aggagctcat cgctttgggg atatgcaact ccatcggatc    1380
tctcttccag accttctcca tttcctgctc cttgtctcgc agccttgttc aggagggaac    1440
tggagggaaa acacagctcg caggttgctt ggcctcgctg atgattctgc tggtcatttt    1500
```

```
agccactgga ttcctctttg agtcattgcc ccaggctgtg ctctcggcca ttgtgatcgt    1560
gaacctgaaa gggatgttta tgcagttctc agatctgccc ttcttctgga gaaccagcaa    1620
aatagagctg accatctggc ttaccacctt tgtgtcctcc ctgttcctgg gcttggacta    1680
cggactgatt actgctgtga tcattgctct gctgactgtg atttacagaa cccagagtcc    1740
gagctacaag gtcctggggc agctccctga caccgatgta tacattgaca tagacgcata    1800
tgaggaggtg aaagaaattc ctggaataaa aatattccag ataaacgccc caatttacta    1860
tgcaaacagt gacttgtata gcaacgccct aaaaagaaag actggtgtga acccagcgct    1920
cataatggga gcaagaagga aggccatgag gaagtacgca aaggaagtcg gaaacgccaa    1980
cattgccaac gcagctgttg tcaaagtgga tggagaagta gatggagaaa atgctacgaa    2040
gcccgaagaa gaggatgatg aagtaaaata tccccccaata gtcatcaaaa caacatttcc    2100
tgaagagctg cagagattta tgccccagac agaaaatgtc cacactatca ttctagactt    2160
cacacaagtc aattttatcg actctgttgg agtaaaaacc ctggctgtga tggtgaagga    2220
atacggagat gttggtattt atgtgtactt agcaggatgc agcccacaag tcgtgaatga    2280
cctcacccgc aaccgtttct ttgaaaatcc tgccttaaaa gagcttctgt ccacagtat     2340 ccatgatgca gtcttgggca gccatgttcg agaggcaatg gctgagcaag aagcctcagc    2400
cccacctccc caggacgaca tggagcccaa tgccacaccc accacacccg aggcataaag    2460
ggcctgcctg ggcctgtgca cctcttgaat tctgaactta catgctttaa ataccaggcc    2520
ttaggttttc ttctacccaa cccccaaccc ccaaggaaaa tgttagtagt tatggcttga    2580
tttggagggt gaatgatgtg tagtgcgatg tatctcagac ttgtgttatt ttatctgaat    2640
aattcaaaga ttaagtggcc tttcgcactt atgtagtgat gtttgtatta tatcttaaag    2700
tcaaaaaaaa aaaaaaaaaa aaaagtcga cgcggccgcg gtcgacgcgg gcgcgaattc    2760
gcggccgcgt cgactttttt ttttttttt ttttttttc ttgtcaacat tttaatgcaa    2820
acaatatagt gtttttgact ctaggcatct gtaacgaaac agtgctagaa tgggataagc    2880
atctgcagct tctgtggagt gaatgcaatt agaactactc tgcccctgac tgcagaagcc    2940
aggcattgtg cccacacct gccaacctcc actgaggagg ctacggcagg acgatcacag     3000
tgagttccag gccagcctgg gctacagagg gaggctcaaa ccccaaaact aaacaaatta    3060
aaaacaaaac aaaaaccaag gggaaattct tgtcaagctc cttttgaaagc tgatgtttca   3120 aagcacagga tttgtcttct ctagtagaga tatatttcct aagggagtgg aaggagtaag    3180
gttcaggctt acctgtctgt gaaacaccac aagcagtctc atccagacca ctgcttcccc    3240 tgactcccctt tgcacatgga ggacaaacac ttggagagga acttaggtga cctgcttgct   3300
gcaaaaatca actatcaaga aagatttgga gaaacgctag tctgagaaac gagattacaa    3360
gagcctgtgg atttcttccc tgcaacactg gggccaacct ttcatgtctg atcagaaata    3420
acgggcatag tgtttattgt aagcctgaac catgaagaca gagcactgag ataggaagcc    3480
catttgacag tggcaatttc aaattaacag cttagttatg atggaacaca aactgcaaag    3540
gccttcattt cctgtgtttg atgaagtca cgatccaaca gtgggttaag agtgtggaag     3600
gtagaaggca gcagctgaac tgttgtgagt ggtccaagga ggcagagatg cttcaagcac    3660
tcctcgccac cctcagcttc tcttcaagga gccaagagga tgaggagctg gtgcacccag    3720
agggtctaac cggggcttgc agagtcctaa agacatctct ctgcaggcag aaattgcaca    3780
gcttaattct tctagactga acagcttcag atttatgcca gtggaaagca aacattgttt    3840
```

-continued

```
ctaagtcatt taattgtgtt actgtctctc aactttatca gatgttgctt gggtagagag    3900
gcctgtgtgc agttctgagg gcggctttat ggtgctccct ggctccttct aaatgcccac    3960
agcccagagt ccctaatgga gcactttcca gatgtaaaaa ctactaattc aaaaggttca    4020
aatggcattt gtctcaatcc aggacgcaca ctgaaggctg catcttcacc aaatcgacaa    4080
ccttgatcgc aggtgctagg tcgacgcggc cgc                                 4113
```

<210> SEQ ID NO 3
<211> LENGTH: 744
<212> TYPE: PRT
<213> ORGANISM: Mus sp.

<400> SEQUENCE: 3

```
Met Asp His Ala Glu Glu Asn Glu Ile Pro Ala Glu Thr Gln Arg Tyr
1               5                   10                  15

Tyr Val Glu Arg Pro Ile Phe Ser His Pro Val Leu Gln Glu Arg Leu
            20                  25                  30

His Val Lys Asp Lys Val Thr Glu Ser Ile Gly Asp Lys Leu Lys Gln
        35                  40                  45

Ala Phe Thr Cys Thr Pro Lys Lys Ile Arg Asn Ile Ile Tyr Met Phe
    50                  55                  60

Leu Pro Ile Thr Lys Trp Leu Pro Ala Tyr Lys Phe Lys Glu Tyr Val
65                  70                  75                  80

Leu Gly Asp Leu Val Ser Gly Ile Ser Thr Gly Val Leu Gln Leu Pro
                85                  90                  95

Gln Gly Leu Ala Phe Ala Met Leu Ala Ala Val Pro Pro Val Phe Gly
            100                 105                 110

Leu Tyr Ser Ser Phe Tyr Pro Val Ile Met Tyr Cys Phe Phe Gly Thr
        115                 120                 125

Ser Arg His Ile Ser Ile Gly Pro Phe Ala Val Ile Ser Leu Met Ile
    130                 135                 140

Gly Gly Val Ala Val Arg Leu Val Pro Asp Asp Ile Val Ile Pro Gly
145                 150                 155                 160

Gly Val Asn Ala Thr Asn Gly Thr Glu Ala Arg Asp Ala Leu Arg Val
                165                 170                 175

Lys Val Ala Met Ser Val Thr Leu Leu Ser Gly Ile Ile Gln Phe Cys
            180                 185                 190

Leu Gly Val Cys Arg Phe Gly Phe Val Ala Ile Tyr Leu Thr Glu Pro
        195                 200                 205

Leu Val Arg Gly Phe Thr Thr Ala Ala Ala Val His Val Phe Thr Ser
    210                 215                 220

Met Leu Lys Tyr Leu Phe Gly Val Lys Thr Lys Arg Tyr Ser Gly Ile
225                 230                 235                 240

Phe Ser Val Val Tyr Ser Thr Val Ala Val Leu Gln Asn Val Lys Asn
                245                 250                 255

Leu Asn Val Cys Ser Leu Gly Val Gly Leu Met Val Phe Gly Leu Leu
            260                 265                 270

Leu Gly Gly Lys Glu Phe Asn Glu Arg Phe Lys Glu Lys Leu Pro Ala
        275                 280                 285

Pro Ile Pro Leu Glu Phe Phe Ala Val Val Met Gly Thr Gly Ile Ser
    290                 295                 300

Ala Gly Phe Asn Leu His Glu Ser Tyr Ser Val Asp Val Val Gly Thr
305                 310                 315                 320

Leu Pro Leu Gly Leu Leu Pro Pro Ala Asn Pro Asp Thr Ser Leu Phe
```

-continued

```
                325                 330                 335
His Leu Val Tyr Val Asp Ala Ile Ala Ile Ala Ile Val Gly Phe Ser
                340                 345                 350
Val Thr Ile Ser Met Ala Lys Thr Leu Ala Asn Lys His Gly Tyr Gln
                355                 360                 365
Val Asp Gly Asn Gln Glu Leu Ile Ala Leu Gly Ile Cys Asn Ser Ile
                370                 375                 380
Gly Ser Leu Phe Gln Thr Phe Ser Ile Ser Cys Ser Leu Ser Arg Ser
385                 390                 395                 400
Leu Val Gln Glu Gly Thr Gly Lys Thr Gln Leu Ala Gly Cys Leu
                405                 410                 415
Ala Ser Leu Met Ile Leu Leu Val Ile Leu Ala Thr Gly Phe Leu Phe
                420                 425                 430
Glu Ser Leu Pro Gln Ala Val Leu Ser Ala Ile Val Ile Val Asn Leu
                435                 440                 445
Lys Gly Met Phe Met Gln Phe Ser Asp Leu Pro Phe Phe Trp Arg Thr
                450                 455                 460
Ser Lys Ile Glu Leu Thr Ile Trp Leu Thr Thr Phe Val Ser Ser Leu
465                 470                 475                 480
Phe Leu Gly Leu Asp Tyr Gly Leu Ile Thr Ala Val Ile Ile Ala Leu
                485                 490                 495
Leu Thr Val Ile Tyr Arg Thr Gln Ser Pro Ser Tyr Lys Val Leu Gly
                500                 505                 510
Gln Leu Pro Asp Thr Asp Val Tyr Ile Asp Ile Asp Ala Tyr Glu Glu
                515                 520                 525
Val Lys Glu Ile Pro Gly Ile Lys Ile Phe Gln Ile Asn Ala Pro Ile
                530                 535                 540
Tyr Tyr Ala Asn Ser Asp Leu Tyr Ser Ser Ala Leu Lys Arg Lys Thr
545                 550                 555                 560
Gly Val Asn Pro Ala Leu Ile Met Gly Ala Arg Arg Lys Ala Met Arg
                565                 570                 575
Lys Tyr Ala Lys Glu Val Gly Asn Ala Asn Val Ala Asn Ala Thr Val
                580                 585                 590
Val Lys Val Asp Ala Glu Val Asp Gly Glu Asn Ala Thr Lys Pro Glu
                595                 600                 605
Glu Glu Asp Asp Glu Val Lys Phe Pro Pro Ile Val Ile Lys Thr Thr
                610                 615                 620
Phe Pro Glu Glu Leu Gln Arg Phe Leu Pro Gln Gly Glu Asn Val His
625                 630                 635                 640
Thr Val Ile Leu Asp Phe Thr Gln Val Asn Phe Val Asp Ser Val Gly
                645                 650                 655
Val Lys Thr Leu Ala Gly Ile Val Lys Glu Tyr Gly Asp Val Gly Ile
                660                 665                 670
Tyr Val Tyr Leu Ala Gly Cys Ser Pro Gln Val Val Asn Asp Leu Thr
                675                 680                 685
Arg Asn Asn Phe Phe Glu Asn Pro Ala Leu Lys Glu Leu Leu Phe His
                690                 695                 700
Ser Ile His Asp Ala Val Leu Gly Ser Gln Val Arg Glu Ala Met Ala
705                 710                 715                 720
Glu Gln Glu Ala Thr Ala Ser Leu Pro Gln Glu Asp Met Glu Pro Asn
                725                 730                 735
Ala Thr Pro Thr Thr Pro Glu Ala
                740
```

<210> SEQ ID NO 4
<211> LENGTH: 2441
<212> TYPE: DNA
<213> ORGANISM: Mus sp.

<400> SEQUENCE: 4

| | | | | | |
|---|---|---|---|---|---|
| gcagtggcgg | ctccgcccag | cgcagccccg | ggcagcgctg | gtggccggga | agggctcatc | 60 |
| gtccctttc | cagccctcgg | cagtttactg | cggccctgta | cctggagctc | tggctgggtg | 120 |
| gtcatctcct | gccttgtgc | tgtacgttgg | atctagtggc | catccagaaa | tgcttgtctc | 180 |
| ctgctgttgg | tgaataactg | cagaccatgg | atcatgctga | agaaaatgaa | atccctgcag | 240 |
| agacccagag | gtactacgtg | gaaaggccca | tcttcagtca | tcctgtcctc | caagagaggc | 300 |
| tgcacgtcaa | ggacaaagtc | acagagtcca | ttggagataa | gctgaagcag | gcattcacgt | 360 |
| gtactcctaa | aaaataaga | aacatcattt | acatgttcct | gcctatcact | aagtggctgc | 420 |
| cagcatataa | attcaaggag | tatgtgttag | gtgacttggt | ctcgggcata | agcactgggg | 480 |
| tactccagct | tccccaaggc | ttagccttcg | ccatgctggc | agccgtgcct | ccggtgtttg | 540 |
| gcctgtactc | atcgttttac | cccgttatca | tgtactgttt | ctttggaacc | tcaagacaca | 600 |
| tatctatagg | tcctttgct | gttattagct | tgatgattgg | aggtgtggcc | gtccggttag | 660 |
| taccagatga | tattgtcatc | ccaggaggag | taaatgcaac | caacgggaca | gaagccagag | 720 |
| atgcactaag | agtgaaagtc | gccatgtctg | ttaccttact | ttcaggaatc | attcagtttt | 780 |
| gcctaggtgt | ctgtaggttt | ggatttgtgg | ccatatacct | cacggagcca | ttggtgcgag | 840 |
| gctttaccac | tgcggctgct | gtccacgtgt | tcacgtccat | gttaaaatac | ctgtttgggg | 900 |
| tcaaaacaaa | gcggtacagt | ggaatctttt | cagtggtgta | tagtacagtt | gctgtgttgc | 960 |
| agaatgttaa | aaacctcaac | gtgtgttccc | taggcgtcgg | cctgatggtt | tttggtttgc | 1020 |
| tgttgggtgg | caaggaattt | aatgagagat | ttaaagagaa | attgccagca | cccattcctc | 1080 |
| tagagttctt | tgctgtggtg | atggggactg | gcatttctgc | aggatttaac | ctacatgagt | 1140 |
| cctacagtgt | ggatgtcgtt | ggaacacttc | ctctggggct | acttcctccg | gccaacccag | 1200 |
| acaccagcct | gttccacctg | gtgtatgtgg | acgccattgc | catcgccatc | gttggatttt | 1260 |
| cagtgacgat | ctccatggcc | aaaaccttgg | caaataagca | tggctaccag | gttgatggca | 1320 |
| atcaggagct | cattgccttg | gggatatgca | actccattgg | atctctcttc | caaaccttct | 1380 |
| cgatttcctg | ctccttgtct | cgaagccttg | ttcaggaagg | aactggaggg | aaaacacagc | 1440 |
| ttgcaggttg | tttggcctcg | ttgatgattc | tgttggtcat | attagccacc | ggattcctct | 1500 |
| ttgagtcgtt | accccaggct | gtcctttccg | ccattgtgat | cgtcaacctg | aaaggaatgt | 1560 |
| tcatgcagtt | ctcagacctg | cctttttttt | ggagaaccag | caaaatagag | ctgaccatct | 1620 |
| ggctgaccac | ctttgtgtcc | tccctgttcc | tcggcttgga | ctacgactg | attaccgccg | 1680 |
| tgatcattgc | tctgctcaca | gtgatttata | gaacacagag | tccaagctac | aaagtcctgg | 1740 |
| ggcagctccc | tgacacggat | gtgtacattg | acatagatgc | atatgaggag | gtgaaagaaa | 1800 |
| ttcctggaat | aaaaatattc | caaataaatg | ccccaattta | ctatgcaaat | agcgacttgt | 1860 |
| atagcagcgc | tttaaaaaga | aagactggag | taaacccagc | actcattatg | ggagcgagaa | 1920 |
| gaaaggccat | gaggaagtac | gccaaggaag | ttggaaatgc | caacgtggcc | aatgctactg | 1980 |
| ttgtcaaagt | ggatgcagaa | gtagacggag | aaaatgctac | aaaacctgaa | gaagaggatg | 2040 |
| atgaagtcaa | atttccccca | atagtcatca | aaacaacatt | tcctgaagag | ctgcagagat | 2100 |

-continued

```
ttttgcccca gggggaaaat gtccacactg tcattctaga ctttacgcag gtcaattttg    2160
tggattctgt tggagtgaaa actctggccg ggattgtgaa agaatatgga gatgttggaa    2220
tttatgtata tttagcagga tgcagcccac aagttgtgaa tgacctcacc cgcaacaact    2280
tttttgaaaa tcctgccttg aaagagcttc tgttccacag tatccacgat gcagtcctgg    2340
gcagccaagt tcgggaggca atggctgaac aagaagccac agcgtcactt ccccaggagg    2400
atatggagcc caatgccaca cccaccaccc ccgaggcata a                        2441
```

<210> SEQ ID NO 5
<211> LENGTH: 295
<212> TYPE: PRT
<213> ORGANISM: Homo sapiens

<400> SEQUENCE: 5

```
Met Asp His Ala Glu Glu Asn Glu Ile Leu Ala Ala Thr Gln Lys Tyr
1               5                   10                  15

His Val Glu Arg Pro Ile Phe Ser His Pro Val Leu Gln Glu Arg Leu
            20                  25                  30

His Val Lys Asp Lys Val Ser Glu Ser Ile Gly Asp Lys Leu Lys Gln
        35                  40                  45

Ala Phe Thr Cys Thr Pro Lys Lys Ile Arg Asn Ile Ile Tyr Met Phe
    50                  55                  60

Leu Pro Ile Thr Lys Trp Leu Pro Ala Tyr Lys Phe Lys Glu Tyr Val
65                  70                  75                  80

Leu Gly Asp Leu Val Ser Gly Ile Ser Thr Gly Val Leu Gln Leu Pro
                85                  90                  95

Gln Gly Leu Ala Phe Ala Met Leu Ala Ala Val Pro Pro Val Phe Gly
            100                 105                 110

Leu Tyr Ser Ser Phe Tyr Pro Val Ile Met Tyr Cys Phe Phe Gly Thr
        115                 120                 125

Ser Arg His Ile Ser Ile Gly Pro Phe Ala Val Ile Ser Leu Met Ile
    130                 135                 140

Gly Gly Val Ala Val Arg Leu Val Pro Asp Asp Ile Val Ile Pro Gly
145                 150                 155                 160

Gly Val Asn Ala Thr Asn Gly Thr Glu Ala Arg Asp Ala Leu Arg Val
                165                 170                 175

Lys Val Ala Met Ser Val Thr Leu Leu Ser Gly Ile Ile Gln Phe Cys
            180                 185                 190

Leu Gly Val Cys Arg Phe Gly Phe Val Ala Ile Tyr Leu Thr Glu Pro
        195                 200                 205

Leu Val Arg Gly Phe Thr Thr Ala Ala Ala Val His Val Phe Thr Ser
    210                 215                 220

Met Leu Lys Tyr Leu Phe Gly Val Lys Thr Lys Arg Tyr Ser Gly Ile
225                 230                 235                 240

Phe Ser Val Val Tyr Ser Thr Val Ala Val Leu Gln Asn Val Lys Asn
                245                 250                 255

Leu Asn Val Cys Ser Leu Gly Val Gly Leu Met Val Phe Gly Leu Leu
            260                 265                 270

Leu Gly Gly Lys Glu Phe Asn Glu Arg Phe Lys Glu Lys Leu Pro Ala
        275                 280                 285

Pro Ile Pro Leu Glu Phe Phe
    290                 295
```

<210> SEQ ID NO 6

<211> LENGTH: 29485
<212> TYPE: DNA
<213> ORGANISM: homo sapiens

<400> SEQUENCE: 6

| | | | | | |
|---|---|---|---|---|---|
| aagataatgt | taaaaattat | ttcacaaacc | ttgcatcctt | agtgtattcc | agcattacgg | 60 |
| aatgaaggtc | accacaagaa | gtggcttcac | aacccaccac | aatctaaaac | aaacataaac | 120 |
| aatcaataca | caggtaagat | tagatgatac | tgaattccat | taattaaaat | cccatccgtc | 180 |
| catttattac | tctgataggt | aatattcaga | gaagctttta | tagagcagcc | tgctgggata | 240 |
| ccaagaatac | attcttttgg | attctgttaa | agatgttcaa | ttttgcatgg | agataaaaat | 300 |
| aaaggtttta | aaagttacat | ttctatgtac | taaattagta | taataaaaaa | ttaatcacaa | 360 |
| atctgggtaa | gataaactgg | ccaaaaagaa | agtaacatta | gtcaaattta | tagacagaaa | 420 |
| ctgaaagtat | cactgattca | aaacaatttc | attgatagcc | taactttctt | gattgttact | 480 |
| attaaatttt | tagttggaat | taaaatcagc | aattttaatt | acttaatatt | cgttcttggg | 540 |
| gttttctgta | tttccatatc | aatgaaagct | ttccatatta | tatgcaatta | aatgtttgaa | 600 |
| tcattaataa | tacataaatg | ctataaaaat | ttggtgattc | aaatttaagt | cctaatcatc | 660 |
| tatttaatca | tgtcctattt | cagcactgat | aactagggaa | ggttagtgtt | aaaaatttca | 720 |
| ggccatacag | tcatgaataa | aacaactcta | aattcagaga | gagaataaga | agcataatga | 780 |
| tagtgggaat | cataatacac | aaatataatg | ctgtggtgct | tcaaaggaga | tagtatttga | 840 |
| ttcagtggat | tagaaaataa | tcagatagat | agggtacatg | cgagctgccc | ctgaagactg | 900 |
| ggaagagtgt | gagaggtaga | gataggaaaa | agatatttag | gtgaaagaaa | gagtgtgagt | 960 |
| gaagacaaag | tagggaatca | tggtgggaca | tcaagagcac | agtatatagc | atgttttggt | 1020 |
| ccaagtatat | cgtatatgaa | atattcagag | atgaggttag | aatgatcggt | tgaatttggc | 1080 |
| agaccagaag | ctgcagccta | agtgtttga | ccttaatttg | gtaagtgatg | gagagtcatt | 1140 |
| aaaggtttct | gtggaatgat | gtgctgctta | gagatatgct | ttataaagat | caatctgacc | 1200 |
| atgatgtcaa | agacagatag | gagtggagag | agagagattg | ggagtgaaaa | gagtacttag | 1260 |
| tcaactgttg | atttagttag | ggccagaaag | gaggtggtga | tagtgcaaac | agagaagatt | 1320 |
| ggatggatac | caggaacact | ggaaagtaga | attcaaagga | tgtagtcact | gattagatat | 1380 |
| gaaaagtgaa | aaatcaaagc | ctagttgaac | atttcaagct | agttactagg | tgattggtgg | 1440 |
| tgccatcgac | agaaacagga | aaatcagagg | agttggtatg | gtgagggaag | atattaagtg | 1500 |
| caccgttaga | cacattcagt | tgaggtgcca | atgtgcaaag | gtgtagaaat | gtgtaggggc | 1560 |
| tattaaaata | ttgaattaat | tgttagccag | tcaaggttgg | atgtgcagat | ttgaaatttg | 1620 |
| ctcttcaaga | tatgattctt | gaagctagat | gattggatac | aattcctgat | ggtgagaatg | 1680 |
| tctatggaga | gagaagaaag | ttgatacata | ctgagaaatg | ctgacattta | gagggctgag | 1740 |
| gggagaaaag | ccataagaag | ataacagata | tcaaagaggt | agaaggagaa | cgagcagaga | 1800 |
| acccagaagc | ctaggggaaa | gagaattcca | caggttgaag | agggcaagaa | taacagtgtc | 1860 |
| aaatagtgta | gagaggaaag | agaaggtggg | gaatgtgcaa | aaactgttga | tattgggtac | 1920 |
| ggtaagtctc | tgctgacttt | caagtatgta | gttttagtga | tactttacta | aattttgag | 1980 |
| gatagactct | cttttttcc | taaagaaatt | gccttggtta | tagaaagaga | gacccagtct | 2040 |
| cttcagtgca | gttacttctg | ttacagaagt | aacaaaagag | gaggctccaa | tcaactcaat | 2100 |
| caaatataat | acctttgatc | tgggccacaa | tgtgaacctg | ggagagggaa | aatcttcact | 2160 |
| cttaaggaac | agggcttaga | agtagaggaa | gtgtaacact | tcttcatatc | actaagctaa | 2220 |

```
gaatactcct gaaggagtgg tagcatttgg ggagcttgcc ttaccctcca gtccccaaag    2280
gagagtttaa catagagctg aggcgaaaag caaatacatt tttatttctg ctagtaagga    2340 ttttttactat taactgtcat tgtagtacat caaaaaaggg tattagaata actgatgtct    2400
ttaaaatgac ctagtaatac aatacatttc tgtaatgact tttgtgtgtg tgtgtgtgtg    2460
tgtgtgtgtg ggatatggtc ttgttctgtt gccctagctg gagtgcagta gtgggatcat    2520
agctcactgt aacctccaac cactgggctc gagtgattct tgtgcctcag cttcctgagc    2580
agctaggact acaagtacat gccaccacgc ccagctaatt ttttttttttt ttttttttg    2640 gtagagatag ggggtcttgc tatgtttccc aggatggtct tgaactcttg gcctcagaga    2700
tccttcctcc ttggcctccc aaagtgctgg gattacaggt gtttgcaata gagatacatc    2760
aattgatatt gctttgcctt tctctgagtg tctattaatt atttatgtct tcactttcat    2820
cctatatgaa tcaagtattc agtttaaaat atttgagagt cctccttaat tttttgagga    2880
tttaggaagt tccaacagga ctaatgtagt ataggcatat gaagtcagag acacaagaaa    2940
atagaaagat acactggaaa aaaatagat ggagaaaaaa tggctcaatg cacataatag    3000
gcatggagta agataaagag gaaggggaga gacagcggaa gggaagggag agagagagaa    3060
ctgtgcaaca taaaaggag atagtgttac agagtagaga tagaagtagg cagagtgccc    3120
tatttgagct ttctatttac aagggtaggg agactgaaat ccagattaca tatataagat    3180
agaatatatt cagttggtgt aaaagtaatt gcggttttg ccattaaaag aattggcatt    3240
aaaagtaatt cctttttttt tttttttttt ttgagacaga atctcgttct gtcgcccaca    3300
gtgcagtggt atgatcttgc ctctcaggtt tcagcgatta ttatttctca gcctcccaag    3360
tagctgggat tacaggtgtg cactaccacg actggctttt ttattttatt tattttttta    3420
tagagacaag gttttgccgt gttggccagg ctagtctgga gctcctggcc tcttggcctc    3480
aagtgatcct cctgccccag cctcccaaag tggtgggatt ataggcatgg ttccactgca    3540
cccggcctgc aattactttt gcaccagcct aatagttaca tttcttgcta tgtcccaaca    3600
ttttcaggga ttttatctat cctcaagtaa tcatacttga ataaaggtct ttgcaaaaga    3660
tgacctcttt tattcataag ataaagtctt ttttaatgaa taatatcagt catttcctta    3720
tagttgtctg actaaccatt ctccctcgag gccccaaatg caatgctact ttctgtttta    3780
aagagccact tttccttact ttaaactgca tcatgtatcc tggctgtata atgagttctc    3840
gggaggagag agcattgtga gtcttgtcct tcttttttatt tggccaatag aggtgaaagg    3900
atggattgcc acaaaatcct gctgtcctta cagcattagg gtaaaaactc cagttttctt    3960
catgggaagt gccttctgtt aaggaaaatt ggaagcaata tggcatatta ttctcttgag    4020
gaaaattgga agcaatatgg catattattc tcttgaactg accgatttat tgttgaattc    4080
cttaaatttt tatgctctac tagctttctg cttcacttt aggattgatt tttattttat    4140
ttaactggga taatgcataa atccaacgtg agaaatcaaa ctttgacaag actattaaat    4200
ggtagtataa tgattaccgt acttttaaaa tgtaattgct agtctaggta acctagcacc    4260
gaaaagttct tgatacactt tgtcagccag tgcattaagt atttctgtga cacattaatt    4320
actaaagaaa ctaaaattat tttcgggtat tgaaatttca aattatattt aaagccagac    4380
attgagcctt taacatgatt tattgaatgc tcagtggaca tttcaaaaag cagccaactt    4440
tgaagattta taaccactg ggcaaaataa cagctaacat ttgttgagca ggagtatggg    4500
ctaggcactc ttataaatgc ttttcatgtg ctaatctatc tgaagacata agcagaaaaa    4560
```

-continued

```
tggctcacag gaaagaaaat tgttcaatgt cttgtttctt accatcatca aaagtgtcca    4620
ccaattggct gggattgatt tctgctccac caatcaaaat gttgtccagt gcccactgag    4680
cacgctccac cccagagacc acaattccat tgctgatcac aaaaggctgc caccagcgaa    4740
gtcgagttgt gttggtgagg gcatcttcag gaagaagtat gtagtcgtgt ctaacagaaa    4800
tgtatttctg gtaatccatc tcatggagca aagtccaggt aattcctata ataacaaata    4860
taccaacata gcaatatatc tagaatctcc tgcctcctca taaaccacca gtatacttca    4920
gatactgtga acttcccaaa gaaattttca gccaggaaat gacaactgat tttcctgact    4980
ttgatattag gtattcacta cttatactgt ttctgtatga ggctaatgat atgaggggaa    5040
ggatatttcg aaagagttgg ccaaaataaa aacactgaag taaaaataag ttatgttttg    5100
cttttaaaat ttagttctaa attcttattt ctcacaaata atgagataca cccatgtttt    5160
acatgtttct aggcaatagc tttcagtatt aaaatagtta ttgtaatttt atgcaattta    5220
attatttgga ctggtataaa gtttatctct tcttgcttga taagattgca ggtgggatgt    5280
ttaattactt aagaaaacat ccttcaaata ccttaaaata cttttagggtc atctgttaat    5340
cagctagtta ttaagaatga tatctatctg ctaaagcaga ttttttctaaa gacaccatgg    5400
tattactggt ctggttttag ctacttcaga ataacaaaac agaattctat taaaatattc    5460
tatgacaaac tcacaaaatc agacttttttt ttcacaattt tagaagatttt ccatagatta    5520
tagcatttat tacatgctta tttacacata agctgttaaa aatgctttaa agttttaaaa    5580
atgatctttt acttggaaat catacaaaat gtatttctta attgtatcac tcaagcttca    5640
gtaaagcgta gaggttgttt tctttattca taaagtttgg actttatttt taatgtgatt    5700
tctctccttc ccttttttgca taacacagaa gtcacttgta cggaacatgt aatacaaaca    5760
aaatctgtag cttttttcttt gtgagtttca caattcaaac tgtgaagtca gcaaagcttt    5820
gcagagactt ttctgagggt gttggatgga atttgggaat ctgctccaag gggtggtttt    5880
caccctgac acatgcctcc atcggtagag tagtccaaca gcacgccttc cttccggcag    5940
atgggacgat ggcaagaggt catgttgttc tcactaccga tgcgccccca gtattgcagg    6000
aacctgaatg caagcacatt ttatccatca gaataattca ttagaacaaa tactctactc    6060
aagtcctgga taatttcttc catacaagtg ttccttgctt tgggaccaat ttgctatggt    6120
gcaatagaaa taactaacaa aaaattcact tactttgcac ctcgaagatc caaatcttgt    6180
gtaaccgctt gtctcacagt ggatccccca aaatagagtg cagtgtcctc ggcaagaatt    6240
ccacactcag tgcaagtact tccaccttct aaggacatcc ataagtcagg tttgatttct    6300
tcactgtcaa agcgttcctt caggaaagtc tggaaataaa ataagccaga tgtggttaaa    6360
aaacaatttt cagataacta tggaatattt aagaaaatac agagtgatgt cttggactta    6420
aaaaaaatag agctgatttc aaatgctttt caaagatgtt taaaaaaggc tatttccaca    6480
atctttttttc ctgtcgtata ttgaaaatca tttaaactgc tcaaataatg tttaataatt    6540
gaaatttaaa ataattgtaa agttgactat atcaattttt ttttttgaga cgaagtcttg    6600
ctctgtcact tgggctggag tacagtggca caatctcaac taactgcagc ctctgcctcc    6660
cgggttcaag caattctcat gcctctgcct cctgagtagc tgggattaca ggtgtgtgcc    6720
accacacctg gctattttttt gtatttttca tagagatggg gtttcaccat gttggctagg    6780
ctggtctcga atccctgacc tcaagtgatc tgcccacctc cgcctcccag agtgctggaa    6840
ttacaggtgt gagccaccat gcctggccat attatagtaa cacttctatt tgtaaaaagt    6900
tagttagtta tttaagcata tacccccaaa catgtatatt tgtttatata gtatataaaa    6960
```

```
gtattattgt aatgtattat attatgaaac atgccaaaag gaatttgaaa gcaataagat    7020
aaaatataaa catgcaatcc agcactttcc ccctgacatt ccccaatgga ttgtcctggt    7080
gtgtgtgccc tcactttgga gactgcttca ggcagccagg atccttcagc ctctagcaca    7140
gaatgaacct tgaaggtcta catggttagg cagggacact tgaaaccaaa tctctctata    7200
taagtcaaaa gaaagtaaac ctttgaaggc agtttgaaag atgtttcacc tgtttatcag    7260
gccaagttgc agggtgataa gtactcaaaa tctagaatac aatattttcc cctgagtctc    7320
cagtttatcc ttttaactaa gaatgattga caaccagaaa atctattttt cagagagtgt    7380
acaaagtata aaggttcttg gctacatttt tttgtaaaat ttgcttatct cctcatagtc    7440
aaggtcttaa tttccctatt cattctgtct acagtacttt cattttatcc ataatgcaga    7500
tttgtattag gtagagacac atttcttgtt taaaatgatg aaaagatatc ataaagccaa    7560
tttgttctag ttgcaatgca ataactgtat acagaaaaac ctatatttt tcatttaagg    7620 agagttctat cttactgtgt agttaaaatg atttaaacag tttcttttc tcaaacttag    7680 aagataatca attctatagt taaagacata cagtcaaatg tcagtctgcc ttagtctcac    7740
taatggatag caaatgaata cgttttataa ttgaaagctt gtaagaagac aagtgttaga    7800
agaaatgcat ggttaaccac gtaaactttc attagaagat tttaatcagg gtttataatt    7860
tatagatttg tacaatttct tatccaactg aggaatacta ataaaatttg agtgctcatg    7920
aaagaaatta gattttcaaa agtttattaa ttacctgtgg tatataaagc tttgtttttc    7980
atgtggtaac ctcatttgtt aataatgtac ttacatcttc agacacaaat gagcattgtt    8040
ccaattttat ttaaaaaatg ttcaattcca tagttgaagt attagaacaa acacaaatga    8100
cagaacaggt ttgatttaca ttgttgactc tcatatgttg gatttcaatc actaggaatt    8160
ttgctttttt tagcctagtc attttctgt tattgtaatg acaaatgcac tatgtttatt    8220
cacagaaata gagtgcatat gtggcaactg tgttgggtaa ctgtatttgc tttgcatatt    8280
aaataatgat gtaacagcta aagctttcaa aagtgacctc tccattctta atacacaacc    8340
ccatttcagc agtcaacgaa tcagaacaca gaattttcta aacaaaaatt caggtactgt    8400
ttaggccttt ttgaaaattt ggtctttgt gataatgtat attatttgct ttatttcata    8460
acaataataa caataatatc ttccttcaaa tagtgcatca attgaaaaag tgaagtaaaa    8520
aaggcttaat attgactta aaaatagtct gcttaagaaa aaaaaagaa acccagagta    8580 tttatcattt gtaatccata tagtctggct catttatga actggataaa ctgtactaga    8640
acttgatcct aatattcttg tacttaggaa acataagaca ttttaaagt ttctattcaa    8700 aggattttct ttcctggggg acccaaagga cattgttata gattatgtct catacataag    8760
ttggttccta ggcatgaccc atgatgtgag taatgcgtct tgtccagggc tttacccta    8820 ccttcagagt gtgggtcaag tagcagtttg gccctgagta tccggatca cagatgcact    8880 gttccctaaa gcaatctcca tggcccctgc agttgtccaa gcatccaggg cccaggtaga    8940
aattatcgat tgcccactgc atgtctgagt acttctgata gaacctaaac cttaccggac    9000
tattgacaat gcaaaagcaa aggagtgaaa aacaaaagtt aactgtattt aggtccattg    9060
tcctgcatgt gtattcagta ctcaagagaa aaaacattta agatactctt actagatgaa    9120
ataggttaat aaaaaatgtt ttctgaccac tcttatcttt ctagtaatgg aactttcaag    9180
ctggttttat tgaaatttca gaatatctga gcacacttgc acaacaaaat taaatcagtg    9240
gaatctctgt gtcaagaaat aaatagaaat atttaaatac acaaatctgt aactttcata    9300
```

-continued

```
aatcaggttt cttctgaatt ggagttccgt ggtcatgatg caatttagat tcactaattg    9360
catttctgaa attgtacaga aggtgagtga cgcctttgac aagagccttg tcagcataca    9420
cacagccctc aggcggtcgg gaggcagcat tttctgaatt ccctgaagac aatcaatatt    9480
ctcagagtaa ctatgctaat tagaaaacaa ttttgaaagg gttatattaa aggacatttt    9540
ctttgagatt ttaatttcat ctttgttctt ctctgtcttc tgggggaaaa aacaagcctc    9600
ataattatcc ttatattaaa atatgccata ctattttggt ttaaagaatc caaagtacat    9660
gaaggaactt tctggggtga tataaatgtt ctgtatcttg ttttatgtgg tggttacatg    9720
ggttacacaa ctaaaaactc attgatctga acaattaaga tgtatgtatt ttactgaatg    9780
taaattatac ctcattatta caaaagaga atgggaggag aaaatgagtc tgtgatagac      9840
atcatggtgg gtccccagca tccatttcac cccagataat ccatgaaata atcatttcct    9900
aactcaacta ttgagtggct aattggtacc agtgggatgc aagtggcgc ttgttctggc      9960 tgtcttggaa caaaagcaac tatctttctt tctcactgga cgtaagtacg aagcatcct     10020 gccccagttc tctggctgcc atctcatgtt caatagcaaa accagcctga gagagctgag   10080
tatgccgcca gtgccgtgga cagcagatat tctcttaaga ggataaggag gaacgctgtc   10140
cctgaagaca ccgttcaact tacaaatcaa ccagccctag agttcactta tctttggatt   10200
cgttcattat agatataaca aatttcgagc tggtttgaat tgggttttct gttccttgca   10260
gctgaaagca tcctgattta attccttagt atgttaattg aataagctct ttagatacat   10320
tccagaaaac cctgagtggt aataataata ataataatat ctatgggaca ctgggaactg   10380
tgcgtaagca ctttattcaa agactcttta tgtttcacaa gatttgttta gtcagactat   10440
ctgattaata cagtctaggt gcacctgtta tttttctttt gtgtatcttta cttttaaagt   10500 agaagagaaa tcttttggaa ttgccttaaa ttaatatatc cacagacttt gcagagcaag   10560
gtttaatcac ctctgctcat cactggtcca ggctaattac ctctcactgc aggatcagaa   10620
tacaatgctt tgataagaga aaaatggatc ccataagtca cagtggtaga aatagcatga   10680
tgagttagga tttgctcctg gctctgtcta tcatggattg ataaggcaat aatgtggaaa   10740
gtatatagtg cacagaggtc cacagtctac aaggttgaga aggtagggta cacctttttca   10800 tctggctcca aggccatcac tattgctctg ttcccatttt aagatactga ggtttagaaa   10860
ataagagtct gcaaaagccc atattgccaa gtctgaggat tacaaattga ggtctgaagt   10920
tagctcatca tggaagttat gatgaaagta accaattaga gaacctttag agttagggag   10980
aaagaaagca ctttacccac aaatacacat aatttcaggc atgacaacag tgtacctaat   11040
ggtgtacctt ctggatgctt ggaaccaggc tttgttttag ttttctactt actttcccac   11100
taagctttca ggaagtgggt aggtgatcct tttccaccct ttagttggaa agaatacaga   11160
tggctgagaa acacttccag agcatttggg gtcagcaggc aagcactgag ggaccagata   11220
attccaactc acaccgaagt cagtagaata ctgcacatga atttgattct gggcaatttt   11280
ttcagacacc ttcatccaa ctgagatcta ataaacagaa aaacaagatc aaggtattaa     11340
aactatatga tatgattctt ctccaaggac ttggcagcaa aaaagctgct gatcacttga   11400
tatacactgt accacatcca tcctgtattt tcagattcat tatttgttct gctaatggac   11460
agagaaagtc accatgattg ccccaggtga caaattatag aaagtgccaa atatattgtg   11520
tagggggttt ggagagaaac tcagaccccg tgcttctgcc atgctggctg aatgccttgg   11580
aaggcctggg ctcactccta caaactgtta gttgtgctaa tggtctggca tttctatttg   11640
gcagaatact taaccaagaa gaatagctaa cagctttacc aatttttacta ttttgttgta   11700
```

-continued

```
caatttatga ctctcaatac aacactttca acgacaagta agatgaaata ataactgaag   11760
gtagtttaaa caaggcacag cacccttcgt tgatggtgat agccatgatg tgacactgct   11820
gttaatacag tgggatttag gtagacagaa taaattggtt cacataaaat cttggcctaa   11880
atattagcca aaattgatgt tgacattaat gctaatcatg cctttgtttt ctataaattt   11940
ttttctccag aaacatccaa atgttcttgt aaaaaaaaaa aaaaaaaaaa aaaaactaga   12000
ggctgggtgc catggctcac gcctgtaatc ccagcacttt gggaggccga acgggtgga   12060 tcacgaggtc aggagtttga gaccagcctg accaacatgg tgaaaccctg tctctactaa   12120
aaatacaaaa attagctggg catggtggcg tgcacctgta atcccagcta ctcaggagcc   12180
tgaggcagga gaatcgtctg aacccgggag gcagaggttg cagtgaacca agattacgcc   12240
actgcactct agcctgggca acagagcaag actccgtctc agaaaaaaag gtcttatttc   12300
acctaaattt ctaagttata gttagtatta atagagagat gggtaagagg aaaaaaagta   12360
gaataaccaa ttatagcttt aatttttctct tgttgaaaca aattgcttaa gtcataatga   12420
tttaactcgg agttataatc agtatcctac attttttattg ttgatatttt tatctatcag   12480
tatttcatcc tgagcaggaa cacatttact cttataaaag tttcagcttg agagacagct   12540
ggcaagatgg ctgaatagga acagctccag tctgcagctc ccagcaagat caatgcagaa   12600
ggtgggtgat ttcggcattt ccaactgagg aacccggttc atctcattgg gactggttgg   12660
acagtgggtg cagcccatgg agggtgagct gaagcagagt gtggcagaac cacaaggggt   12720
cgggggattt ccctttccta gccaagggaa gccgtgagca actgtgctgg gaggaacagt   12780
gcaatctggc ccagatactg cgcttttccc acagtctttg caactggcag accaggacat   12840
tcccttcggt gcctggctca gtgagtccca cccccacgga gcccagcaag gtaagattca   12900
ctggcttgaa attctcgctg ccaacacagc agtctgaggt cgaactggga tgctcgagct   12960
tggtttgggg aggggcgtct gccattactg aggcttgagt aggcggtttt cccttcactg   13020
tgtaaacaga gccacccaga agtttgaaat gggtggagcc cgcctcagct cagcaaggcc   13080
aactgccact ctagattcct cctctctggg caggcatct ctgaaaaaaa ggcagcagcc   13140
ccagtcaggg acttatagat aaaacttcca tctccctggg atagagctcc tgggggaagg   13200
ggtgctgtgg gcacagcttc agcagactta aacgtccctg cttgacagct ctgaagagag   13260
cagcggttct ctcagcacag catttgagct ctgataaggg acaggctgcc tcctcaagtg   13320
aaaccctgac ccctgtgtat cctgattggg agacacctcc cagtagggc cgacagacac   13380 ctcatacagg agagctccgg ctggcatctg gtgggtgccc ctctgggatg aagcttccag   13440
aggaaggaac aggcagcaat ctttgctgtt ctgtagcctc tgttggtgat acctaggcaa   13500
acagggtctg gagtggacct ccagcaaact gcaggagacc tgcagcagag gggcctgact   13560
gccagaagga aaactaacaa acagaaagga atagtatcaa taccaacaaa aaggaggtcc   13620
actcatagac cccatcctaa ggtcaccaac atcaaagacc aaaggtagat aaatccacga   13680
agatggggag aaaccagcgc aaaaaggctg aaaattccaa aagccagaaa attccaaaag   13740
ccagaatgcc tcttctcctc caaggatca caactcctcg ccagcaaggg aacaaaacga   13800
gatggagaat gagtttggca aattgacaga agtaggcttc agaaggtggg taataacaaa   13860
ctcctccaag ctaaaggcgc atgttctaac ccaatgcaag gaagctataa gaaccttgaa   13920
aaaaggttag agggactgct aactagaata accagtttag agaagaatat aaatgacctg   13980
atggagctga aaaacacagc acgagaactt cgtgaagcat acacaagtat caatagccga   14040
```

```
atcgatcaag tggaggaaag aatatcagag aatgaagatc aaatcaatga aataaagtgg   14100
gaagacaaca ttagagaaaa aagagtgaaa agaaacaaag cctccaagaa atatgggact   14160
acgtgaaaag accaaatcta tgtttcatca gtgtatctga aagtgatggg gagaatggaa   14220
ccaagttgga aaacactctt caggatatta tccaggagaa cttccccaac ctagcaaggc   14280
aggccaacat tcaaattcag gaaatacaga gaacgccaca aagatacata atcgtcagat   14340
tcaccaaggt tgaaatgaag gaaaaaatgt taagggcagc aagagagaaa ggtcgggtta   14400
cccacaaagg gaagcccatc agactaacag cagatctccc tgcagaaacc ctacaagcca   14460
gaagagagtg gaagccaata ttcaacattc ttaaagaaaa gagttttcaa tccagaattt   14520
catatccagc caaactaagc ttcataagcg aaggataaat aaaatccttt acagacaagc   14580
aaatgctgag agatttttgt caccaccagg cctgccttac aggagctcct gaaggaagca   14640
ctaaacatgg aaaggaacaa ccagtaccag ccactgcaaa aacataccaa attgtaaaga   14700
ccattgatgc tttggataaa ctgcataact aatgggcaaa ataaccagct agcatcataa   14760
tgacaggatc aaattcacac ataacaatat taaccttaaa tgtaaatggg ctaaatgccc   14820
caattaaaag acacagacta gcaaactgga taaagagtca agacccatct catgtgcaaa   14880
gacatacata ggctcaaaat aaagggatgg aggaatattt atcaagcaaa cggaaagcac   14940
aaaaaagcag gggctgcaat cctagtctct gataaaacag actttaaacc aacaaaggtc   15000
aaaagagaca aagactggca ttacataatg gtaaaggaat caacgcaaca agaagagcta   15060
gctgttctaa atatatatgc acccaataca gaggacccag attcataaag caacttctta   15120
gagacctaca aagagactta gactcccaca caataataat gggagatttt aacaccgca   15180 ctgtcaatat tagatcaacg agacagaaaa ttaacaagga tatctaggac ttggaagtca   15240
cctctggacc aagcggacct aatagacatc tacagaactc tccacctcaa atcaacagaa   15300
tatacattct tcttagcacc acattgcact tattccaaaa ttgaccatat aattggaagt   15360
aaaaaactcc tcagcaaatg caaaagagcg gaaatcataa caaactgtct ctcagaccac   15420
agtgcaatca aattagaact caggattaag aaactcactc aaatccacac aactacatgg   15480
aaactgaaca atctgctcct gaatgactac tgggtacata acgaaatgaa ggcagaaata   15540
aagatgttct ttgaaaccaa tgagaacaaa gacacaacat accagaatct ctgggacaca   15600
tttaaagcag tgtgtagagg gaaatttata gcactaaatg cccacaagag aaagcaggaa   15660
agatctaaaa ctgacaccct aacatcaaaa ttaaaagaac tagagaagca ggagcaaaca   15720
cattcaaaag ctagcagaag acaacaaata actaagatca gagcagaact gaaggagata   15780
gagacacaaa atacccttca aaaaatcaa tgaatccaga agctggtttt ttgaaaagat   15840
caacaaaaga gatggaccac tagtgagacg aataaggaag aaaagagaga aggatcaaat   15900
agacacaata aaaatgata aagggatat caccactgat cccacagaaa tacaaactac   15960
cgtcagagaa tactataaac acctctatgc aaataaacta gaaaatctag aagaatgga   16020 taaattcctc gacacataca ccctcccaag actaagccag gaagaagtcg aatccctgaa   16080
tagaccaata acaatttctg aaattgaggc agtaattaat agcctactaa caaaaaaag   16140 cccaggacca ggtggattca cagctgtatt ctaccagagg tacaaacagg agctggtacc   16200
attccttcta aaactattcc gaacaataga aaagaggga atccccccta actcatttta   16260
tgaggccagc atcatcctgc taccaaaacc tggcagagac accacaaaaa aagaaaattt   16320
caggccaata tcccttatga atattgatgt gaaaatcctt gataaaatac tggcaaacca   16380
aatccaacca agatcaagtt ggcttcatcc ctgggataca aggctggttc agcatacaca   16440
```

```
aatcaataaa cataatccaa catataaatg acaaaaatgc catgattatc tcaatagatg   16500
cagaaaaggc cttcgccaat attcagtagc ccttcatgtt aaaaactcaa taactaggta   16560
ttgatggaac atatctcaaa ataataagag ctatttatga caaatccaca gccaatatca   16620
tactgaatgg gcaaaaactg gaagcattcc ctttgaaaat aggcacaaga caaggatgcc   16680
ctctcttagc tctctctctt attcaacaca gtattggaaa ttctggccag ggcaatcagg   16740
caagagaaag aaataaaggg tattcagtta ggaaaagagg aagtcaaatt gtctctgttt   16800
gcagatgaca tgattgtgta tttagaaaac cccatcgtct cagcccaaaa tctccttaag   16860
ctgataagca acttcagcaa agtctcagga tacaaaaatc aatgtgcaaa aatcacaagc   16920
atttctgtac accaataaca gagagtcaaa tcatgagtga actcccattc acaattgcta   16980
caaagagaac aaaatactta ggaataatac aacttacaag ggatgtgaag gacctcttca   17040
aggagagcta caaaccactg ctcaaggaaa taagagagga tgcaaacaaa caatggaaa   17100 aacattctat gcccatggtt aggaagaacc aatatcgtga aaatggccat actgcccaaa   17160
gtaattatag attcaatgct atccccatca agctactatt gactttcttc acagaattgg   17220
aaaaactact ttaaatttca catggaacca gaaaagagcc tgtatagcca agacaatcct   17280
aagcaaaaag aacaaacctg gaggcatcat gctacctgac ttcaaagtat actataaggc   17340
aacagtaaca aaaacagcat ggtactggta ccaaaacagt tatatagacc aatcaaacag   17400
aacagaggcc tcagaaataa caccacacat ctacaaccat cttgatcttt gacaaacctg   17460
acaaaaacaa gcaatgggga aaggattccc tatttaataa atggtgttgg gaaaactggc   17520
tagccatatg caaaaagctg aatctggatc ccttccttac accttattca aaaattaact   17580
caagatggat taaagattta aatgttaaga cctaaaacca taaaaaccct aaaagaaaac   17640
tcaggcaata ccattcagga cataagcatg ggcaaagact taatgactaa acaccaaaa   17700 gcaatggcaa caaaagccaa agtagaccaa tgggatctaa ttaaactaaa gagctcctgc   17760
acagcaaaag aaactattag agtgaatagg caacagaatg ggagaaaaat ttgcaatcta   17820
tccatctgac aaagggctaa tatccagaat ctacaaagac cttaaagaaa tttacaagaa   17880
aaaaaaaaca tcaaaagtg gtcgaaggat atgaacagac acttctcaaa agaagacatt   17940
tatgtggcca acaaacttga aaaatgctc atcatcactg gtcattagag aaatgcaaat   18000 caaaccaca ttgagatacc atctcacacc agttagaatg gcgatcatta aaaagtcagg   18060
aaacaacaga tgctagaggg gctgtggaga aataggaacg cttttacact gttggtggga   18120
gtgtaaagta gtgcaaccat cgtggaagac agtgtggcaa ttcctcaagg atctagaact   18180
agaaatacca ttgcacccag caatcccatt actgggtata tacccaaagg attataaatc   18240
attctactat aaaaatacat gcacacgtat gtttactgcg gcactgttca caatagcaaa   18300
gacttggaac caaccaaatg cccatcaatg atagactgga taaagaaaat gtggcacata   18360
tacaccatgg aatactatgc aaccataaaa aagatgagtt catgtccttt gcagggacat   18420
ggatgaagct ggaaaccatc attctcagca aactaacaca agaacagaaa ccaaacacc   18480 acatgttctc actcataggt gggagttgaa caatgagaac acatcgccac agggagagga   18540
acatcacgca ctgtggggcc tgtcggggag tggaggaggg atagcattag gagaaatacc   18600
taatgtagat gacggtttga tgggtgcagc aaaccaccat gccacatgta tacctatgta   18660
acaaacctgc atgttctgca cgtgtatccc aaaacttaaa gtataataaa aaaagatgaa   18720
aaaaagtttc aacttgaaat agttcagaaa taaaatactt ttaatcatta agcaatgtat   18780
```

```
agttgagttg tatattagtt taatagtaaa ttttactttt caaagtatat actaagtcaa   18840
tgaaatatta gatcatcttt tctctgatat tttttgttat attgctaatg tatggttgtt   18900
tatataatca agatcataac atttcacctt gaattgcata atccagcctt cagtgggagt   18960
caggtcatgg gtcactgcat acacctcccg tccatcatga ctgccacaga gcatcacacc   19020
atcaggggag tcacagaatc tttctactgt acaatcatca tggaatagcc agtgctcatt   19080
cacttaaaac aaaaaaacaa aattttatga caaatttgtg acaaaaatac ttgaagcaaa   19140
ttttcacttt aagcaagaca tagaattatt ttaagtagaa actgctcata ttatatacac   19200
tctatagaca aaacactaat ataaatacat tgtttcagga acataaatac taggaggatt   19260
gagatatatg ccctttgtct gatattagta cacacacaac catagatatt agtctacaca   19320
tgaaaaaaag tatattgtac acattgtaaa tgaaaatcaa aaggaaataa ctaattttt    19380
gacagatatt taacttttta gatagcatat aaagaagtag agatgatttt taattttaaa   19440
aattttattt acagtgtctc gtttattagg aaagaatcat gaagaatcac aattgcactg   19500
ggctggtcat tttattttat tttttttaat accggatagg gaatagagtt aactactact   19560
cacattctga aagtattatc tgggtaacta aaaagcttgt aatgaatttt ttatagcttt   19620
atcaagatat aactgatata caaaaatgac acacatttaa aacatacatc ttggctgggt   19680
atggtggctc atgcctgtaa tcccagcact ttgaaaggct gaagtgggag gatcgcttga   19740
ggccagcctg ggcaacatag tgagatcctg actgttaaaa aaaaaattag ctggagtggt   19800
ggtgcacgcc catagtctca gctacttagg aggctgcttg agtccaggag ttcagggctg   19860
cagtgatttg tgattgtgcc actgcactcc agcctgggca gcagagtgag accctgtctc   19920
taaaaaattt gttttaaaaa atgaaatata catttgatga ctctggaaat atgcacaacc   19980
catgatacta tcaccacaag cagggcacca aatcgatcca tcacttccaa aaatttcctt   20040
gtattctttt gtgtgtgtgg tttttagttt ttgttggggg gttgctgttt agaacaccca   20100
acaagagaca tatcctctta acatatgttc agtgcacaat ataatcctgt caaccataga   20160
cactatgtca tacagcagat ctctagaact tatttctttt gcatgacaga aacttttatag  20220
ctactgaaaa agtattcatt tcccctttct ccagatcctg gcaaccaccc tatttaatta   20280
gataaacaaa tgattttga gtttaagaaa tgagtttata acaaacttgt tataaaggct   20340
aattttaagt cctataatgt gaagccatgt ttaatttggc caaaagtaaa ataaaatctt   20400
attaaataga ttatttaaga aattaggatt ctaagataat actgttataa atttaccttg   20460
gtaatgttct taatatttga ttatttatgt atggatattc aagtattctg gatagatatt   20520
tcttttaata agtcttgact cctaaacctg attaacagtt aacactttga ggaaatgtac   20580
tcatcaagat actactgaag aaatagattt gaaggtgtct aaagaaaacc taagtagtaa   20640
gactatgaat tgattaatgc agagtacatc ttgtgtgttg atcctctctc tctttctctc   20700
ttaacccctt cctccacaac cctcacagtt ccttttctct tctggaagag atgattttac   20760
attaatttta tccagaaaaa gttagaaatt aaacatatcc ataatatatg ttgcatctca   20820
ttcacagtat gctttgattt tataggtcca attcttttct aaaagtcttc tggctagtcc   20880
cagcatttcc agggaagctg aacaggtgca gccggaggct tggagccact atggaagcag   20940
cacagttgat gcctcagagg atccagagaa aagaccagat aactataatt cagccttcac   21000
ccatattgtg tcttttgat tttgtctgag tatatatgcc gcacaacaag cagcttatct    21060
ctgagattca aatagttact gcaattccat tatctgttt tttactgtga gggatttgga   21120
gccacattta gtcctacatc acagatacag gactcaagag tcaaagtgca cagaaatttg   21180
```

```
aattccgata agaatactct gagccagttt attctggggt acatacttca ttttatgcta   21240
gaactctgca atcctgatga aagagggctt gcattgctca actaactaac tcacccgtct   21300
ctcctgcagt attagaaact acttctgtat gtacacgtta cagtttctag gaactccatt   21360
tttgcaagac agataggagc cagaaaattt gttccttcaa ctgtatatcg ctaattaaac   21420
ataaaatcaa atcagcattt taggtacttg aataactagt ctgtgcttac ttttattcat   21480
atggaagcag tgtttaaatt attctctgat tgtaaactca cttatgtaaa ccattataca   21540
ggaaaaaaat gagtaatgaa gcaaagttct gaagcagatc tatgtaagca aatttcaata   21600
accttcttaa gagaatatga cacttagtag tggtgaggga cattttaagc tttttctatt   21660
tacaagtttt ttttaaacga gggtgtttca aagtaaatat ttgctgttac gttatgccac   21720
atgatatact aataaatgaa ttaatgaaat taacctaaat atccagtatt attattgaat   21780
atatagctac taaaatttta tattcaaata tatccaagga catgaggaaa taaggattta   21840
attctaaaca aaaaagaag ctatgaaata tatataattt aagactataa ttttgttaaa   21900
aatatgttta tgtaaatgcg ctaaaaaaag ttctttaaga atatatgcca aaatattgac   21960
aatggttatc ccctgagtga ttttatttt catccttagg attttctgta ttttctgttt   22020
cacattttga acatgtatac ttttacaaga aaatatgaac taaaattaaa aatttttaaa   22080
ctcctcaagt ttcaatttt tttttccagg acatgctatt cttctggaag attcttatca   22140
gtcttattat tgtaaaaatg aaccagactg tcttttccat gcaagttgct aggggctgag   22200
ctgggtgtga cagagttcca ctgtctgaat caatactggc ataacagtat atcaatcttt   22260
actatttaga tacatgctag tatgggatat ataatgaata tcactgcttt atctgaagat   22320
accatgtttc atgtagtata acaaatatgt ggcatggcaa agatacatac ttaatataag   22380
acaccacttt ttataaagat gaccagaata gtgtcatgaa atgaaaacaa gacattaaaa   22440
atgagaggag gataggccgg gcatggtggc tcacgcctgt aatctcagca cactgggagg   22500
ccgaggtggg cagatcacct gaggttgggg gttcaagacc agcctggcca acatggtgaa   22560
accccatctc tactaaaatt acaaaattag ctgggcatgg tgtcacatgc ttgtaatccc   22620
agctactctg gaggctgagg caggagaatt gcttgcacct gggaggcgga ggttgcagtg   22680
agctgggatt gtgccattgt actccagcct aggcaacaag aatgaaactg acttaaaaaa   22740
aagagaggag tacaaagagg tccttcctgc ttcaccaata tcattgaata ccctataggg   22800
gaatgaaggg taacaagcaa gacctgggac atgacctaag acatgaaatg ccattacaaa   22860
tgtgtctgcc ctgtagcaaa acacaatatt tgtcttcaga tactaaaaca aatgactggg   22920
aaatgtcatt tgttgggcag aagatttggg tagaaatctt tggcttttcta cccaaaatag   22980 aaaacaggaa acactgaaaa ttttctaaga aaagaaaatc ctgttaataa aattatagat   23040
tgctatatat aaaaacacac tagctggctt gaatgaaaga aaagatttag ttaaaatgcc   23100
aactaggaag gctgagagga acaaaaggat gacacccttt tcagcgtttc tacaccactg   23160
gaacatctga aaaggttcca tatttgctc ttttgaaaag acccaaatcc aaaccactgc   23220
atttccactg ggcttttat ttagcgctgt gcataattta cctgaagttt tgtcttccat   23280
aaacatgtca aaggcgatcc tcccgacagg gccggcatct gcagggagc gctcatgctg   23340 gggtactggg gcgctgctga aggtgtccag cataacggtc ctttggtcag cagagcctga   23400
gatgaggaca ttgtcaatgg cccagtcgtt ctgatccagg ccgtcatgtc ttggctgcca   23460
ccagcggaag cgagtggcaa tctctttagc atcaggaggg agaaggatat tcacaaatct   23520
```

-continued

```
ataggaaaat gatggggaag ggtgtgggga agaaccctttg tcaaatatct tctctgagta      23580
aaagatttac aaccagccat aagataatgt atgtcacatg gtgggtgagg aaggacata      23640 agctaaaata attttcaaaa accacgatta actggcttaa ttttatgaag tctcagtagt      23700
cactaaattg ggggaaatag aatgtgaaca gattcaagta tcccagaact cccaattggt      23760
tctgtctctg ggcaggcttt agagggactg cacagttttt tgcatacctg gtgggtatct      23820
gtaggcctag agtatatgca ctttggtaga cataagccaa tgctgacttt tttctgtcac      23880
ctagtgcttg gcttcttctg cttccttccc tggcaccttg ttttcactct gtttccatga      23940
gtgctggcaa gtgacttggg gtatggacac tggattgtgg gaggacattt gagttctcag      24000
cctgagggta ccaggtccat tatcagttgt ctgtggtgca gacactgact ttgtttatat      24060
gctttgttga aaatatttaa aattgtatat attcatagaa aatgtcatgt gagaaccatg      24120
ggctagcaag cccagcatgc tatctatccc tgtctcactc accagggaca gacatggaaa      24180
aatgtggctc catgctccaa cagaaaactg aattagctag aaataaggtc taaaatgccc      24240
tttaatcaca attatacatg aaaacccagg aacatatcaa cctcttgaat ttatattcat      24300
aactcataaa atctgttggg gaagataatg tccttagatt taccatcctc ctcacaaagt      24360 atctttttttt ttttttttttg agacagagat ctcactctgt tgcccacgct ggagtacagt      24420
ggtacaatct cggctcactg caacctccgc ctcctgggtg caagcaattc tcctgcctca      24480
gcctcccgag tagctgggat tacaggcgcg catgccaaca tgcctggata attttttgtat      24540 ttttagtaga gatagggttt caccatgttg gccaggttgg tttcgaactc ctgacctcgg      24600
gtgatccacc cacctcagcc tcccaaagtg ctgggattac aggcatgagc caccatgccc      24660
agccagtatc atcttatttt tttaatctat gctaatctac ctccctttag aggcatacct      24720
caagggatgc cttttcgtgt ttgcagaact ccaaggcaag acaaccagtc caagttcatc      24780
ccatgaagcc ctttaaactg agggcttcag tgacagtttt agttcttgtc tttcacatta      24840
aagagatttc attatattaa ttttgtttat acagtatctc catgttgatt ttatttttcc      24900
ttcctttttt ttttctgtct tccttgaggt agagtggcca gaacagtagg tagtattcca      24960
gatggaggcc aaccaagatt cactcacagg taggatgctt ttagctggat ttatacaact      25020
tgaattttaa atacttttttt ctattatgcc atcattctgt gcgccctttg ggccatgata      25080
gcttaatgga tcttagtctt agggaagaac agtgtagtct agaaagtatc aatcttagac      25140
cctcacctgt gcgggtactg gcagctggga gacatcaccc tttatgcaga gtcttttccg      25200 aagtctatttt cctcatttat gtcaattttg aagctcatct gtcttccctg cacctttttt      25260 tttttttggta tgcttatctt gtgagatgtt cctaacatttt acctctattg gtttgacatg      25320
tttacatact atccgaaatc tgtcagtttc tgggggacac acaatcgcac ttcttcacac      25380
agagcaatga tcttttatct ctatttttttc tttcctaatt ctaaattagt ttttatttttc      25440 tctgataagt cttttgaccac attttaaaaa tctctggaat ggaaatttac ctaaggctac      25500
ttgaaagtct aaataaatta taaccactttt tcctacctca gtcaatttga ttccccttca      25560
gagaactaaa gtagattaga cagttatgct tttaccctac agaaacataa ctctcttttc      25620
cttgcactaa cgttatgctg cttaagtgtt caggaactca cacttgaggt ctttataaat      25680
tcctccatca agaccaagga aacagtttac ttggcttgtc tgttatctcc tactaacagt      25740
tgagcacagg gtactctgta ccacttagct tctagttgga ttcctttatt ggtgtccaac      25800
tttaatgcaa gtggaagatt taaaagtttt gcttgtgca aaaactgctg gtatttcctc      25860
agtggccatt ctccctttct tccttcctaa taggagcctt ttcatccaag tgactggtcg      25920
```

```
cccagaataa agacagcatg tccagccttc cttgcatctg ggtgtggcta tgtggctaaa   25980
ctcaatagct aatggaatat gaaaggaagt acgtgcagct gttaggaaat gtccttgaag   26040
agagagcaca cccttctcgc cccaatctcc ttcctatgga ctgtaaagtt ggggagctag   26100 tggcccttt ggaccatgag atgaaagtca catgctgagt ggggcagaac aataagacag    26160
gaggaacctg ggtcactggt gcttgcggag ccactacagt agtcctggag tactttttt    26220 ggggatgtaa tttacatagg agagagagaa aaattaagta attttgtctt tcctgccatt   26280
gacagctgaa cctattctta actgatatat tgaatttaaa tgatcattta taagattctt   26340
tttattttac tcaaatttta gcctgtatct ggcttgcatg cattaaagga ttatctacgt   26400 ttccttttt tttttttttt tttttaaag atgcggtctt actctgtcac ccaggctaga    26460
gcatagtgcc acaatcatag cttactgcag cctcaaactc ctgagctcaa gcaatcctct   26520
tgcctcagcc tcctgagtag ctgggactac aggcacatgc caccacaccc aggtaattta   26580 agttttttt tttttggta aaatgtcttg ctttgctgcc caggctggtc ttgaactcct     26640
ggcttcaagt gatcctcctg ccttggcttc ccaaagtgct gggattacag gtgtgagcca   26700
ccatgcccag catgtgtttc ctgtctgggc tatatttatt tcctcttctc ttcagcctcc   26760
ccctggaccc tgccttttct ctctctcat tcttttctgtc ttctcttttc ttaccctctt   26820
cctcctccta ctttactgaa tatgctattt tccttcttaa caactctttg acatttctaa   26880
ttggtcataa tcattgcttt cggcccttca gtacttttt taaaatgacc catacgttgt    26940
gtttattcaa ggttttaaa taaggagttt aaaaataatc tctaggcttc ttaaggatat    27000
ttacatttta ttgtgtttct ttgctttcca gtccaaaatt ctctaaaaac agagtgtaca   27060
ctatataaat aaatatttat ttttctgttt ccattttccc aaagcattgc tgaaattaat   27120
tatactagtt aatttctgtg ggtttttgca ctgggtttat tcaccgttgg cattgtggta   27180
gaatatttca tcttattctg ggatgtgaaa actagttgtt cttaaaataa aacccaaac    27240 cagctattta tccagctcag aaaccottct tcatttcagt ctcagaggca tcctctagtg   27300
aggcataagt ctgaggtccc cctcagtctc ccgtgactga ttgctggtag caatctctgc   27360
tcgatgtact cgttattaga tatcaaatcg aatacaaacc cgggcttact gtactggtca   27420
tagaaaatct ccatgagcag gttccaggta atgcctccat tgacagaata ttccaagaga   27480
acaccttggt tacggttgtt tggtgtaatc aggcacccat acatgaagta aaattggatg   27540
aactcagcat tagtgaggtt tagatccaca gtgactaata atcgactaca accctaagaa   27600
aaagaagtaa aataaaaaaa agtgataagg aatctcgatt gcagattata gattttctat   27660
ggattttttt tttttttgag acagggtctt gctctgtcac ctaggctgga gtgcagtggc   27720
accatcacag ctcactgcag ccttgacctc ctgggttcaa gtgatcctcc cacctcagcc   27780
tcccaagtgg ctgggactac gggtacatgc ctccatgtct agctaatttt ttgtagagac   27840
agggttttgt tatgttgtcc aggctggtct taactcctgg gctcaaatga tctgcctgcc   27900
tcggcctccc aaagtgctgg tatttccatt ctttaatat ttattttgtg ataccagcca    27960
catagtattg tggcactgat tttcttaccc tcttcttac tatgctagct cttagtattt    28020
tgcctagtac acagtaggta cccagcacat gtttgctgaa ctttgaaatt tcagcattca   28080
agacttattt acagagaaca atgtattcca agataatttt ctgtttctt tttccttttt    28140 tttaatatga atgttatttt gggccaaggt tgagtatcgc agcccaggac acatttccaa   28200
gttgccttgg ctgtttttt ttcataagca agatgagagc tggaactaat ataactgtcc    28260
```

```
tttatttta ttaaactatc tccagttatt ttcagacact attagatttt taaaaatgaa   28320
tcaaccacta agaaaatagc atattgagat gaccatttta ttatgattat tattatttaa   28380 tttttttgaga cagtctggct ggagtgcagt ggtgcagtct cggctcactg caacctccat   28440
ctcctgggtt caagtgattc tcttgcctcc gcctcccgag tagctgggac cacagttgtg   28500
tgctaccaca cccggctaat ttttgtattt taatggcga tggggtttca ccatgttggc   28560
caggctggtc ttgaactcct gacctcaggt gatctgccca cctcggcctc ccaaagtgct   28620
gggattacag gcgtgagcca ccgcgcctgt aaatagatga ctattttaat atgaaattta   28680
aaaatagcta catctggaaa ttttataatt atacagataa tctaattact gtaatgtttt   28740
aaattcacac tttagcagaa tttaatgcha tctgtattaa ttcttaatg ttgatatacg   28800 gatttttttt agttgaacat atgtgaaaaa ctcacttta gttctaagtg aggaaaagta   28860
tcctgaacac tgcagtcttt tcagtgttg ctgattataa aaagcctaca tgctatatgc   28920
cttcttgcta ctcgagctaa aatgttgaat ataaataata cacttcattg gcacaaatgt   28980
aaactctaag gtagggcatg ctaaggaaat aaagagctgg cagtaaattt gttatttttt   29040
tttttttttt tttttttttt ttttgagacg gagtctcgct ctgtcgccca ggcgggactg   29100
cggactgcag tggcgcaatc tcggctcact gcaagctccg cttcccgggt tcacgccatt   29160
ctcctgcctc agcctcccga gtagctggga ctacaggcgc cgccaccgc gcccggctaa   29220 ttttttttg tatttttagt agagacgggg tttcaccttg ttagccagga tggtctcgat   29280
ctcctgacct catgatccac cgcctcggc ctcccaaagt gctggatta caggcgtgag   29340 ccaccgcgcc cggccaaatt tgttatttta aaacattaat ttgtctatct aatcatggta   29400
tacaagaaat tgtattttaa acagagtcgc ctttggcaga aaagtagagt gactataaaa   29460
ttccccaaag aaagtttcca agctt                                        29485

<210> SEQ ID NO 7
<211> LENGTH: 19
<212> TYPE: DNA
<213> ORGANISM: Pres-specific Primer, sense

<400> SEQUENCE: 7
tacctcacgg agccgctgg                                                19

<210> SEQ ID NO 8
<211> LENGTH: 21
<212> TYPE: DNA
<213> ORGANISM: Pres-specific primer, antisense

<400> SEQUENCE: 8
gcagtaatca gtccgtagtc c                                             21

<210> SEQ ID NO 9
<211> LENGTH: 22
<212> TYPE: DNA
<213> ORGANISM: Cyclophilin Primer, sense

<400> SEQUENCE: 9
tggcacagga ggaaagagca tc                                            22

<210> SEQ ID NO 10
<211> LENGTH: 22
<212> TYPE: DNA
<213> ORGANISM: Cyclophilin primer, antisense

<400> SEQUENCE: 10
```

```
aaagggcttc tccacctcga tc                                                    22
```

<210> SEQ ID NO 11
<211> LENGTH: 780
<212> TYPE: PRT
<213> ORGANISM: Rattus norvegicus

<400> SEQUENCE: 11

```
Met Ala Ala Arg Asp Arg Arg Ser Glu Pro Pro Gln Leu Ala Glu Tyr
1               5                   10                  15

Ser Cys Ser Tyr Ala Val Ser Arg Pro Val Tyr Ser Glu Leu Ala Phe
            20                  25                  30

Gln Gln Gln Arg Glu Arg Arg Leu Pro Glu Arg Arg Thr Leu Arg Asp
        35                  40                  45

Ser Leu Ala Arg Ser Cys Ser Cys Ser Arg Lys Arg Ala Phe Gly Ala
    50                  55                  60

Leu Lys Ala Leu Leu Pro Ile Leu Asp Trp Leu Pro Lys Tyr Arg Val
65                  70                  75                  80

Lys Glu Trp Leu Leu Ser Asp Ile Ile Ser Gly Val Ser Thr Gly Leu
                85                  90                  95

Val Gly Thr Leu Gln Gly Met Ala Tyr Ala Leu Leu Ala Ala Val Pro
            100                 105                 110

Val Gln Tyr Gly Leu Tyr Ser Ala Phe Phe Pro Ile Leu Thr Tyr Phe
        115                 120                 125

Val Phe Gly Thr Ser Arg His Ile Ser Val Gly Pro Phe Pro Val Val
    130                 135                 140

Ser Leu Met Val Gly Ser Val Val Leu Ser Met Ala Pro Asp Asp His
145                 150                 155                 160

Phe Leu Val Pro Ser Gly Asn Gly Ser Thr Leu Asn Thr Thr Thr Leu
                165                 170                 175

Asp Thr Gly Thr Arg Asp Ala Ala Arg Val Leu Leu Ala Ser Thr Leu
            180                 185                 190

Thr Leu Leu Val Gly Ile Ile Gln Leu Val Phe Gly Gly Leu Gln Ile
        195                 200                 205

Gly Phe Ile Val Arg Tyr Leu Ala Asp Pro Leu Val Gly Gly Phe Thr
    210                 215                 220

Thr Ala Ala Ala Phe Gln Val Leu Val Ser Gln Leu Lys Ile Val Leu
225                 230                 235                 240

Asn Val Ser Thr Lys Asn Tyr Asn Gly Val Leu Ser Ile Ile Tyr Thr
                245                 250                 255

Leu Ile Glu Ile Phe Gln Asn Ile Gly Asp Thr Asn Ile Ala Asp Phe
            260                 265                 270

Ile Ala Gly Leu Leu Thr Ile Ile Val Cys Met Ala Val Lys Glu Leu
        275                 280                 285

Asn Asp Arg Phe Lys His Lys Ile Pro Val Pro Ile Pro Ile Glu Val
    290                 295                 300

Ile Val Thr Ile Ile Ala Thr Ala Ile Ser Tyr Gly Ala Asn Leu Glu
305                 310                 315                 320

Ala Asn Tyr Asn Ala Gly Ile Val Lys Ser Ile Pro Ser Gly Phe Leu
                325                 330                 335

Pro Pro Val Leu Pro Ser Val Gly Leu Phe Ser Asp Met Leu Ala Ala
            340                 345                 350

Ser Phe Ser Ile Ala Val Val Ala Tyr Ala Ile Ala Val Ser Val Gly
        355                 360                 365
```

-continued

```
Lys Val Tyr Ala Thr Lys His Asp Tyr Ile Ile Asp Gly Asn Gln Glu
    370                 375                 380

Phe Ile Ala Phe Gly Ile Ser Asn Val Phe Ser Gly Phe Phe Ser Cys
385                 390                 395                 400

Phe Val Ala Thr Thr Ala Leu Ser Arg Thr Ala Val Gln Glu Ser Thr
                405                 410                 415

Gly Gly Lys Thr Gln Val Ala Gly Leu Ile Ser Ala Val Ile Val Met
                420                 425                 430

Val Ala Ile Val Ala Leu Gly Lys Leu Leu Glu Pro Leu Gln Lys Ser
            435                 440                 445

Val Leu Ala Ala Val Ile Ala Asn Leu Lys Gly Met Phe Met Gln
    450                 455                 460

Val Cys Asp Val Pro Arg Leu Trp Lys Gln Asn Lys Thr Asp Ala Val
465                 470                 475                 480

Ile Trp Val Phe Thr Cys Ile Met Ser Ile Leu Gly Leu Asp Leu
                485                 490                 495

Gly Leu Leu Ala Gly Leu Leu Phe Gly Leu Leu Thr Val Val Leu Arg
                500                 505                 510

Val Gln Phe Pro Ser Trp Asn Gly Leu Gly Ser Val Pro Ser Thr Asp
    515                 520                 525

Ile Tyr Lys Ser Ile Thr His Tyr Lys Asn Leu Glu Glu Pro Glu Gly
    530                 535                 540

Val Lys Ile Leu Arg Phe Ser Pro Ile Phe Tyr Gly Asn Val Asp
545                 550                 555                 560

Gly Phe Lys Lys Cys Val Lys Ser Thr Val Gly Phe Asp Ala Ile Arg
                565                 570                 575

Val Tyr Asn Lys Arg Leu Lys Ala Leu Arg Arg Ile Gln Lys Leu Ile
            580                 585                 590

Lys Lys Gly Gln Leu Arg Ala Thr Lys Asn Gly Ile Ile Ser Asp Val
            595                 600                 605

Gly Ser Ser Asn Asn Ala Phe Glu Pro Asp Glu Asp Val Glu Glu Pro
    610                 615                 620

Glu Glu Leu Asp Ile Pro Thr Lys Glu Ile Glu Ile Gln Val Asp Trp
625                 630                 635                 640

Asn Ser Glu Leu Pro Val Lys Val Asn Val Pro Lys Val Pro Ile His
                645                 650                 655

Ser Leu Val Leu Asp Cys Gly Ala Val Ser Phe Leu Asp Val Val Gly
                660                 665                 670

Val Arg Ser Leu Arg Met Ile Val Lys Glu Phe Gln Arg Ile Asp Val
            675                 680                 685

Asn Val Tyr Phe Ala Leu Leu Gln Asp Val Leu Glu Lys Met Glu
    690                 695                 700

Gln Cys Gly Phe Phe Asp Asp Asn Ile Arg Lys Asp Arg Phe Phe Leu
705                 710                 715                 720

Thr Val His Asp Ala Ile Leu Tyr Leu Gln Asn Gln Ala Lys Ser Arg
                725                 730                 735

Glu Gly Gln Asp Ser Leu Leu Glu Thr Ile Thr Leu Ile Gln Asp Cys
                740                 745                 750

Lys Asp Pro Leu Glu Leu Met Glu Ala Glu Ile Asn Glu Glu Glu Leu
            755                 760                 765

Asp Val Gln Asp Glu Ala Met Arg Arg Leu Ala Ser
    770                 775                 780
```

```
<210> SEQ ID NO 12
<211> LENGTH: 20
<212> TYPE: PRT
<213> ORGANISM: Synthetic Peptide from N-terminus of Prestin

<400> SEQUENCE: 12

Met Asp His Ala Glu Glu Asn Glu Ile Pro Val Ala Thr Gln Lys Tyr
1               5                   10                  15

His Val Glu Arg
            20

<210> SEQ ID NO 13
<211> LENGTH: 22
<212> TYPE: DNA
<213> ORGANISM: Primer for PCR amplification of C-terminus of prestin

<400> SEQUENCE: 13
gccctgaatt cctcgggtgt gg                                               22

<210> SEQ ID NO 14
<211> LENGTH: 21
<212> TYPE: DNA
<213> ORGANISM: Downstream Primer for C-terminus amplification

<400> SEQUENCE: 14
ggactacgga ctgattactg c                                                21

<210> SEQ ID NO 15
<211> LENGTH: 22
<212> TYPE: DNA
<213> ORGANISM: Primer for prestin N-terminus amplification

<400> SEQUENCE: 15
ctgcagaatt cggatcatgc cg                                               22

<210> SEQ ID NO 16
<211> LENGTH: 22
<212> TYPE: DNA
<213> ORGANISM: Upstream Primer for N-terminus amplification

<400> SEQUENCE: 16
caacgatggc tatggcaatg gc                                               22
```